United States Patent [19]
Wong et al.

[11] Patent Number: 5,461,143
[45] Date of Patent: Oct. 24, 1995

[54] OLIGOSACCHARIDE ENZYME SUBSTRATES AND INHIBITORS: METHODS AND COMPOSITIONS

[75] Inventors: Chi-Huey Wong; Yoshitaka Ichikawa, both of San Diego; Gwo-Jenn Shen, Carlsbad, all of Calif.

[73] Assignee: The Scripps Research Institute, La Jolla, Calif.

[21] Appl. No.: 219,242

[22] Filed: Mar. 29, 1994

Related U.S. Application Data

[63] Continuation of Ser. No. 889,652, May 26, 1992, abandoned, which is a continuation-in-part of Ser. No. 852,409, Mar. 16, 1992, abandoned, which is a continuation-in-part of Ser. No. 738,211, Jul. 30, 1991, abandoned, which is a continuation-in-part of Ser. No. 670,701, Mar. 18, 1991, Pat. No. 5,278,299, and a continuation-in-part of Ser. No. 707,600, May 30, 1991, abandoned.

[51] Int. Cl.$^6$ ................. C07H 5/04; C07H 5/10
[52] U.S. Cl. ............. 536/17.5; 536/4.1; 536/17.2; 536/17.3; 536/17.9; 536/118; 536/119
[58] Field of Search ................. 536/1.11, 4.1, 536/17.2, 17.3, 17.5, 18.7, 53, 54, 55, 55.2, 118, 119; 546/242, 244, 245; 541/13, 28

[56] References Cited

U.S. PATENT DOCUMENTS

| | | | |
|---|---|---|---|
| 4,918,009 | 4/1990 | Nilsson | 435/73 |
| 5,039,523 | 8/1991 | Payne et al. | 424/93 |
| 5,045,469 | 9/1991 | Payne et al. | 435/252.3 |
| 5,180,674 | 1/1993 | Roth | 435/288 |

FOREIGN PATENT DOCUMENTS

| | | |
|---|---|---|
| 3626915 | 2/1988 | Germany. |
| WO91/16449 | 10/1991 | WIPO. |

OTHER PUBLICATIONS

Roseman et al., *Chem. Phys. Lipids*, 51:270–297 (1970).
Flowers, *Meth. Enzymol.*, 138:359–404 (1987).
Paulsen, *Angew. Chemie*, 21(3):155–224 (1982).
Bock et al., *Carb. Res.*, 130:125–134 (1984).
Evans et al., *Tet. Letters*, 26(11):1465–1468 (1985).
Hindsgaul et al., *J. Biol. Chem.*, 266(27):17858 (1991).
Mizuochi et al., *J. Biol. Chem.*, 264(13):13834–13839 (1989).
Danishefsky, S. J. *J. Am. Chem. Soc.*, 111:6656 (1989).
Okamoto et al., *Tetrahedron*, 46:5835 (1990).
Ito et al., *Tetrahedron* 46:89 (1990).
Toone et al., *Tetrahedron*, 45:5365 (1989).
Beyer, et al., *Adv. Enzymol.*, 52:23 (1981).
Schanbacher, et al., *J. Biol. Chem.*, 245:5057 (1970).
Berliner, et al., *Mol. Cell. Biochem.*, 62:37 (1984).
Nunez, et al., *Biochemistry*, 19:495 (1980).
Barker, et al., *J. Biol. Chem.*, 247:7135 (1972).
Babad, et al., *J. Biol. Chem.*, 241:2672 (1966).
Schauer et al., *Biochem. Soc. Symp.*, 40:87 (1974).
Durrwachter et al., *J. Org. Chem.*, 1988, 53, 4175.
Pederson et al., *Tetrahedron Lett.* 1988, 29, 4645.
Von der Osten et al., *J. Am. Chem. Soc.* 1989, 111, 3924.
Pederson et al., *Heterocycles* 1989, 28, 477.
Pederson et al., *J. Org. Chem.* 1990 55, 489.
Weinreb et al., *Tetrahedron Lett.* 1986, 2099.
Gross et al., *Eur. J. Biochem.*, 168:595 (1987).
Vijay et al., *J. Biol. Chem.*, 250(1) 164 (1975).
Zapata et al., *J. Biol. Chem.*, 264(25) 14769 (1989).
Higa et al., *J. Biol. Chem.*, 260(15):8838 (1985).
Huse et al., *Science*, 246:1275 (1989).
Paulson, et al., 3. *Biol. Chem.*, 264:17615 (1989).
Aoki, et al., *EMBO*, 9:3171 (1990).
Shima, et al., *J. Ferm. Bioena.*, 68:75 (1989).
Ernst et al., *J. Biol. Chem.*, 264:3436 (1989).
Masibay et al., *Proc. Natl. Acad. Sci. U.S.A.*, 86:5733 (1989).
Toghrol et al., *Biochemistry*, 29:2349 (1990).
Joziasse et al., *Eur. J. Biochem.*, 191:75 (1990).
Kajimoto, et al., *J. Am. Chem. Soc.*, 113:6196 (1991).
Lowe, et al., *Cell*, 63:475 (1990).
Corey, et al., *J. Ora. Chem.*, 38:3224 (1973).
Schweden et al., *Arch. Biochem. Biophys.*, 1986, 248, 335.
Dale et al., *Biochemistry*, 1985, 24, 3530.
Short et al., *TNucleic Acids Res.*, 16:7583 (1988).
Van et al., *J. Biol. Chem.*, 262:17556 (1987).
Ozaki et al., *J. Am. Chem. Soc.* 1990, 112, 4970).
Lowe et al., *Genes and Development*, 4:1288 (1990).
Tabor et al., *Proc. Natl. Acad. Sci. USA*, 82:1074 (1985).
Ichikawa et al., *J. Am. Chem. Soc.*, 113:4698 (1991).
Shames et al., *Glycobiology*, 1:87 (1991).
Auge et al., *Tetrahed. Lett.*, 29:789 (1988).
Kean et al., *Methods Enzymol.*, 8:208 (1966).
Roseman, S. *Proc. Natl. Acad. Sci.*, 48:437 (1962).
Gross et al., *Eur. J. Biochem.*, 117:583 (1988).
Zhong et al., *J. Am. Chem. Soc.*, 113:683 (1991).
Auge et al., *Tetrahed. Lett.*, 25:4663 (1984).
Kim et al., *J. Am. Chem. Soc.*, 110:6481 (1988).
Auge et al., *New J. Chem.*, 12:733 (1988).
Brossmer et al., *Biochem. Biophy. Res. Comm.*, 96:1282 (1980).
Auge et al., *Tetrahedron*, 46:201 (1990).
Auge et al., *Tetrahed. Lett.*, 30:2217 (1989).
Dumas et al., *Bioorg. Med. Chem*, 1:425 (1991).
Sharma et al., *Carb. Res.*, 175:25 (1988).
Noller, *Chemistry of Organic Compounds*, W. B. Saunders Company, Philadelphia, 1951, p. 35.
Ichikawa et al., *J. Am. Chem. Soc.*, 114:9283–9298 (1992).
Ichikawa et al., *Anal. Biochem.*, 202:215–238 (1992).
Ainsberg, *Attorney's Dictionary of Patent Claims*, vol. 1, Matthew Bender, New York, pp. P–81 and P–82, and C–88 (1993).

(List continued on next page.)

*Primary Examiner*—Douglas W. Robinson
*Assistant Examiner*—Kathleen Kahler Fonda
*Attorney, Agent, or Firm*—Welsh & Katz, Ltd.

[57] ABSTRACT

Oligosaccharide compounds that are substrates and inhibitors of glycosyltransferase and glycosidase enzymes and compositions containing such compounds are disclosed. A method of glycosylation is also disclosed. An *E. coli* transformed with phagemid CMPSIL-1, which phagemid comprises a gene for a modified CMP-sialic acid synthetase enzyme, which transformed *E. coli* has the ATCC accession No. 68531 is also provided.

11 Claims, 3 Drawing Sheets

OTHER PUBLICATIONS

Stryer, *Biochemistry*, vol. 3, W. H. Freeman and Co., New York pp. 337–338 (1988).
U.S. Patent No. 4,387,088, Official Gazette entry.Sabesan, et al., *J. Am. Chem. Soc.* 108:2068 (1986).
Thiem, et al., *Angew. Chem. Int. Ed. Engl.* 25:1096 (1986).
David, et al., *Pure Appl. Chem.* 59:1501 (1987).
Simon, et al., *J. Am. Chem. Soc.* 110:7159 (1988).
Auge, et al., *Carbohydr. Res.* 193:288 (1989).
Auge, et al., *Carbohydr. Res.* 200:257 (1990).
Palcic, et al., *Carbohydr. Res.* 190:1 (1989).
Paulson, J. C., *TIBS,* 14:272 (1989).
Finne, J., *TIBS,* 129 (Mar. 1985).
Appert et al., *EMBO,* 9:3171 (1990).
Tsuda et al., *Eur. J. Biochem.* 188:405 (1990).
Phillips et al., *Science* 250:1130 (1990).
Weinstein et al., *J. Biol. Chem.,* 157(22):13845 (1982).
Wong et al; J. Org. Chem. 47:5416–5418 (1982).
Holmes et al; J. Biol. Chem. 261(8):3737–43 (1986).

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ATATTGAATT CTAAACTAGT CGCCAAGGAG ACAGTCATAA TGAGAACAAA AATTATTGCG        60
```

( 2 ) INFORMATION FOR SEQ ID NO:2:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GCGCTCTAGA CTATTAAGAA CCGTAGTCCG GAACGTCGTA CGGGTATTTA ACAATCTCCG        60
CTATTTC                                                                 67
```

( 2 ) INFORMATION FOR SEQ ID NO:3:

( i ) SEQUENCE CHARACTERISTICS:
        ( A ) LENGTH: 10 amino acids
        ( B ) TYPE: amino
        ( D ) TOPOLOGY: linear ( i i ) MOLECULE TYPE: peptide ( x i ) SEQUENCE DESCRIPTION: SEQ ID NO:3:

```
Tyr  Pro  Tyr  Asp  Val  Pro  Asp  Tyr  Ala  Ser
                    5                        10
```

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
ATATTGAATT CAGAAGGAGA TATACATATG AGAACAAAAA TTATT                       45
```

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

(xi) SEQUENCE DESCRIPTION: SEQ ID NO:5:

GCGCAAGCTT CATTTAACAA TCTCCG  26

(2) INFORMATION FOR SEQ ID NO:6:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

GCGCTCTAGA CTATTATTTA ACAATCTCCG CTATT  35

OLIGOSACCHARIDE ENZYME SUBSTRATES AND INHIBITORS: METHODS AND COMPOSITIONS

This invention was made with government support under Contract GM 44154 awarded by the National Institutes of Health. The government has certain rights in the invention.

CROSS-REFERENCE TO COPENDING APPLICATIONS

This application is a continuation of application Ser. No. 07/889,652, filed May 26, 1992, now abandoned, which is a continuation-in-part of U.S. patent application Ser. No. 07/852,409, filed Mar. 16, 1992, now abandoned, which is itself a continuation-in-part of U.S. patent application Ser. No. 07/738,211 filed Jul. 30, 1991, now abandoned, which is itself a continuation-in-part of U.S. patent application Ser. No. 07/670,701 filed Mar. 18, 1991, now U.S. Pat. No. 5,278,299, and U.S. patent application Ser. No. 07/707,600 filed May 30, 1991, now abandoned.

TECHNICAL FIELD

The present invention relates to oligosaccharide compounds, and more particularly to di-, tri- and tetrasaccharides that are substrates or inhibitors of glycosyltransferase and glycosidase enzymes, their manufacture and use.

BACKGROUND ART

The stereocontrolled synthesis of oligosaccharides based on sophisticated protection/deprotection, activation and coupling strategies has been well established. See, e.g., Danishefsky et al. *J. Am. Chem. Soc.*, 111:6656 (1989); Okamoto et al., *Tetrahedron*, 46:5835 (1990); and Ito et al., *Tetrahedron* 46:89 (1990). A useful alternative to the chemical synthesis is enzymatic oligosaccharide synthesis based on glycosyltransferase or glycosidase enzymes. Toone et al., *Tetrahedron*, 45:5365 (1989). One advantage of such enzymatic synthesis is the lack of extensive protection and deprotection steps. A disadvantage of such enzymatic synthesis is the apparent limitation of product formation that results from the specificity of glycosyltransferase and glycosidase enzymes.

Glycosyltransferases are highly specific enzymes that catalyze the transfer of activated donor monosaccharides to acceptor saccharides. That transfer results in the elongation or synthesis of an oligo- or polysaccharide.

A number of glycosyltransferase types have been described including sialyltransferases, fucosyltransferases, galactosyltransferases, N-acetylgalactosaminyltransferases, N-acetylglucosaminyltransferases and the like. Beyer, et al., *Adv. Enzymol.*, 52:23 (1981). The designation of those enzymes indicates the nature of the donor substrate. Thus, for example, a sialyltransferase transfers a sialic acid moiety to an acceptor molecule.

Within each of the general enzyme types set forth above, specific transferase enzymes are additionally designated by the type of glycosidic linkage formed. For example, a β1,4-galactosyltransferase transfers a galactosyl moiety to an acceptor molecule, forming a β1,4-glycosidic linkage with such acceptor.

Further, glycosyltransferases are characterized by the acceptor molecule to which the donor glycosyl compound is transferred. A β1,4-galactosyltransferase from bovine milk (GalT, EC 2.4.1.22) is known to accept N-acetylglucosamine (GlcNAc) and its glycosides (β is better than α-glycoside) as acceptor substrates. See, e.g., Schanbacher, et al., *J. Biol. Chem.*, 245:5057 (1970); Berliner, et al., *Mol. Cell. Biochem.*, 62:37 (1984); Nunez, et al., *Biochemistry*, 19:495 (1980); Beyer, et al., *Adv. Enzymol.*, 52:23 (1981); Barker, et al., *J. Biol. Chem.*, 247:7135 (1972); and Babad, et al., *J. Biol. Chem.*, 241:2672 (1966). Glucose and its α- and β-glucosides are also acceptable; however, lactalbumin is required for α-glucosides. Beyer, et al., supra.

Taken together with the donor and linkage specificity set forth above, such acceptor specificity is used to define unique products of glycosyltransferase activity.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are, thus, described with the name or abbreviation for the non-reducing saccharide (i.e., Gal), followed by the configuration of the glycosidic bond (α or β), the ring position of the non-reducing saccharide involved in the bond (1 or 2), the ring position of the reducing saccharide involved in the bond (2, 3, 4, 6 or 8), and then the name or abbreviation of the reducing saccharide (i.e., GlcNAc).

It is often extremely difficult to make synthetic saccharides that can be used to study naturally occurring synthetic routes by inhibiting the synthetic reactions. The lack of such synthetic inhibitors hampers attempts to investigate the effects of metabolic changes on carbohydrate production and turnover.

It is also often difficult to prepare novel, non-naturally occurring oligo- and polysaccharides that are useful as carriers or solubilizing agents for drugs and, which because of their non-natural structures, are resistant to degradation in vivo.

There is, therefore, a pressing need for oligosaccharide compounds and efficient methods of making the same that serve as substrates or inhibitors of transferase and glycosidase enzymes.

BRIEF SUMMARY OF THE INVENTION

The present invention provides novel oligosaccharides that are substrates for some glycosyltransferases and that inhibit other glycosyltransferase and glycosidase enzymes as well as a method for making such oligosaccharides. Those oligosaccharides are also useful as building blocks in the synthesis of other oligosaccharides such as sialyl Le$^x$ and its analogs.

In one aspect, the present invention contemplates an oligosaccharide that corresponds to structural Formula I:

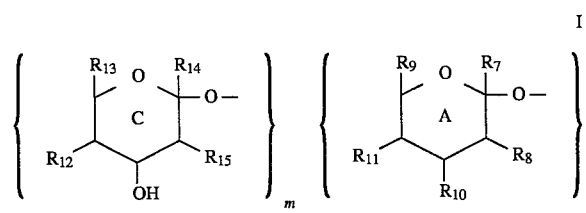

-continued

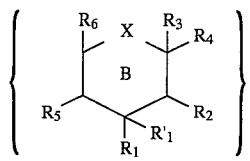

wherein X is O, S, SO, $SO_2$ or $NR_{16}$, wherein $R_{16}$ is hydrogen, $C_1$–$C_{12}$ acyl, $C_1$–$C_{12}$ alkyl, $C_1$–$C_4$ alkoxycarbonyl or >$NR_{16}$ is a $C_1$–$C_{12}$ alkyl N-oxide;

$R_1$ is absent, hydrogen, hydroxyl, $C_1$–$C_4$ acyl, $C_1$–$C_4$ alkoxycarbonyloxy, a saturated or unsaturated alkoxide or alkoxy alkoxide containing up to five carbon atoms or a glycosidially linked saccharide;

$R_1$' is hydrogen or $R_1$ and $R_1$' together form an oxo group;

$R_2$ is absent, hydrogen, hydroxyl, halide, $C_1$–$C_5$ alkoxy or $NR_{17}R_{18}$ where $R_{17}$ is hydrogen or $C_1$–$C_4$ alkyl and $R_{18}$ is hydrogen, $C_1$–$C_4$ alkyl, $C_1$–$C_4$ acyl, or $C_1$–$C_4$ alkoxycarbonyl, or $NR_{17}R_{18}$ together form a cyclic imido group containing 4–8 carbon atoms;

$R_3$ and $R_4$ are independently hydrogen, $C_1$–$C_4$ alkyl, hydroxyl, thiophenyl, $C_1$–$C_1$alkylthio, a saturated or unsaturated alkoxide or alkoxy alkoxide containing up to five carbon atoms, a glycosidically linked glucosyl, N-acetylglucosaminyl, galactosyl, N-acetylgalactosaminyl, fucosyl, mannosyl, rhamnosyl, sialyl group or a disaccharide thereof, or $R_3$ and $R_4$ together form an oxo group, with the proviso that at least one of $R_3$ and $R_4$ is hydrogen except when (i) $R_3$ and $R_4$ together form an oxo group, (ii) $R_2$ and $R_3$ are absent with their bonds forming ethylenic unsaturation or (iii) X is $NR_{16}$;

$R_5$ is absent, hydrogen, hydroxyl, methyl, $C_1$–$C_4$ acyl or $C_1$–$C_4$ alkoxycarbonyloxy;

$R_6$ is absent, hydrogen, hydroxymethyl, methyl, trihydroxypropyl, methylene $C_1$–$C_4$ acyloxy or benzyloxy;

$R_7$ is hydrogen or carboxyl;

$R_8$ is hydrogen, hydroxyl or acetamido;

$R_9$ is hydroxymethyl, methyl, trihydroxypropyl, methylene $C_1$–$C_4$ acyloxy or benzyloxy, and 3-acetoxy-1,2-dihydroxypropyl, 3-1actyloxy-1,2-dihydroxypropyl, 3-azido-1,2-dihydroxypropyl, and 3-fluoro-1,2-dihydroxypropyl when $R_8$ is hydrogen and $R_{11}$ is N-acetylamino;

$R_{10}$ is absent, hydroxyl or acetamido;

$R_{11}$ is absent, hydroxyl or acetamido;

$R_{12}$ is hydroxyl or acetamido;

$R_{13}$ is hydroxymethyl or trihydroxypropyl, and 3-acetoxy-1,2-dihydroxypropyl, 3-lactyloxy-1,2-dihydroxypropyl, 3-azido-1,2-dihydroxypropyl, and 3-fluoro-1,2-dihydroxypropyl when $R_{15}$ is hydrogen and $R_{12}$ is N-acetylamino;

$R_{14}$ is hydrogen or carboxyl;

$R_{15}$ is hydrogen, hydroxyl or acetamido; and m is zero or one such that when m is zero, ring C is absent and when m is one, ring C is present;

with the provisos (a) that one of substituents $R_1$, $R_2$ and $R_5$ or a hydroxyl group of $R_6$ is absent from ring B and ring B is joined to ring A through a glycosidic bond to the ring B carbon of the absent substituent, and that a numbered substituent or hydroxyl is only absent when ring A is joined to ring B at the position of that substituent or hydroxyl except as enumerated herein; (b) that when m is one, one of substituents $R_{10}$ and $R_{11}$ or a hydroxyl group of $R_9$ is absent from ring A and ring C is joined to ring A through a glycosidic bond to the ring A carbon of the absent substituent or hydroxyl, and that numbered substituent or hydroxyl is only absent when ring C is joined to ring A at the position of that substituent or hydroxyl, or a second of $R_1$, $R_2$, $R_5$ or a hydroxyl of $R_6$ is absent and ring C is joined to ring B through a glycosidic bond to the ring B carbon of the second absent substituent or hydroxyl; (c) that X is O only if one of the following structures is present; (i) $R_1$ and $R_1$' together form an oxo group, (ii) $R_1$ and either $R_3$ or $R_4$ are not hydroxyl, (iii) $R_3$ and $R_4$ together form an oxo group, (iv) either $R_3$ and $R_4$ is $C_1$–$C_3$ alkylthio, or (v) $R_2$ and $R_3$ are absent and their bonds form ethylenic unsaturation and either $R_1$, $R_5$, $R_8$ or $R_9$ is not hydroxyl or $R_6$ is not hydroxymethyl; and (d) that $R_2$ and $R_3$ are absent and their bonds form ethylenic unsaturation only when X is O.

In another aspect, the present invention contemplates an oligosaccharide that corresponds to structural Formula II:

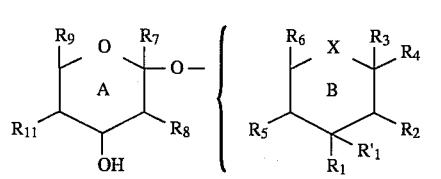

wherein X is O, S, SO, $SO_2$ or $NR_{16}$, wherein $R_{16}$ is hydrogen, $C_1$–$C_{12}$ acyl, $C_1$–$C_{12}$ alkyl, $C_1$–$C_4$ alkoxycarbonyl or >$NR_{16}$ is a $C_1$–$C_{12}$ alkyl N-oxide;

$R_1$ is absent, hydrogen, hydroxyl, $C_1$–$C_4$ acyl, $C_1$–$C_4$ alkoxycarbonyloxy, a saturated or unsaturated alkoxide or alkoxy alkoxide containing up to 5 carbon atoms or a glycosidically linked saccharide;

$R_1$' is hydrogen or $R_1$ and $R_1$' together form an oxo group;

$R_2$ is absent, hydrogen, hydroxyl, halide, $C_1$–$C_5$ alkoxy or $NR_{12}R_{18}$ where $R_{17}$ is hydrogen or $C_1$–$C_4$ alkyl and $R_{18}$ is hydrogen, $C_1$–$C_4$ alkyl, $C_1$–$C_4$ acyl, or $C_1$–$C_4$ alkoxycarbonyl, or $NR_{17}TR_{18}$ together form a cyclic imido group containing 4–8 carbon atoms;

$R_3$ and $R_4$ are independently hydrogen, $C_1$–$C_4$ alkyl, hydroxyl, thiophenyl, $C_1$–$C_3$ alkylthio, a saturated or unsaturated alkoxide or alkoxy alkoxide containing up to 5 carbon atoms, a glycosidically linked glucosyl, N-acetylglucosaminyl, galactosyl, N-acetylgalactosaminyl, fucosyl, mannosyl, rhamnosyl, sialyl group or a disaccharide thereof, or $R_3$ and $R_4$ together form an oxo group, with the proviso that at least one of $R_3$ and $R_4$ is hydrogen except when (i) $R_3$ and $R_4$ together from an oxo group, (ii) $R_2$ and $R_3$ are absent with their bonds forming ethylenic unsaturation or (iii) X is $NR_{16}$;

$R_5$ is absent, hydrogen, hydroxyl, methyl, $C_1$–$C_4$ acyl or $C_1$–$C_4$ alkoxycarbonyloxy;

$R_6$ is absent, hydroxymethyl, methyl, trihydroxypropyl, methylene $C_1$–$C_4$ acyloxy or benzyloxy;

$R_7$ is hydrogen or carboxyl;

$R_8$ is absent, hydroxyl or acetamido;

$R_9$ is hydroxymethyl, methyl, trihydroxypropyl, methylene $C_1$–$C_4$ acyloxy or benzyloxy, and 3-acetoxy-1,2-dihydroxypropyl, 3-lactyloxy-1,2-dihydroxypropyl, 3-azido-1,2-dihydroxypropyl, and 3-fluoro-1,2-dihydroxypropyl when $R_8$ is hydrogen and $R_{11}$ is N-acetylamino;

$R^{11}$ is hydroxyl or acetamido;

with the provisos (a) that one of substituents $R_1$, $R_2$, $R_5$ or a hydroxyl group of $R_6$ is absent from ring B and ring B is joined to ring A through a glycosidic bond to the ring B carbon of the absent substituent, and that a numbered substituent or hydroxyl is only absent when ring A is joined to ring B at the position of that substituent or hydroxyl except as enumerated herein; (b) that X is O only if one of the following structures is present; (i) $R_1$ and $R_1'$ together form an oxo group, (ii) $R_1$ and either $R_3$ or $R_4$ are not hydroxyl, (iii) $R_3$ and $R_4$ together form an oxo group, (iv) either $R_3$ or $R_4$ is $C_1$–$C_3$ alkylthio, or (v) $R_2$ and $R_3$ are absent and their bonds form ethylenic unsaturation and either or $R_9$ is not hydroxyl or $R_6$ is not hydroxymethyl; and (c) that $R_2$ and $R_3$ are absent and their bonds form ethylenic unsaturation only when X is O.

In another aspect, the present invention provides a method of glycosylation that comprises the steps of admixing in an aqueous medium an activated donor monosaccharide with an acceptor saccharide, of Formula II, above, or of Formula III below, in the presence of a catalytic amount of a glycosyltransferase having specificity for both the activated donor monosaccharide and the acceptor saccharide to form a reaction mixture:

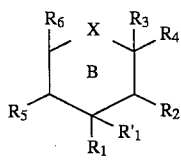

III wherein X and $R_{1-6}$ of Formula III are as defined in Formula II above, and maintaining the reaction mixture for a time period and under conditions sufficient for the acceptor saccharide to be glycosylated and form a glycosylated acceptor saccharide.

In a preferred embodiment, the glycosylation method comprises the steps of:

(a) admixing in the presence of each other in an aqueous medium (i) an acceptor saccharide;

(ii) a donor monosaccharide;

(iii) an activating nucleotide having specificity for the donor monosaccharide;

(iv) an activated donor monosaccharide regenerating system;

(v) a pyrophosphate scavenger; and (vi) catalytic amounts of a glycosyltransferase having specificity for both the activated form of the donor monosaccharide and the acceptor saccharide and a nucleotide-sugar-pyrophosphorylase having specificity for both the donor monosaccharide and the activating nucleotide to form a reaction mixture; and (b) maintaining the reaction mixture for a time period and under conditions sufficient for the acceptor saccharide to be glycosylated and form a glycosylated acceptor saccharide.

The acceptor saccharide can be an acceptor monosaccharide or an acceptor oligosaccharide. The acceptor oligosaccharide can itself be prepared in the reaction mixture, which reaction mixture further includes:

(a) a second acceptor saccharide;

(b) a second donor monosaccharide;

(c) a second activating nucleotide that has specificity for the second donor monosaccharide;

(d) a second activated donor monosaccharide regenerating system; and (e) catalytic amounts of (i) a glycosyltransferase having specificity for both the activated form of the second donor monosaccharide and the second acceptor saccharide and (ii) a nucleotide-sugar-pyrophosphorylase having specificity for both the second donor monosaccharide and the second activating nucleotide.

The activated donor monosaccharide regenerating system used in the glycosylation method comprises a phosphate donor and a catalytic amount of a kinase that catalyzes the transfer of phosphate from the phosphate donor to an activating nucleotide.

The present invention also contemplates an *E. coli* transfected with phagemid CMPSIL-1, which phagemid comprises a gene encoding a modified CMP-sialic acid synthetase enzyme. That transformed *E. coli* has the ATCC accession No. 68531. Phagemid CMPSIL-W10 and *E. coli* transfected with that phagemid are also contemplated.

The present invention still further contemplates an acceptor saccharide of Formula III above.

Also contemplated by the present invention is a composition that comprises a glycosyltransferase or glycosidase inhibiting amount of a before-described oligosaccharide compound dispersed in an aqueous medium. The aqueous medium is preferably pharmaceutically acceptable..

BRIEF DESCRIPTION OF THE DRAWINGS

In the drawings that form a portion of the specification.

Figure 1:
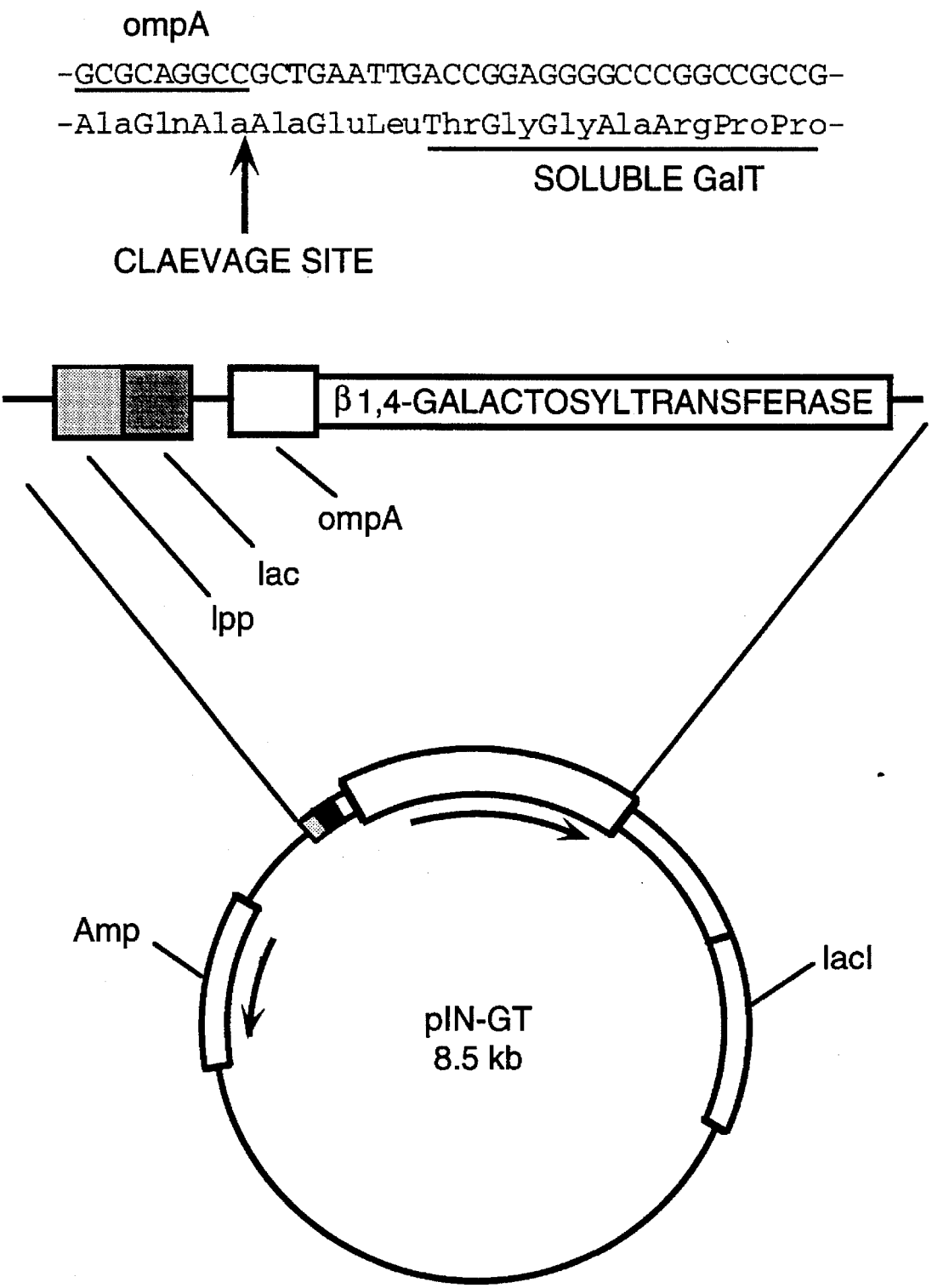
FIG. 1 is a schematic diagram of plasmid pIN-GT showing the location of the GalT gene as well as other components.

DETAILED DESCRIPTION OF THE
INVENTION THE COMPOUNDS

A compound of the invention is an oligosaccharide, i.e., a compound containing two to ten saccharide units, and, preferably a disaccharide, trisaccharide or tetrasaccharide.

In one embodiment, an oligosaccharide of the present invention corresponds to structural Formula I:

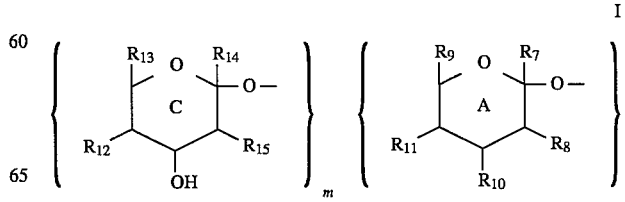

I

-continued

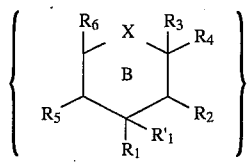

wherein X is O, S, SO, $SO_2$ or $NR_{16}$, wherein $R_{16}$ is hydrogen, $C_1$–$C_{12}$ acyl, $C_1$–$C_{12}$ alkyl, $C_1$–$C_4$ alkoxycarbonyl or >$NR_{16}$ is a $C_1$–$C_{12}$ alkyl N-oxide;

$R_1$ is absent, hydrogen, hydroxyl, $C_1$–$C_4$ acyl, $C_1$–$C_4$ alkoxycarbonyloxy, a saturated or unsaturated alkoxide or alkoxy alkoxide containing up to five carbon atoms or a glycosidially linked saccharide;

$R_1'$ is hydrogen or $R_1$ and $R_1'$ together form an oxo group;

$R_2$ is absent, hydrogen, hydroxyl, halide, $C_1$–$C_5$ alkoxy or $NR_{17}R_{18}$ where $R_{17}$ is hydrogen or $C_1$–$C_4$ alkyl and $R_{18}$ is hydrogen, $C_1$–$C_4$ alkyl, $C_1$–$C_4$ acyl, or $C_1$–$C_4$ alkoxycarbonyl, or $NR_{17}R_{18}$ together form a cyclic imido group containing 4–8 carbon atoms;

$R_3$ and $R_4$ are independently hydrogen, $C_1$–$C_4$ alkyl, hydroxyl, thiophenyl, $C_1$–$C_3$ alkylthio, a saturated or unsaturated alkoxide or alkoxy alkoxide containing up to five carbon atoms, a glycosidically linked glucosyl, N-acetylglucosaminyl, galactosyl, N-acetylgalactosaminyl, fucosyl, mannosyl, rhamnosyl, sialyl group or a disaccharide thereof, or $R_3$ and $R_4$ together form an oxo group, with the proviso that at least one of $R_3$ and $R_4$ is hydrogen except when (i) $R_3$ and $R_4$ together form an oxo group, (ii) $R_2$ and $R_3$ are absent with their bonds forming ethylenic unsaturation or (iii) X is $NR_{16}$;

$R_5$ is absent, hydrogen, hydroxyl, methyl, $C_1$–$C_4$ acyl or $C_1$–$C_4$ alkoxycarbonyloxy;

$R_6$ is absent, hydrogen, hydroxymethyl, methyl, trihydroxyropyl, methylene $C_1$–$C_4$ acyloxy or benzyloxy;

$R_7$ is hydrogen or carboxyl;

$R_8$ is hydrogen, hydroxyl or acetamido;

$R_9$ is hydroxymethyl, methyl, trihydroxypropyl, methylene $C_1$–$C_4$ acyloxy or benzyloxy, and 3-acetoxy-1,2-dihydroxypropyl, 3-lactyloxy-1,2-dihydroxypropyl, 3-azido-1,2-dihydroxypropyl, and 3-fluoro-1,2-dihydroxypropyl when $R_8$ is hydrogen and $R_{11}$ is N-acetylamino;

$R_{10}$ is absent, hydroxyl or acetamido;

$R_{11}$ is absent, hydroxyl or acetamido;

$R_{12}$ is hydroxyl or acetamido;

$R_{13}$ is hydroxymethyl or trihydroxypropyl, and 3-acetoxy-1,2-dihydroxypropyl, 3-lactoyloxy-1,2-dihydroxypropyl, 3-azido-1,2-dihydroxypropyl, and 3-fluoro-1,2-dihydroxypropyl when $R_{15}$ is hydrogen and $R_{12}$ is N-acetylamino;

$R_{14}$ is hydrogen or carboxyl;

$R_{15}$ is hydrogen, hydroxyl or acetamido; and m is zero or one such that when m is zero, ring C is absent and when m is one, ring C is present; and with the provisos (a) that one of substituents $R_1$, $R_2$ and $R_5$ or a hydroxyl group of $R_6$ is absent from ring B and ring B is joined to ring A through a glycosidic bond to the ring B carbon of the absent substituent, and that a numbered substituent or hydroxyl is only absent when ring A is joined to ring B at the position of that substituent or hydroxyl except as enumerated herein; (b) that when m is one, one of substituents $R_{10}$ and $R_{11}$ or a hydroxyl group of $R_9$ is absent from ring A and ring C is joined to ring A through a glycosidic bond to the ring A carbon of the absent substituent or hydroxyl, and that numbered substituent or hydroxyl is only absent when ring C is joined to ring A at the position of that substituent or hydroxyl, or a second of $R_1$, $R_2$, $R_5$ or a hydroxyl of $R_6$ is absent and ring C is joined to ring B through a glycosidic bond to the ring B carbon of the second absent substituent or hydroxyl; (c) that X is O only if one of the following structures is present; (i) $R_1$ and $R_1'$ together form an oxo group, (ii) $R_1$ and either $R_3$ or $R_4$ are not hydroxyl, (iii) $R_3$ and $R_4$ together form an oxo group, (iv) either $R_3$ and $R_4$ is $C_1$–$C_3$ alkylthio, or (v) $R_2$ and $R_3$ are absent and their bonds form ethylenic unsaturation and either $R_1$, $R_5$, $R_8$ or $R_9$ is not hydroxyl or $R_6$ is not hydroxymethyl; and (d) that $R_2$ and $R_3$ are absent and their bonds form ethylenic unsaturation only when X is O.

Another oligosaccharide compound of the present invention that corresponds to structural Formula II

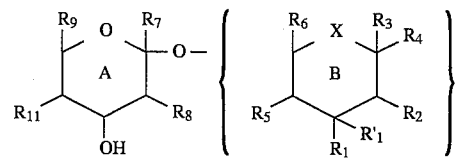

II wherein X is O, S, SO, $SO_2$ or $NR_{16}$, wherein $R_{16}$ is hydrogen, $C_1$–$C_{12}$ acyl, $C_1$–$C_{12}$ alkyl, $C_1$–$C_4$ alkoxycarbonyl or >$NR_{16}$ is a $C_1$–$C_{12}$ alkyl N-oxide;

$R_1$ is absent, hydrogen, hydroxyl, $C_1$–$C_4$ acyl, $C_1$–$C_4$ alkoxycarbonyloxy, a saturated or unsaturated alkoxide or alkoxy alkoxide containing up to 5 carbon atoms or a glycosidically linked saccharide;

$R_1'$ is hydrogen or $R_1$ and $R_1'$ together form an oxo group;

$R_2$ is absent, hydrogen, hydroxyl, halide, $C_1$–$C_5$ alkoxy or $NR_{12}R_{18}$ where $R_{17}$ is hydrogen or $C_1$–$C_4$ alkyl and $R_{18}$ is hydrogen, $C_1$–$C_4$ alkyl, $C_1$–$C_4$ acyl, or $C_1$–$C_4$ alkoxycarbonyl, or $NR_{17}R_{18}$ together form a cyclic imido group containing 4–8 carbon atoms;

$R_3$ and $R_4$ are independently hydrogen, $C_1$–$C_4$ alkyl, hydroxyl, thiophenyl, $C_1$–$C_3$ alkylthio, a saturated or unsaturated alkoxide or alkoxy alkoxide containing up to carbon atoms, a glycosidically linked glucosyl, N-acetylglucosaminyl, galactosyl, N-acetylgalactosaminyl, fucosyl, mannosyl, rhamnosyl, sialyl group or a disaccharide thereof, or $R_3$ and $R_4$ together form an oxo group, with the proviso that at least one of $R_3$ and $R_4$ is hydrogen except when (i) $R_3$ and $R_4$ together from an oxo group, (ii) $R_2$ and $R_3$ are absent with their bonds forming ethylenic unsaturation or (iii) X is $NR_{16}$;

$R_5$ is absent, hydrogen, hydroxyl, methyl, $C_1$–$C_4$ acyl or $C_1$–$C_4$ alkoxycarbonyloxy;

$R_6$ is absent, hydrogen, hydroxymethyl, methyl, trihydroxypropyl, methylene $C_1$–$C_4$ acyloxy or benzyloxy;

$R_7$ is hydrogen or carboxyl;

$R_8$ is absent, hydroxyl or acetamido;

$R_9$ is hydroxymethyl, methyl, trihydroxypropyl, methylene $C_1$–$C_4$ acyloxy or benzyloxy, and 3-acetoxy-1,2-dihydroxypropyl, 3-lactyloxy-1,2-dihydroxypropyl, 3-azido-1,2-dihydroxypropyl, and 3-fluoro-1,2-dihydroxypropyl when $R_8$ is hydrogen and $R_{11}$ is N-acetylamino;

$R^{11}$ is hydroxyl or acetamido;

with the provisos (a) that one of substituents $R_1$, $R_2$, $R_5$ or a hydroxyl group of $R_6$ is absent from ring B and ring B is joined to ring A through a glycosidic bond to the ring B carbon of the absent substituent, and that a numbered substituent or hydroxyl is only absent when ring A is joined to ring B at the position of that substituent or hydroxyl except as enumerated herein; (b) that X is O only if one of the following structures is present; (i) $R_1$ and $R_1'$ together form an oxo group, (ii) $R_1$ and either $R_3$ or $R_4$ are not hydroxyl, (iii) $R_3$ and $R_4$ together form an oxo group, (iv) either $R_3$ or $R_4$ is $C_1$–$C_3$ alkylthio, or (v) $R_2$ and $R_3$ are absent and their bonds form ethylenic unsaturation and either $R_1$, $R_5$, $R_8$ or $R_9$ is not hydroxyl or $R_6$ is not hydroxymethyl; and (c) that $R_2$ and $R_3$ are absent and their bonds form ethylenic unsaturation only when X is O.

Exemplary saccharide (sugar) units contain six-membered rings and include substituent configurations of common, naturally occurring sugars such as glucose (Glc), N-acetylglucosamine (GlcNAc), galactose (Gal), N-acetylgalactosamine (GalNAc), mannose (Man), rhamnose (Rha), fucose (Fuc), sialic acid (NeuAc), and the like, and their 2-deoxy derivatives.

The saccharide units are joined together by a glycosidic bond. Typically, the glycosidic bond is between the carbon atom at position 1 of the non-reducing end sugar (ring A of Formulas I or II) and the carbon atom at position 2, 3, 4 or 6 of the reducing end sugar (ring B of Formulas I or II). When the non-reducing end sugar is sialic acid, the glycosidic bond is between the carbon atom at position 2 of sialic acid and the carbon atom at positions 2, 3, 4, 6 or 8 of the reducing end sugar.

The glycosidic bonding can have an α or a β configuration. β1,4-, α1,3- and α2,6-bonding are used as exemplary herein, and are preferred. Other bond configurations are also contemplated.

In the above formulas, and in the other formulas utilized herein, typically only one group at each of the ring carbon atoms is shown. The fourth, unshown group bonded to each of those ring carbons is a hydrogen atom, as would be present in an unsubstituted carbohydrate. The two shown "fourth groups" are so shown to permit an oxo group to be present. Additionally, when $R_3$ and $R_4$ are hydrogen and hydroxyl, both anomers are contemplated.

The above structural formulas and of those set forth hereinafter also do not show the orientation of groups $R_{1-15}$ relative to the plane of the ring. Each of the α- and β-orientations is contemplated for each of $R_{1-15}$, so those substituent groups are shown generally.

The orientation of a substituent is a function of the precursor molecule, and the substituent orientation can be varied as desired. As will be discussed hereinafter, particular orientations of $R_{1-15}$ are preferred.

In regard to Formula I, it is first noted that ring C is present when m is one and absent when m is zero. Thus, when m is zero, Formula I reduces to Formula II. When m is one, ring C can be bonded to ring A (Schemes 1 and 2) or to ring B (Scheme 3 and Table 1a) so that a linear or branched oligosaccharide, respectively, is formed by the oxygen shown as unbonded in the formula. Ring A is always joined to ring B in both of Formulas I and II. One of $R_1$, $R_2$, $R_5$ or a hydroxyl of $R_6$ ring B is therefore always absent and is replaced by a glycosidic bond to ring A.

In addition, when ring C is present (m=1) and also glycosidically linked to ring B, a second of $R_1$, $R_2$, $R_5$ or a hydroxyl of $R_6$ is absent and is replaced by another, second glycosidic bond to ring C. When ring C is present and glycosidically linked to ring A, one of $R_{11}$, $R_{10}$ or a hydroxyl of $R_9$ is absent and replaced by a glycosidic bond to ring C.

In usual practice, $R_1$ and/or $R_5$ are replaced by the glycosidic bonds when ring A or C are other than sialyl. However, when either of rings A or C are sialyl, a hydroxyl of an $R_6$ or $R_9$ hydroxymethyl group is replaced by the glycosidic bond.

The rings labeled A and B in Formula II are bonded together by the oxygen of the glycosidic bond of ring A shown to the left of the left bracket. That oxygen atom can be bonded to one of the carbon atoms of Ring B that is shown linked to $R_1$, $R_2$, $R_5$ or $R_6$ and the appropriate $R_1$, $R_2$, $R_5$ or $R_6$ hydroxyl group is consequently absent. Thus, for example, where $R_7$ is hydrogen, a 1,3 -; 1,2 -; 1,4 -; or 1,6-bond can be formed between rings A and B at the positions of $R_1$, $R_2$, $R_5$ or $R_6$, respectively, and the corresponding $R_1$, $R_2$, $R_5$ or $R_6$ substituent group is absent. Where $R_7$ is carboxyl, that bonding can be 2,3-; 2,2-; 2,4-; or 2,6-, respectively.

Turning more specifically to Formulas I and II, it is seen that substituent X of ring B can be O, S, SO, $SO_2$ or $NR_{16}$. The $R_{16}$ group can be hydrogen, which is preferred, as well as a $C_1$–$C_{12}$ acyl group, a $C_1$–$C_{12}$ alkyl group or >$NR_{16}$ can be a $C_1$–$C_{12}$ alkyl N-oxide.

An $R_{16}$ $C_1$–$C_{12}$ acyl group is the residuum or reaction product of a corresponding $C_1$–$C_{12}$ carboxylic acid, and thus forms an amide with the nitrogen atom. A contemplated $C_1$–$C_{12}$ acyl group includes formyl, acetyl, propionyl, butanoyl, iso-butanoyl, hexanoyl, octanoyl, nonanoyl, decanoyl, dodecanoyl (lauroyl), cyclohexanecarbonyl and benzoyl.

A >$NR_{16}$ is a $C_1$–$C_{12}$ alkyl N-oxide. Here, the alkyl group is as is discussed below and the alkylated tertiary nitrogen atom is oxidized to form the N-oxide. The symbol ">" is used to show the remaining valences of the nitrogen that are bonded to ring carbon atoms.

A $C_1$–$C_{12}$ alkyl group is exemplified by methyl, ethyl, propyl, iso-propyl, butyl, t-butyl, pentyl, hexyl, cyclohexyl, heptyl, octyl, nonyl, decyl and dodecyl groups.

A $C_1$–$C_4$ acyl group as can be present as $R_1$, $R_5$ or $R_{18}$, or a $C_1$–$C_4$ acyloxy group of $R_6$ and $R_9$ are the acyl [RC(O)-] or acyloxy [ROC(O)-] portions of ester groups, where R is the hydrocarbon portion of the acyl group. A $C_1$–$C_4$ acyl group includes formyl, acetyl, propionyl, butanoyl and iso-butanoyl.

A saturated alkoxide is an ether whose hydrocarbon portion is saturated. A $C_1$–$C_5$ alkoxide can contain a length of 1 to 6 atoms in the group whose hydrocarbon portion can be methyl, ethyl, propyl, isopropyl, butyl or pentyl groups. A 2-trimethylsilylethyl "hydrocarbon" group can be also included. A methoxy group is preferred.

An unsaturated alkoxide is an ether like an alkoxide that further includes ethylenic unsaturation in the hydrocarbon group. An unsaturated alkoxide also can have a length up to 6 atoms in the group of which 5 atoms can be carbon, and whose hydrocarbon portion includes a vinyl group, an allyl group (prop-2-enyl), a methylvinyl group (prop-1-enyl), a 2-butenyl and a 2-pentenyl group. An allyl hydrocarbon group (allyloxy) is preferred.

An alkoxy alkoxide is an ether that includes another ether group. An alkoxy alkoxide can also have a length of 6 atoms in the group, 5 of which are carbon. Exemplary 6 atom alkoxy alkoxides include methoxylmethyoxy (—O—$CH_2$—O—$CH_3$), ethoxylmethyoxy (—O—$CH_2$—O—$C_2H_5$) and ethoxylethyoxy (—O—$C_2H_5$—O—$C_2H_5$).

Inasmuch as saturated alkoxide, unsaturated alkoxide and alkoxy alkoxide groups can each contain a chain length of up to 6 atoms of which 5 are carbon, those three moieties are collectively referred to as a saturated or unsaturated alkoxide or alkoxy alkoxide containing up to 5 carbons.

An $R_1$ and $R_5$ can also include a $C_1-C_4$ alkoxycarbonyl group, whereas an $R_{16}$ and $R_{18}$ can include a $C_1-C_4$ alkoxycarbonyl. The former is a carbonate, whereas the latter is a urethane. Each can be prepared by reaction of a $C_1-C_4$ alkoxy (as discussed before) chloroformate with an alcohol or amine, for the formation of an $R_1$ or $R_5$ group, or an $R_{16}$ or $R_{18}$ group, respectively.

$R_2$ can also be $NR_{17}R_{18}$, where $NR_{17}R_{18}$ together form a cyclic imido group containing 4–8 carbon atoms. Contemplated cyclic imide groups include succinimido, methylsuccinimido, 2,2-dimethylsuccinimido, 2,3-dimethylsuccinimido, maleimido, phthalimido, hexahydrophthalimido and dimethylphthalimido.

An oxo group is a carbonyl group and can be present in a B ring of the above Formula I, II or III at the 3-position of the ring B ($R_1$ and $R_1'$) as a ketone, or at the 1-position of ring B ($R_3$ and $R_4$) as the carbonyl portion of a lactone, thiolactone or lactam.

A $C_1-C_3$ alkylthio group is a thio ether in which the ether oxygen of an alkoxide is replaced by a sulfur atom. The hydrocarbon portion of a $C_1-C_3$ alkylthio can be the same as the groups noted above for the saturated and unsaturated alkoxide groups.

The $R_2$ and $R_3$ groups can also be absent, with their bonds forming an ethylenic unsaturation between the 1- and 2-positions of the ring. The resulting B ring saccharide unit is, thereby, a glycal.

For a particularly preferred disaccharide, $R_8$ is hydroxyl. An $R_8$ group can also be an N-acetamido group as where Ring A is an N-acetyl-glucosaminyl group.

Where a trisaccharide is desired, $R_2$ can be another saccharide that is linked to the depicted saccharide by a glycosidic bond. Exemplary saccharides that can be so linked are noted hereinbefore.

In addition to the above-noted absence of an $R_1$, $R_2$, $R_5$ or $R_6$ group to account for linkage of the A and B as well as the C and B rings of the above Formula I, two other provisos apply as to a compound of Formulas I and II. Both of these provisos relate to compounds in which X is O, and thereby limit those compounds.

First, X is O only where one of five substituent configurations of ring B is present. Two of those configurations are oxo groups ($R_1$ and $R_1'$) and ($R_3$ and $R_4$). The third is where either $R_3$ or $R_4$ is $C_1-C_4$ alkylthio. The fourth occurs where $R_1$ and either $R_3$ or $R_4$ are not hydroxyl. The fifth occurs where $R_2$ and $R_3$ are absent with their bonds forming ethylenic unsaturation (ring B is a glycal) and either $R_1$, $R_5$, $R_8$ or $R_9$ is not hydroxyl or $R_6$ is not hydroxymethyl.

Second, $R_2$ and $R_3$ are absent and replaced by ethylenic unsaturation only when X is O. Thus, only a glycal is contemplated.

In a preferred embodiment, X is S, SO or $SO_2$ and ring B is a thiosugar or its oxygenated derivative. Where ring B is a thiosugar, preferably $R_1$, $R_2$ and $R_5$ are hydroxyl, $R_3$ is hydrogen, hydroxyl or methoxy, $R_4$ is hydrogen, hydroxyl or methoxy, with the proviso that one of $R_3$ and $R_4$ is hydrogen, and $R_6$ is hydroxymethyl.

In yet another preferred embodiment, X is $NR_{16}$ and ring B forms an azasugar. Where $NR_{16}$ is NH, preferably $R_1$ is hydroxyl, $R_1'$ is hydrogen, $R_2$ is hydroxyl or acetamido, $R_3$ and $R_4$ are both hydrogen or $R_3$ and $R_4$ together form an oxo group, $R_6$ is hydroxymethyl and ring B is joined to ring A through a glycosidic bond at $R_5$.

Alternatively, where X is $NR_{16}$, ring B can be a 1,6-dideoxy azapyranose. Where ring B is a 1,6-dideoxy azapyranose, preferably $R_1$ is hydrogen or hydroxyl; $R_2$ is hydrogen, hydroxyl, $C_1-C_5$ alkoxy, halide or $NR_{17}R_{18}$ where $R_{17}$ is hydrogen or $C_1-C_4$ alkyl and $R_{18}$ is hydrogen, $C_1-C_4$ alkyl, $C_1-C_4$ acyl, $C_{-C4}$ alkoxycarbonyl or $NR_{17}R_{18}$ together form a cyclic imido group containing 4–8 carbon atoms; $R_3$ and $R_4$ are both hydrogen; $R_5$ is hydrogen, hydroxyl or methyl; $R_6$ is hydrogen or methyl with the proviso that only one of $R_5$ and $R_6$ is methyl; $R_{16}$ is hydrogen, $C_1-C_{12}$ alkyl, $C_1-C_{12}$ acyl or $>NR_{16}$ is a $C_1-C_{12}$ alkyl N-oxide; and the dideoxy azapyranose contains at least two hydroxyl groups.

Because the 1,6-dideoxy azapyranose lacks hydroxyl groups at the 1- and 6-position carbon atoms, formed oligosaccharides are disaccharides with the dideoxy azapyranose at the reducing end, which azapyranose is linked to the saccharide at the non-reducing end (ring A) through a glycosidic bond at $R_1$, $R_2$ or $R_5$.

It is preferred that the oligosaccharide compounds of this invention have a particular spatial orientation. The preferred spatial orientation for the oligosaccharide corresponding to Formula II above is beta, and is shown below in Formula IV

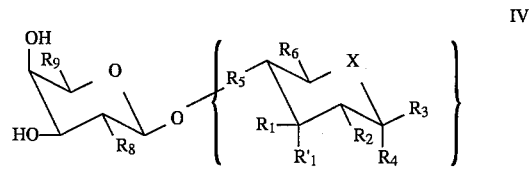

IV wherein groups X, and $R_{1-9}$ are the same as defined for Formula II above.

Another preferred embodiment includes a compound of Formula I in which both the A and C rings are joined to the B ring of the formula. Here, $R_1$ and $R_5$ are both absent and are replaced by glycosyl-linked saccharides. A general structural formula for such compounds is shown as structural Formula V,

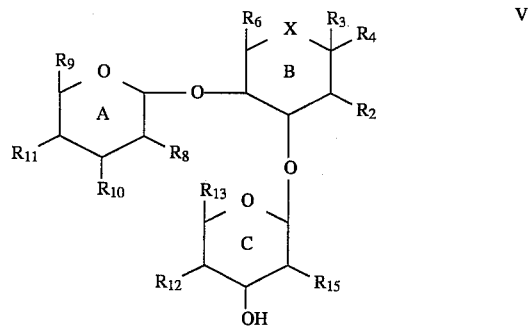

V wherein the various $R_{1-15}$ groups present and X are as defined before.

In a preferred embodiment, ring C is an e-linked fucosyl group and ring A is a β-linked galactosyl group (Gal). In one such particularly preferred embodiment, X is S, $R_2$ is hydroxyl and $R_3$ and $R_4$ are hydrogen and hydroxyl, $R_6$ is hydroxymethyl, and ring B has a glucose configuration.

In another particularly preferred embodiment, ring C is an α-linked fucosyl group and rings A and B are β1,4-linked N-acetyl-glucosamines $(GlcNAc)_2$. In yet other embodiments, ring C is α-linked fucosyl and rings A and B are galactosylβ1,3-N-acetylglucosamine (Galβ1,3-GlcNAc) or ring C is α-linked fucosyl with rings A and B being galactosylβ1,4-N-acetylgalactosamine (Galβ1,4-NAcGal).

The Synthetic Methods

A. Glycosyltransferase Methods

1. Procedures

Another aspect of the present invention relates to a glycosylation method. In accordance with the glycosylation method, an activated donor monosaccharide is admixed in an aqueous medium with an acceptor saccharide of Formula II or III below in the presence of a catalytic amount of a glycosyltransferase having specificity for both the activated donor monosaccharide and the acceptor saccharide to form a reaction mixture:

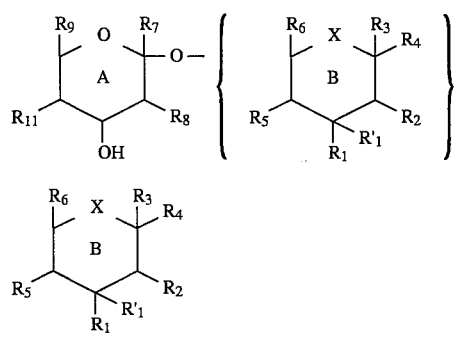

wherein X, $R_1$, $R_1'$, $R_2$, $R_3$, $R_4$, $R_5$ and $R_6$ ($R_{1-6}$) are as defined in Formula II, and the reaction mixture is maintained for a time period and under conditions sufficient for the acceptor saccharide to be glycosylated and form a glycosylated acceptor saccharide.

As used herein, the phrase "activated donor monosaccharide" means a donor monosaccharide bonded to an activating nucleotide. Exemplary donor monosaccharides include Glc, GlcNAc, Gal, GalNAc, Man, Fuc, NeuAc and derivatives thereof such as Compounds 201–204 of Table 5 hereinafter. Activating nucleotides known in the art to have specificity for donor monosaccharides include uridine diphosphate (UDP), adenosine diphosphate (ADP), guanosine diphosphate (GDP), cytidine monophosphate (CMP) and cytidine diphosphate (CDP).

Where the donor monosaccharide is Glc, GlcNAc, Gal or GalNAc, a preferred activating nucleotide is UDP. Where the donor monosaccharide is Man or Fuc, a preferred activating nucleotide is GDP. Where the donor monosaccharide is NeuAc, a preferred activating nucleotide is CMP. Preferred activated donor monosaccharides for use in the method of the present invention are UDP-Gal, UDP-GalNAc, UDP-Glc, UDP-GlcNAc and CMP-NeuAc.

Activated donor monosaccharides can be obtained from commercial sources (Sigma Chem. Co., St. Louis, Mo.) or prepared from activating nucleotides and phosphorylated monosaccharides. Activated donor monosaccharides are prepared by reacting a phosphorylated donor monosaccharide with an activating nucleotide in the presence of a catalytic amount of a nucleotide-sugar-pyrophosphorylase, an enzyme that catalyzes the formation of activated donor monosaccharides.

The selection of a particular nucleotide-sugar-pyrophosphorylase depends upon the nature of the phosphorylated donor monosaccharide and the activating nucleotide used. Thus, for example, UDP-Glc pyrophophorylase catalyzes the formation of UDP-Glc from UTP and phosphorylated Glc. Other pyrophosphorylases are well known in the art and include CMP-NeuAc synthetase, which catalyzes the formation of CMP-NeuAc from CTP and NeuAc.

Nucleotide-sugar-pyrophosphorylases can be obtained from commercial sources, isolated from animal tissues or in recombinant form using standard techniques of genetic engineering, as is known.

The selection of an acceptor depends upon the desired structure of the oligosaccharide. Typically, the substituent configuration of the acceptor corresponds to the substituent nature of ring B of the oligosaccharide of Formulas I or II. The data presented below in Table 1 show the correspondence between particular acceptor saccharides and the synthesized oligosaccharide prepared using β1,4-galactosyltransferase (GalT). The reaction illustrated above in Table 1 exemplifies use of glucosyl derivatives (Compounds 1a–z) as acceptors. Additional numbered acceptors are illustrated below the table.

TABLE 1

UDP-Gal + 1(a–z) →(Gal T) 2(a–z)

| Compound | $R_1$ | $R_2$ | $R_3$ | $R_4$ | $R_{6'}$ | Relative Rate (%) |
|---|---|---|---|---|---|---|
| 1a | OH | AcNH | (H, | OH) | H | 100 |
| 1b | OH | AcNH | H | $CH_3O-$ | H | 75 |
| 1c | OH | AcNH | H | $CH_2=CHCH_2O-$ | H | 25 |
| 1d | $CH_3CHOCO_2$ | AcNH | (H | OH) | H | 0.6 |
| 1e | OH | AcNH | (H, | OH) | $CH_3CO-$ | 4 |
| 1f | AcO— | AcNH | (H, | OH) | H | 0.4 |
| 1g | $CH_2=CHCH_2O-$ | AcNH | H | OMe | H | 0 |
| 1h | $CH_3(CH_2)_2O-$ | AcNH | (H, | OH) | H | 0.5 |
| 1i | H | AcNH | $CH_2=CHCH_2O-$ | H | H | 1.0 |
| 1j | $CH_2=CHCH_2O-$ | AcNH | $CH_3(CH_2)_3O-$ | H | H | 0.3 |
| 1k | MeOCOO— | AcNH | $CH_2=CHCH_2O-$ | H | H | a |
| 1l | AllylOCOO— | AcNH | $CH_2=CHCH_2O-$ | H | H | a |

TABLE 1-continued

| | | | | | | |
|---|---|---|---|---|---|---|
| 1m | MeOCH₂O— | AcNH | CH₂=CHCH₂O— | H | H | 2.0 |
| 1n | O | AcNH | CH₃O— | H | H | 2.0 |
| 1o | epi-OH | AcNH | (H, | OH) | H | 0.04 |
| 1p | OH | AcNH | —SPh | H | H | 0 |
| 1q | O | AcNH | H | OMe | H | 0.1 |
| 1r | OH | Phthalimido | H | SPh | H | 0 |
| 1s | epi-OH | AcNH | H | OMe | H | 0 |
| 1t | OH | OH | (OH, | H) | H | 100 |
| 1u | CH₂=CHCH₂O— | OH | (OH, | H) | H | 0 |
| 1v | MeO— | OH | (OH, | H) | H | 10 |
| 1w | OH | OH | SPh | H | H | 0.1 |
| 1x | OH | OH | SPh | H | CH₂Ph | 0.04 |
| 1y | OH | H | (OH, | H) | H | 60 |
| 1z | OH | AcNH | CH₃O— | H | CH₃— | 20 |
| 3 | | | | | | 3 |
| 4 | | | | | | 0.1 |
| 5 | | | | | | 70 |
| 6 | | | | | | 0.4 |
| D-xylose | | | | | | 90 |
| (GlcNAc)ₙ | | | | | | |
| n = 2 | | | | | | 500 |
| n = 3 | | | | | | 60 |
| n = 4 | | | | | | 70 |

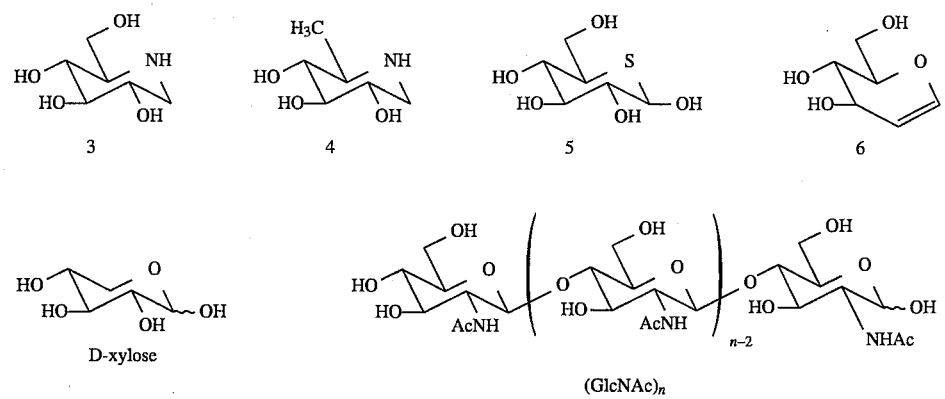

Reaction rates for Compounds 1b–1g are given in relative terms compared to Compound 1a (100 percent). Reaction rates for Compounds 1u–6, Xylose and GLcNAc polymers are given in relative terms compared to Compound 1t (100 percent). Parenthesized H, OH for $R_3$ and $R_4$ indicates that the stereochemistry for those groups is unassigned.
a indicates acyl migration.

The preparation of acceptor saccharides varies with the nature of such saccharides. Deoxy-azasugars are made by a chemical-enzymatic method based on an aldolase-catalyzed reaction and a reductive amination. According to such a method, an azido aldehyde and a phosphate donor substrate are reacted in the presence of a catalytic amount of an aldolase to form an azido-substituted-ketose phosphate. The azido-substituted-ketose phosphate is then reductively cyclized by hydrogenation in the presence of a standard palladium catalyst. The hydrogenation is carried out at greater than atmospheric pressure using a standard hydrogenation solvent such as water, ethanol or methanol or mixtures thereof.

Alternatively, the azido-substituted-ketose phosphate is dephosphorylated prior to hydrogenation. Where such dephosphorylation occurs, the resulting azasugar has a 1-deoxy configuration as compared to a 1,6-dideoxy configuration that results from hydrogenation without prior dephosphorylation.

The substituent configuration of the azasugar is determined by the configuration of the azido aldehyde. Modifications on the ring nitorgen atom are typically made after reductive cyclization. For example, a $C_1$–$C_{12}$ alkyl group can be added by reductive alkylation of a corresponding aldehyde or ketone. A leaving group-substituted alkane can also be used for the alkylation. Exemplary leaving groups include halides, methanesulfonyl (mesyl) and p-toluenesulfonyl (tosyl) groups. Methods of N-alkylation are well known in the art.

$C_1$–$C_{12}$ Acyl groups can be added via an appropriate anhydride or acid halide such as lauroyl chloride. Acylation methods are also well known.

N-Oxide derivatives are readily prepared from the N-alkyl derivatives by oxidation with hydrogen peroxide. An exemplary preparation is illustrated hereinafter.

Thiosugar acceptor saccharides such as thioglucose are available from commercial sources (Sigma Chemical Co., St. Louis, Mo.). Substituent configurations of the ring carbon atoms of such thiosugars are made using standard chemical techniques well known in the art. Oxidation of the ring S atom with $H_2O_2$ to sulfoxide (SO) and sulfone ($SO_2$) is carried out at room temperature. Protection of the anomeric center as methyl thioglycoside is required to prevent ring opening.

Acceptor monosaccharides that are derivatives of naturally occuring sugars are prepared using standard chemical techniques well known in the art. Exemplary preparations of acceptor saccharides are set forth hereinafter in Example 5.

Products prepared from the reactions illustrated in connection with Table 1 can also be acceptor substrates or inhibitors for further glycosyl transferase reactions, as can the acceptor substrates utilized in that table and other saccharides. Exemplary reactions and relative rates using such compounds are illustrated in Table 1a, below, wherein a disaccharide or monosaccharide reactant compound (acceptor substrate) has the same number as an acceptor or product compound of Table 1 [Compounds 1a, 1t, 2a, 2i, 2t, 3, 5, 6 and (GlcNAc)2] or a compound discussed elsewhere herein (Compound 7, 8 and 10a), and the transferase utilized was fucosyl α1,3/1,4 transferase (FucT; EC 2.4.1.65). Reactions such as those shown in Table 1a thus utilize compounds such as those shown by structural Formulas III and IV to prepare compounds such as those of structural Formulas I, II and V. An exemplary branched trisaccharide-forming reaction is shown above the table. The data of Table 1a are also reported in Dumas et al., *BioMed. Chem. Lett.*, 1:425–428 (1991), as are other data.

TABLE 1a

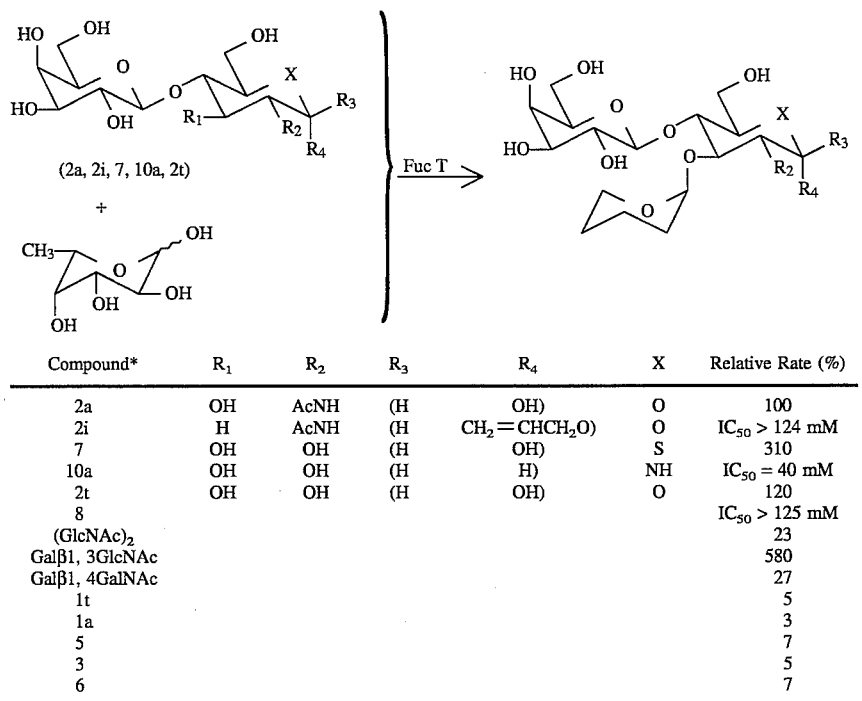

| Compound* | $R_1$ | $R_2$ | $R_3$ | $R_4$ | X | Relative Rate (%) |
|---|---|---|---|---|---|---|
| 2a | OH | AcNH | (H | OH) | O | 100 |
| 2i | H | AcNH | (H | $CH_2=CHCH_2O$) | O | $IC_{50} > 124$ mM |
| 7 | OH | OH | (H | OH) | S | 310 |
| 10a | OH | OH | (H | H) | NH | $IC_{50} = 40$ mM |
| 2t | OH | OH | (H | OH) | O | 120 |
| 8 | | | | | | $IC_{50} > 125$ mM |
| (GlcNAc)$_2$ | | | | | | 23 |
| Galβ1, 3GlcNAc | | | | | | 580 |
| Galβ1, 4GalNAc | | | | | | 27 |
| 1t | | | | | | 5 |
| 1a | | | | | | 3 |
| 5 | | | | | | 7 |
| 3 | | | | | | 5 |
| 6 | | | | | | 7 |

*Reactant compound (acceptor substrate)

Glycosyltransferase used in the glycosylation method has specificity both for the activated donor monosaccharide and the acceptor saccharide. That is, the glycosyltransferase is capable of transferring the activated donor monosaccharide to the acceptor saccharide and forming a glycosidically-linked oligosaccharide of a predetermined configuration.

Exemplary glycosyltransferases include those enzymes that catalyze the formation of the products in Table 2, below. See, also, Beyer et al., *Adv. Enzymol.*, 52:23–161 (1981). Further, as exemplified hereinafter, glycosyltransferases can utilize non-naturally occurring oligosaccharides.

TABLE 2

I. Sialyltransferase

Siaα2,6Gal

TABLE 2-continued

Siaα2,3Gal
Siaα2,6GalNAc
Siaα2,6GlcNAc
Siaα2,8Sia
Siaα2,4Gal
Siaα2,4GlcNAc
Siaα2,6Man

II. Fucosyltransferase

Fucα1,2Galβ
Fucα1,4GlcNAcβ
Fucα1,3GlcNAcβ
Fucα1,3Glc
Fucα1,6GlcNAcβ

TABLE 2-continued

Fucα1,6Galβ
Fucα1,3Galβ
Fucα1,3Fuc

III. Galactosyltransferase

Galβ1,4Glc
Galβ1,4GlcNAc
Galβ1,3GlcNAc
Galβ1,3diglyceride
Galβ1,6GlcNAc
Galβ1,3GalNAc
Galβ1,6GalNAc
Galα1,3GalNAc
Galα1,3Gal
Galα1,4Gal
Galβ1,4Gal
Galβ1,6Gal TABLE 2-continued Galβ1,4Xyl IV. N-Acetylgalactosaminyltransferase GalNAcα1,3Galβ
GalNAcβ1,4Gal
Iduronic Acid
GalNAcβ1,3Gal
GalNAcα1,3GalNAc
(GalNAcβ1,4GluUAβ1,3)$_n$
(GalNAcβ1,4IdUAα1,3)$_n$ V. N-Acetylglucosaminyltransferase GlcNAcβ1,4GlcNAc
GlcNAcβ1,2Man
GlcNAcβ1,4Man
GlcNAcβ1,6Man
GlcNAcβ1,3Man
GlcNAcβ1,3Gal
GlcNAcβ1,4Gal
GlcNAcβ1,6Gal
GlcNAcα1,4Gal
GlcNAcα1,4GlcNAc
GlcNAcβ1,6GalNAc
GlcNAcβ1,3GalNAc
GlcNAcβ1,4GlcUA
GlcNAcα1,4GlcUA
GlcNAcα1,4IdUA Glycosyltransferases can be obtained from commercial sources (Sigma Chem. Co., St. Louis, Mo.; Boehringer Mannheim, Indianapolis, Ind. and Genzyme, Cambridge, Mass.), isolated and purified from microbial, plant or animal tissues or in recombinant form using well known techniques of genetic engineering.

As used herein, the phrase "catalytic amount" means that amount of an enzyme at least sufficient to catalyze, in a non-rate limiting manner, the conversion of that enzyme's substrate to product.

The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

Admixing comprises mixing each ingredient with each of the other ingredients in a suitable aqueous medium (solvent) to form a reaction mixture. The reaction mixture is maintained under biological reaction conditions of temperature, pH, solvent osmolality, ionic composition and ambient atmosphere for a period of time sufficient to glycosylate the acceptor saccharide and form a glycosylated acceptor saccharide.

Temperature can range from about 15° C. to about 40° C. Preferably temperature is from about 20° C. to about 40° C. and, more preferably from about 25° C. to about 37° C.

The pH value can range from about 6.0 to about 11.0. Preferably, the pH value is from about 6.5 to about 8.5 and, more preferably about 7.0 to about 7.5. The pH value is maintained by buffers in the aqueous solvent. The buffer is devoid of chelators that bind enzyme cofactors such as $Mg^{+2}$ or $Mn^{+2}$. The selection of a buffer is based on the ability of the buffer to maintain pH value at the desired level. Where the pH value is about 7.5, a preferred buffer is HEPES.

The osmolality and ionic composition of the aqueous solvent are designed and selected to solubilize the ingredients of the reaction mixture and to provide cofactors for the enzymes contained in the reaction mixture. The osmolality of the aqueous solvent including the buffer is preferably from about 100 mOsm to about 300 mOsm.

The reaction time and conditions for the synthesis of an oligosaccharide vary with the nature of the monosaccharide acceptor. Where the monosaccharide derivative is Compound 5 from Table 1, the reaction time is about 48 hours and the reaction occurs in a buffered aqueous solution at a temperature of about 37° C. (Example 1A). When the monosaccharide acceptor is Compound be or 1i from Table 1, the reaction time is about 96 hours at the same temperature (Examples 1B and 1C).

Under certain circumstances, when the monosaccharide acceptor has a hydrogen or a hydroxyl group in an e-orientation at the carbon atom at position 2 (i.e., $R_2$ is hydrogen or hydroxyl in Formula III), the reaction conditions include lactalbumin and, preferably α-lactalbumin.

It is noted that the synthetic method of the present invention does not provide any 3-O-acyl oligosaccharides prepared with GalT. When 3-O-acyl monosaccharide acceptors are used, the formed product is a 6-O-acylated oligosaccharide. For example, when 3-O-acetyl-N-acetylglucosamine was used as the monosaccharide acceptor, Compound 2e from Table 1 was obtained indicating a migration of the acetyl group to position 6 of the N-acetylglucosamine moiety. No other byproduct was obtained.

In addition to the acetyl group, methoxycarbonyl, chloroacetyl, and allyloxycarbonyl groups also showed 3→6 0-acyl migration. The half-life for each of these migrations was about three hours for acetyl, methoxycarbonyl, and allyloxycarbonyl group, and less than three hours for the chloroacetyl group at room temperature and pH 7.0 as measured by NMR.

The synthesis of 3-O-acyl-GlcNAc is straightforward. Starting from the readily available 4,6-O-benzylidene derivative, various acyl group can be introduced to the 3-0 position.

To further study this unexpected acyl migration, 3-O-acetyl-N-acetylglucosamine was incubated at pH 7.0 in the absence of the GalT enzyme and a $^1$H-NMR spectrum was taken. It was observed that the intensity of a new peak at 1.82 ppm increased while the signal at 1.90 ppm ($CH_3CONH$-) decreased, and a downfield shift of H-6 and upfield shift of H-3 were observed at the same time. After 24 hours, 90 percent of the original compound was converted to the new product which was identical to an authentic 6-O-methoxycarbonyl-N-acetylglucosamine prepared separately. The identity was further confirmed by the high-resolution mass spectroscopy analysis.

6-O-Acetyl-N-acetylglucosamine was then studied as a substrate for GalT and it was found to be about 10 times as effective as the 3-O-acyl isomer under the same conditions. A separate synthesis of the 6-O-acetyl disaccharide was then accomplished in 70 percent isolated yield with the use of 6-O-acetyl-N-acetylglucosamine as a substrate. It is worth noting that 6-O-acetyl-N-acetylglucosamine was easily prepared in 82 percent yield from GlcNAc and isopropenyl acetate in anhydrous dimethylformamide catalyzed by subtilisin.

The reaction rate and yield of the glycosylation method can be enhanced by providing for the in situ regeneration of activated donor monosaccharide.

In a preferred embodiment, the glycosylation method comprises the steps of:

(a) admixing in the presence of each other in an aqueous medium (i) an acceptor saccharide;

(ii) a donor monosaccharide;

(iii) an activating nucleotide having specificity for the donor monosaccharide;

(iv) an activated donor monosaccharide regenerating system;

(v) a pyrophosphate scavenger; and (vi) catalytic amounts of a glycosyltransferase having specificity for both the activated form of the donor monosaccharide and the acceptor saccharide and a nucleotide-sugar-pyrophosphorylase having specificity for both the donor monosaccharide and the activating nucleotide to form a reaction mixture; and (b) maintaining the reaction mixture for a time period and under conditions sufficient for the acceptor saccharide to be glycosylated and form a glycosylated acceptor saccharide.

The donor monosaccharides, activating nucleotides, glycosyltransferases and nucleotide-sugar-pyrophosphorylases used in this preferred method are the same as set forth above.

The activated donor monosaccharide regenerating system comprises a phosphate donor and a catalytic amount of a kinase that catalyzes the transfer of phosphate from the phosphate donor to an activating nucleotide.

The phosphate donor of the regenerating system is a phosphorylated compound, the phosphate group of which can be used to phosphorylate a nucleoside diphosphate such as ADP or CDP. The only limitation on the selection of a phosphate donor is that neither the phosphorylated nor the dephosphorylated forms of the phosphate donor can substantially interfere with any of the reactions involved in the formation of the glycosylated acceptor saccharide. Preferred phosphate donors are phosphoenolpyruvate (PEP) and acetyl phosphate. A particularly preferred phosphate donor is PEP.

The selection of a particular kinase for use in accordance with the present invention depends upon the phosphate donor employed. When acetyl phosphate is used as the phosphate donor, the kinase is acetyl kinase. When PEP is used as the phosphate donor, the kinase is pyruvate kinase.

Other kinases can be employed with other phosphate donors as is well known to those of skill in the art. Kinases are commercially available (Sigma Chem. Co., St. Louis, Mo.; Boehringer Mannheim, Indianapolis, Ind.).

As used herein, the term "pyrophosphate scavenger" refers to substances that serve to remove inorganic pyrophosphate from a reaction mixture of the present invention. Inorganic pyrophosphate (PPi) is a byproduct of some activated donor monosaccharides.

Produced PPi can feed back to inhibit other enzymes such that glycosylation is reduced. However, PPi can be removed by metabolic means such as catabolism or by physical means such as sequestration by a PPi binding substance. Preferably, PPi is removed by metabolic means using inorganic pyrophosphatase, a commercially available PPi catabolic enzyme (Sigma Chem. Co., St. Louis, Mo.; Boehringer Mannheim, Indianapolis, Ind.), and that or a similar enzyme serves as the pyrophosphate scavenger.

The acceptor saccharide used in the preferred glycosylation method can be an acceptor monosaccharide, such as defined by structural Formula III, a naturally occurring mono- or oligosaccharide, or an oligosaccharide having structural Formula II, or more specifically, structural Formula IV.

By way of example, an oligosaccharide, such as a sialylated glycosyl compound, can be synthesized with the in situ regeneration of CMP-sialic acid according to Scheme 1 below, that is also referred to as cycle A hereinafter. Such a synthesis results in a linear oligosaccharide in which ring C of structural Formula I is linked to ring A, and ring A is linked to ring B.

A compound such as one of Compounds 201–204 that are illustrated hereinafter in Table 5 can be utilized in place of NeuAc. Use of such compounds provides compounds of structural Formulas I, II and IV having 3-substituted-1,2-dihydroxypropyl groups.

Scheme 1
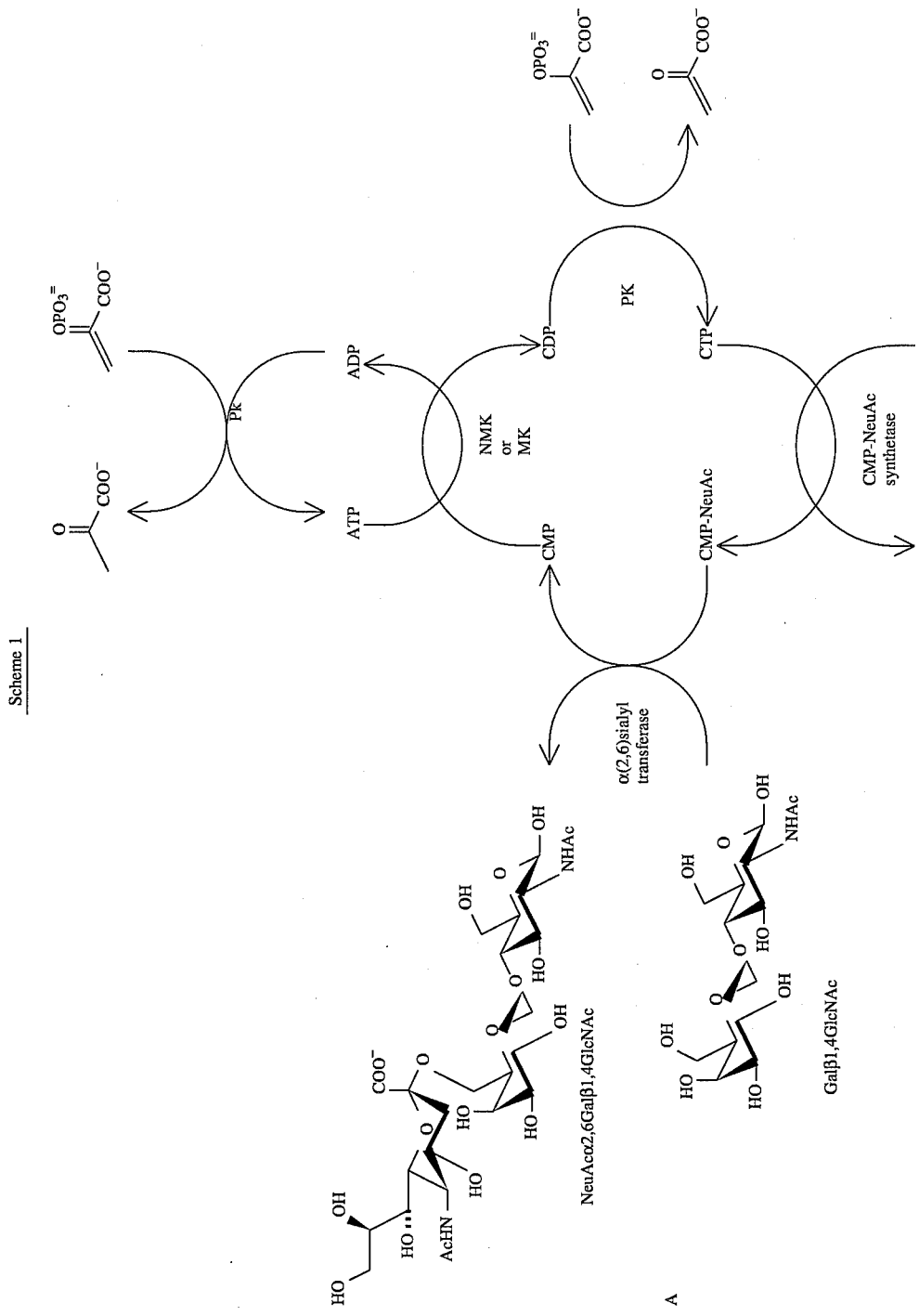

-continued
Scheme 1
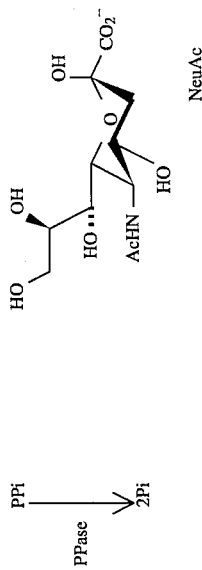

According to Scheme 1, CMP is converted to CDP catalyzed by nucleoside monophosphate kinase (NMK) in the presence of ATP, which is regenerated from its byproduct ADP catalyzed by pyruvate kinase (PK) in the presence of phosphoenolypyruvate (PEP). CDP is further converted to CTP with PEP catalyzed by PK. CTP reacts with NeuAc catalyzed by CMP-NeuAc synthetase to produce CMP-NeuAc. The byproduct inorganic pyrophosphate is scavenged by pyrophosphatase (PPase). Sialylation of Galβ1,4GlcNAc is accomplished by CMP-NeuAc and Siaα2,6Gal sialyltransferase. The released CMP is again converted to CDP, to CTP and to CMP-NeuAc.

In accordance with such a method, therefore, there are reacted: a sialic acid such as N-acetylneuraminic acid (NeuAc) as the donor monosaccharide; a Galβ1,4GlcNAc (N-acetyllactosamine; LacNAc) as the acceptor disaccharide; a CMP-sialic acid regenerating system as the activated donor monosaccharide regenerating system; a pyrophosphate scavenger such as inorganic pyrophosphotase, and catalytic amounts of a CMP-sialic acid synthetase as the nucleotide-sugar-pyrophosphorylase and a sialyltransferase as the glycosyltransferase having substrate specificity for the acceptor saccharide.

As used herein, the term "a sialic acid" means neuraminic acid (5-amino-3,5-dideoxy-D-glycero-D-galacto- 2-nonulosonic acid), and derivatives such as an N- or O-acetyl derivative of neuraminic acid. Preferably, the sialic acid is an N-acetyl derivative of neuraminic acid (NeuAc), which has been reported as a naturally occurring sialic acid in various animal species. Schauer, *Adv. Carbohydr. Chem. Biochem.*, 40:131 (1982).

A sialic acid derivative can be substituted at the carbon atom at positions 4, 5, 7, 8 or 9 of the sialic acid as herein defined. Exemplary derivatives at the above positions include a fluoro or deoxy group at positions 5, 7, 8 or 9, an $C_1$–$C_3$ acyl or amino acyl of an amino from an amino acid, and phosphoryl. Positions 5 or 9 can also be substituted with an azido group. Particularly preferred sialic acids are NeuAc, N-lactylneuraminic acid, 9-O-acetyl-NeuAc, 9-deoxy-9-fluoro-NeuAc, and 9-azido-9-deoxy-NeuAc. A sialic acid used in accordance with the present invention can be obtained commercially (Sigma Chemical Company, St. Louis, Mo.) or isolated from various animal tissues. Schauer et al., Biochem. Soc. Symp., 40:87 (1974).

As used herein, the term "a glycosyl compound" refers to an organic compound having one or more glycosyl residues. Preferred glycosyl residues are Gal, GlcNAc, GalNAc, NeuAcGalβ1,4GlcNAc. The glycosyl residue acts as the acceptor for the sialic acid, and therefore must have an appropriate hydroxyl group available to accept the sialic acid group.

The CMP-sialic acid regenerating system used in the present invention comprises cytidine monophosphate (CMP), a nucleoside triphosphate, a phosphate donor, a kinase capable of transferring phosphate from the phosphate donor to nucleoside diphosphates and a nucleoside monophosphate kinase capable of transferring the terminal phosphate from a nucleoside triphosphate to CMP.

Nucleoside triphosphates suitable for use in accordance with the CMP-sialic acid regenerating system are adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is ATP.

Nucleoside monophosphate kinases are enzymes that catalyze the phosphorylation of nucleoside monophosphates. Nucleoside monophosphate kinase (NMK) and myokinase (MK) used in accordance with the CMP-sialic acid regenerating system of the present invention are used to catalyze the phosphorylation of CMP. NMK's are commercially available (Sigma Chem. Co., St. Louis, Mo.; Boehringer Mannheim, Indianapolis, Ind.).

Because of the self-contained and cyclic character of this glycosylation method, once all the reactants and enzymes are present, the reaction continues until the first of the phosphate donor, donor monosaccharide or acceptor saccharide is consumed.

Thus, in the sialylation example, CMP is converted to CDP, whose conversion is catalyzed by nucleoside monophosphate kinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form PPi and CMP-sialic acid, the latter reaction being catalyzed by CMP-sialic acid synthetase. Following sialylation of the glycosyl compound, the released CMP re-enters the regenerating system to reform CDP, CTP and CMP-sialic acid. The formed PPi is scavenged as discussed before, and forms inorganic phosphate (Pi) as a byproduct. Pyruvate (PYR) is also a byproduct.

The concentration or amount of the various reactants used in the glycosylation method of the present invention depend upon numerous factors including reaction conditions such as temperature and pH value, and the amount of acceptor saccharide to be glycosylated. Because the glycosylation method of the present invention permits regeneration of activating nucleotides and activated donor monosaccharides and scavenging of produced PPi in the presence of catalytic amounts of the enzymes, the method is limited by the concentrations or amounts of donor monosaccharide, phosphate donor and acceptor saccharide. The upper limit for the concentrations of reactants that can be used in accordance with the method of the present invention is determined by the solubility of such reactants.

In a preferred embodiment, glycosylation is limited by the concentration of donor monosaccharide. According to such an embodiment, the concentrations of activating nucleotides, phosphate donor, acceptor saccharide and enzymes are selected such that glycosylation proceeds until the donor monosaccharide is consumed.

By way of example, when the concentration of sialic acid is about 20 mM, preferred concentrations of the other non-enzyme reactants are about 20 mM for the glycosyl compound, about 20–200 μM for CMP, about 2–20 μM for the nucleoside triphosphate and about 40 mM for the phosphate donor. Thus, the ratio of the concentration of these reactants to the concentration of sialic acid is preferrably about 0.01–0.1:1 for the glycosyl compound, about 0.001–0.01:1 for CMP, about 0.001–0.01:1 for the nucleoside triphosphate and about 2:1 for the phosphate donor.

The glycosylation method further comprises isolating the glycosylated acceptor saccharide. Isolation comprises recovering the glycosylated acceptor saccharide from the reaction mixture. Means for recovering the glycosylated acceptor saccharide include gel filtration, column chromatography, paper chromatography, affinity chromatography, extraction, precipitation and the like.

In a preferred embodiment, isolation is accomplished by lyophilizing the reaction mixture to reduce the volume of the reaction mixture, applying the lyophilized reaction mixture to a gel filtration column of about 200–400 mesh and eluting the sialylated glycosyl compound from the filtration column. Where such an embodiment is used to isolate sialylated glycosyl compounds, such compounds can be recovered with a yield of about 97 percent (see Example 2).

Where the acceptor saccharide is an acceptor oligosaccharide, such an acceptor oligosaccharide can itself be prepared in the reaction mixture of the glycosylation method. In such an embodiment, the reaction mixture futher includes:

(a) a second acceptor saccharide;

(b) a second donor monosaccharide;

(c) a second activating nucleotide that has specificity for the second donor monosaccharide;

(d) a second activated donor monosaccharide regenerating system; and (e) catalytic amounts of (i) a second glycosylatransferase having specificity for both the activated form of the second donor monosaccharide and the second acceptor saccharide and (ii) a second nucleotide-sugar-pyrophosphorylase having specificity for both the second donor monosaccharide and the second activating nucleotide.

The second acceptor saccharide can also be an acceptor oligosaccharide. The second glycosyltransferase is pareferably selected from the group of enzymes set forth above in Table 2.

The second donor monosaccharide, second activating nucleotide, second glycosyltransferase and second nucleotide-sugar-pyrophosphorylase can be the same as or different from the donor monosaccharide, activating nucleotide, glycosyltransferase and nucleotide-sugar-pyrophosphorylase set forth above.

Further, the second activated donor monosaccharide regeneration system can be wholly or in part identical to the activated donor monosaccharide regeneration system set forth above.

By way of example, the acceptor saccharide (Galβ1, 4GlcNAc; LacNAc) of the sialylation method of Scheme 1 above can be prepared in the same reaction mixture as illustrated below in Scheme 2, wherein dotted lines and the letters A, B and C are used to separate and identify the three reaction cycles that take place within a single aqueous reaction mixture in a single vessel. This synthesis also results in formation of a linear oligosaccharide in which ring A is linked to each of rings B and C.

Scheme 2
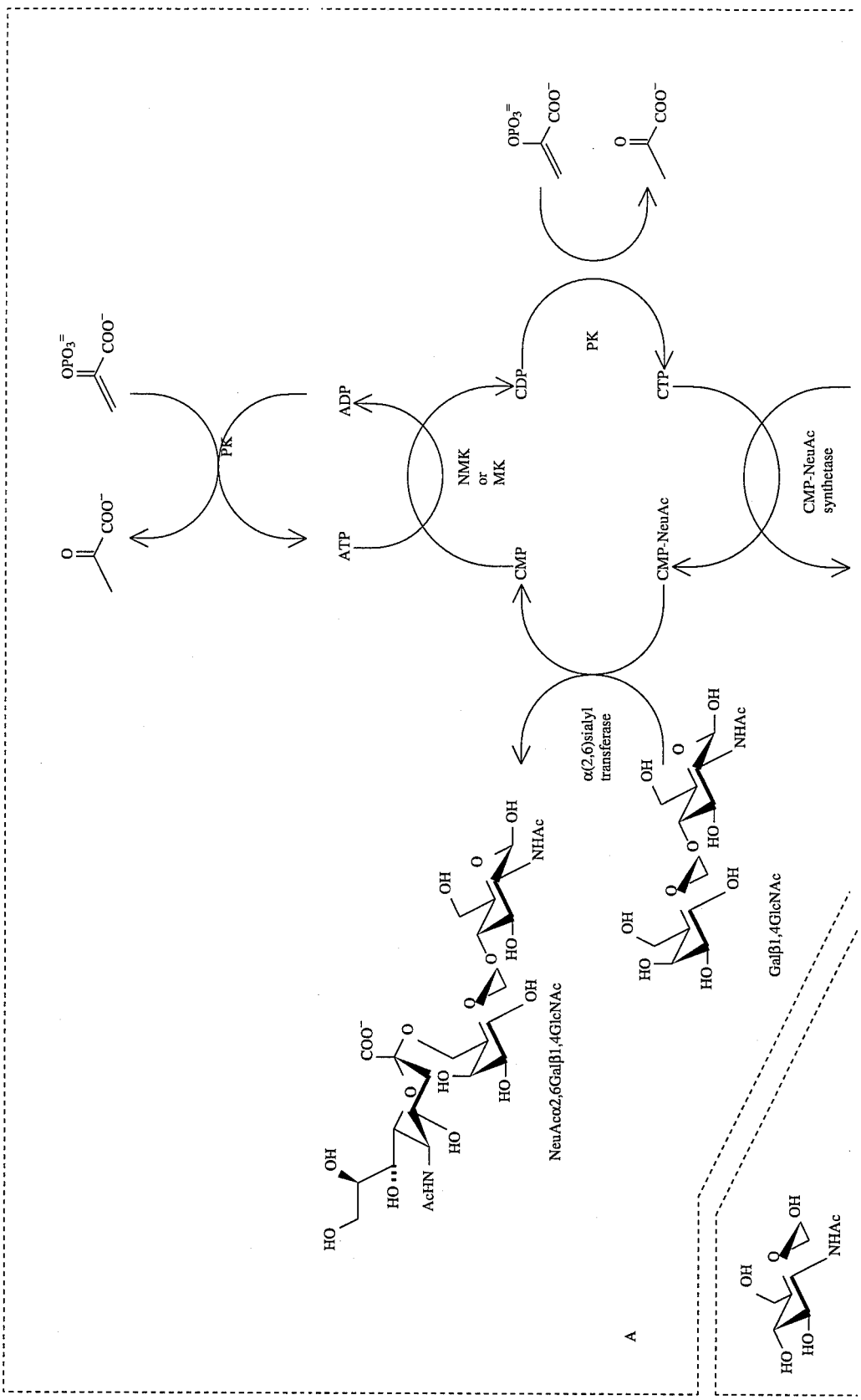

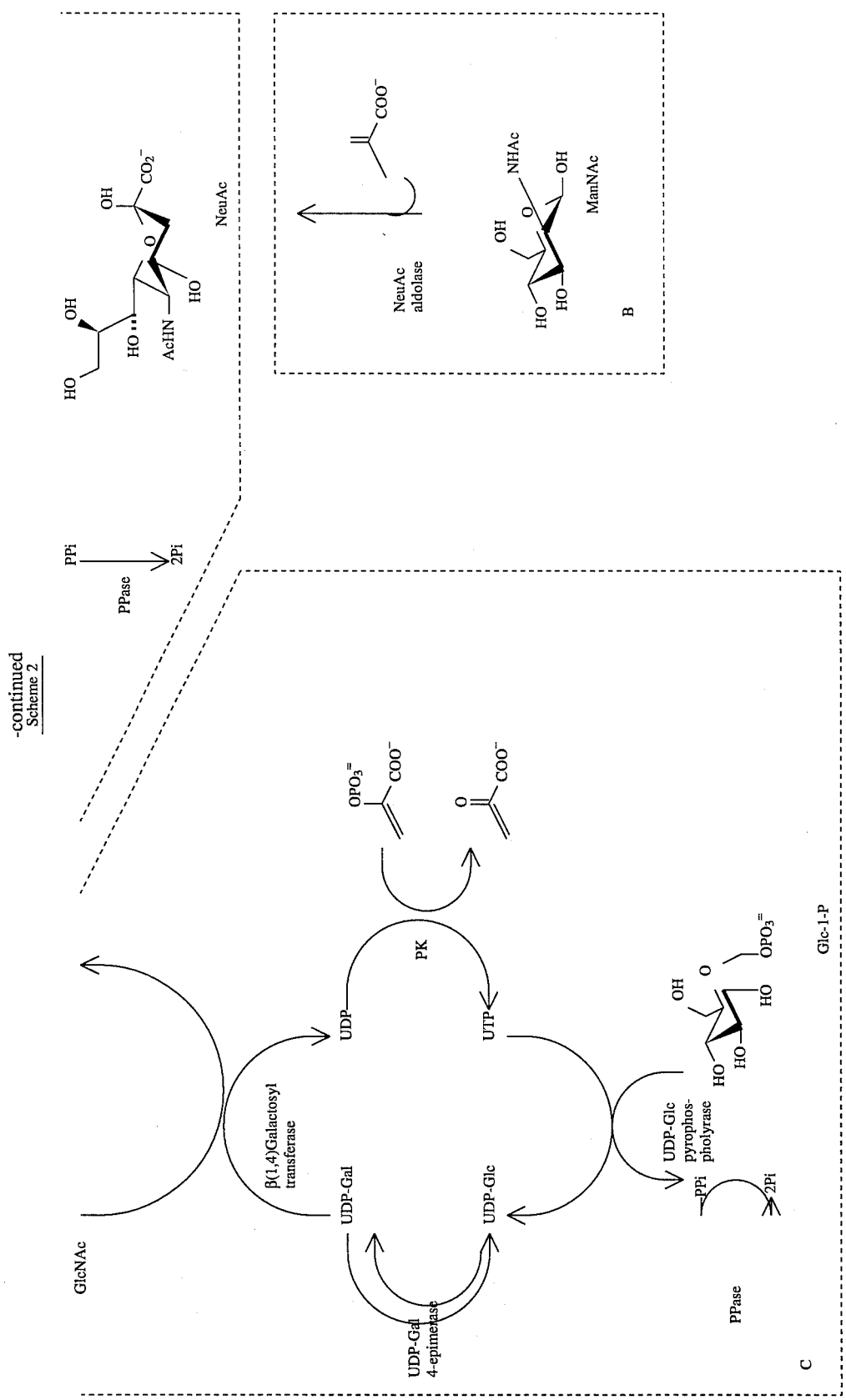

The preparation of LacNAc by cycle C in Scheme 2 is combined with the above-mentioned sialylation method (A + B in Scheme 2).

As indicated in Scheme 2, the components of cycle C included in the reaction mixture are a second donor monosaccharide (Gal), a second acceptor saccharide (GlcNAc), a second activating nucleotide (UDP), a second activated donor monosaccharide regenerating system (a phosphate donor-PEP; a Kinase-PK), which is identical to part of the activated donor monosaccharide regenerating system of Scheme 1 (cycle A), a second glycosyltransferase (β1,4galactosyltransferase) and a second nucleotide-sugar-pyrophosphorylase (UDP-Glc pyrophosphorylase).

In Scheme 2, the activated second donor monosaccharide (UDP-Gal) is prepared from the epimerase-catalyzed conversion of UDP-Glc, which is in turn synthesized from UTP and glucose 1-phosphate (Glc-i-P). Such a modification of the generation of the activated galactose (UDP-Gal) represents a still further embodiment of the glycosylation method.

A still further embodiment comprises the generation of sialic acid (NeuAc) from ManNAc (cycle B, Scheme 2).

An enzymatic aldol reaction (B in Scheme 2) is first introduced to the Scheme 1: ManNAc is converted to NeuAc catalyzed by NeuAc aldolase (EC 4.1.3.3) in the presence of pyruvic acid. Although NeuAc aldolase also catalyzes the reverse reaction (NeuAc to ManNAc and pyruvate), the produced NeuAc is irreversibly incorporated into cycle A via CMP-NeuAc catalyzed by CMP-sialic acid synthetase coupled with inorganic pyrophosphatase (PPase)-catalyzed decomposition of the released inorganic pyrophosphate. The sialyl LacNAc is obtained after a Bio-Gel P-2 column chromatography.

Details of the method illustrated in Scheme 2 are provided in Example 3.

The glycosylated acceptor saccharide can, in turn, serve as an acceptor saccharide for additional glycosylation reactions. For example, the sialyl LacNAc produced in accordance with Scheme 2 can be further glycosylated as illustrated below in Scheme 3 to form sialyl $Le^x$, wherein dotted lines and capatalized A-D are as described previously. This synthesis results in a branched oligosaccharide in which each of rings A and C is linked to ring B, which here is a disaccharide.

Scheme 3
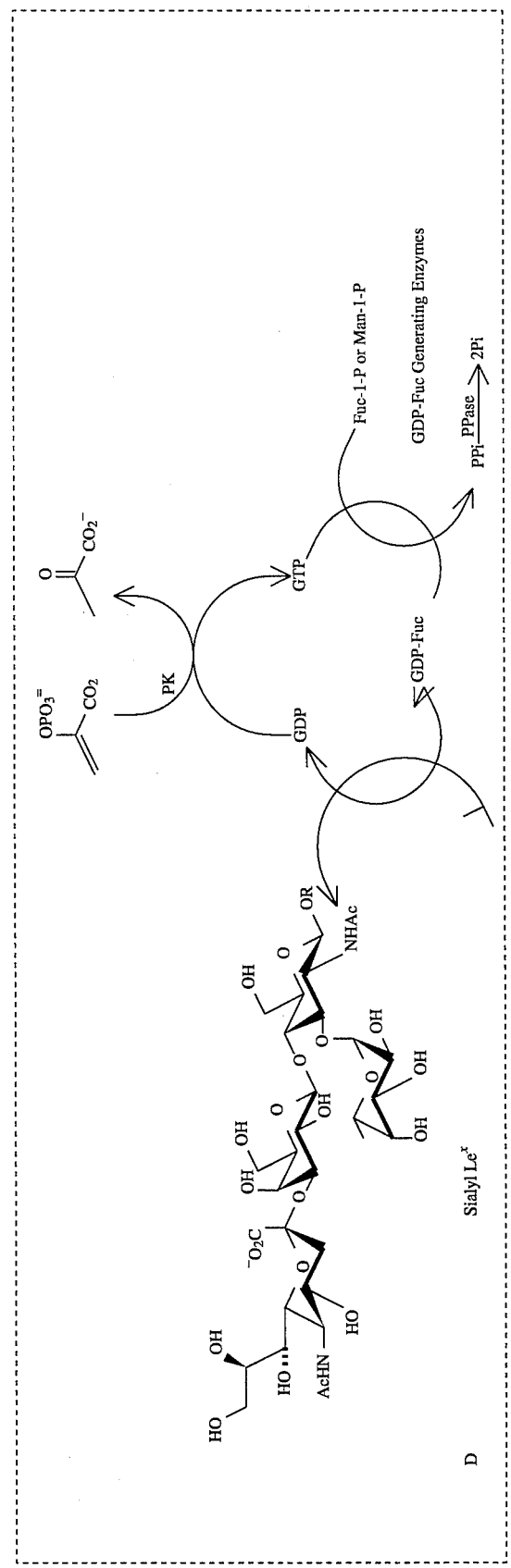

-continued
Scheme 3
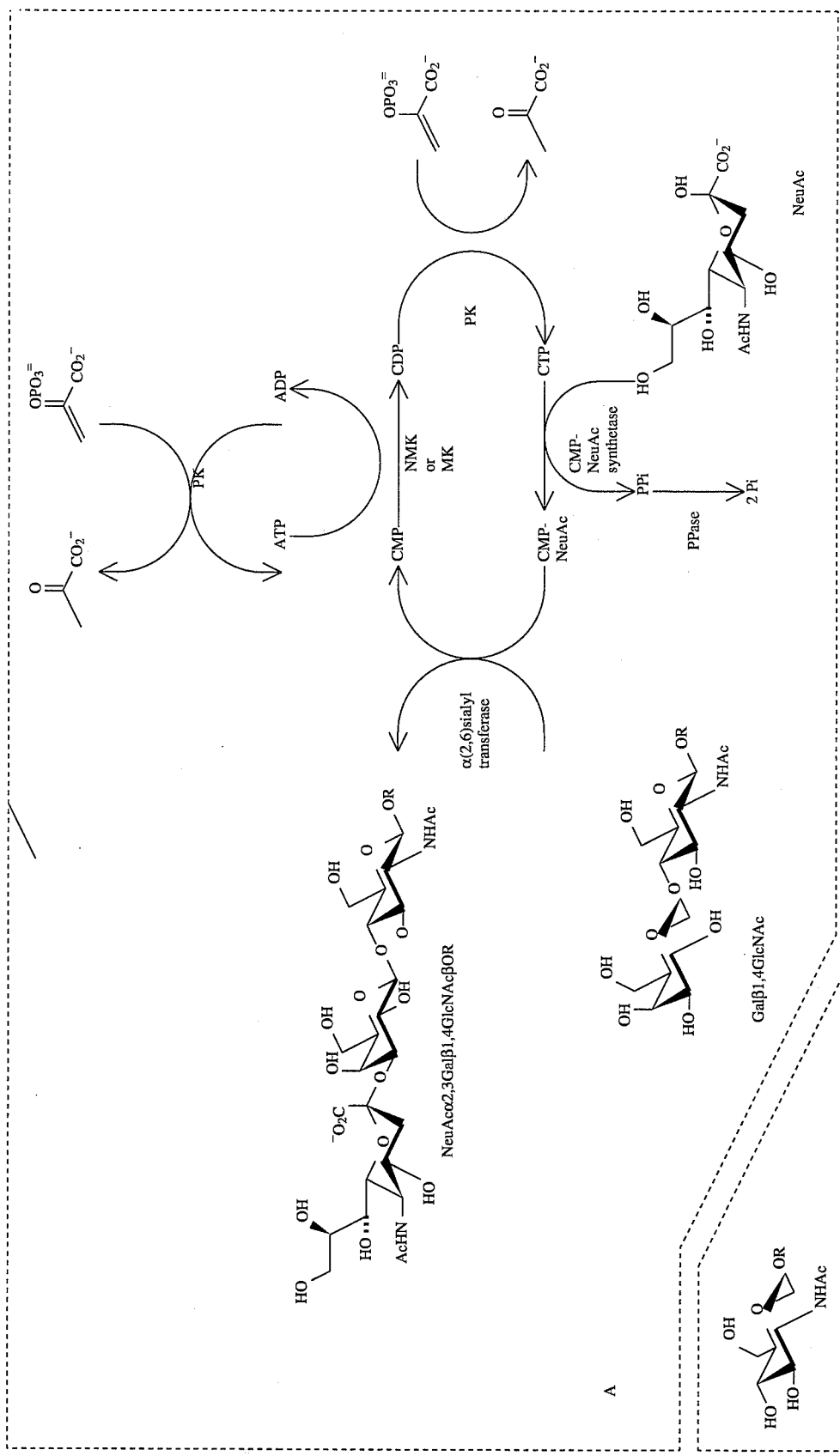

-continued
Scheme 3
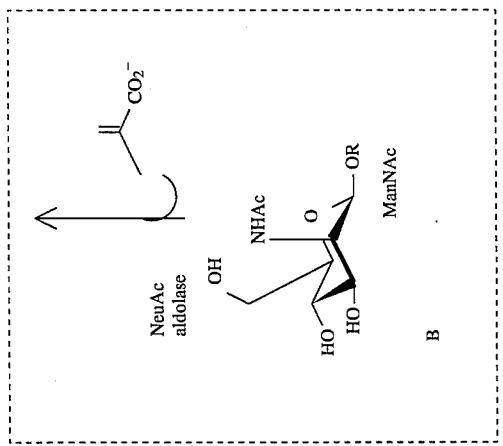
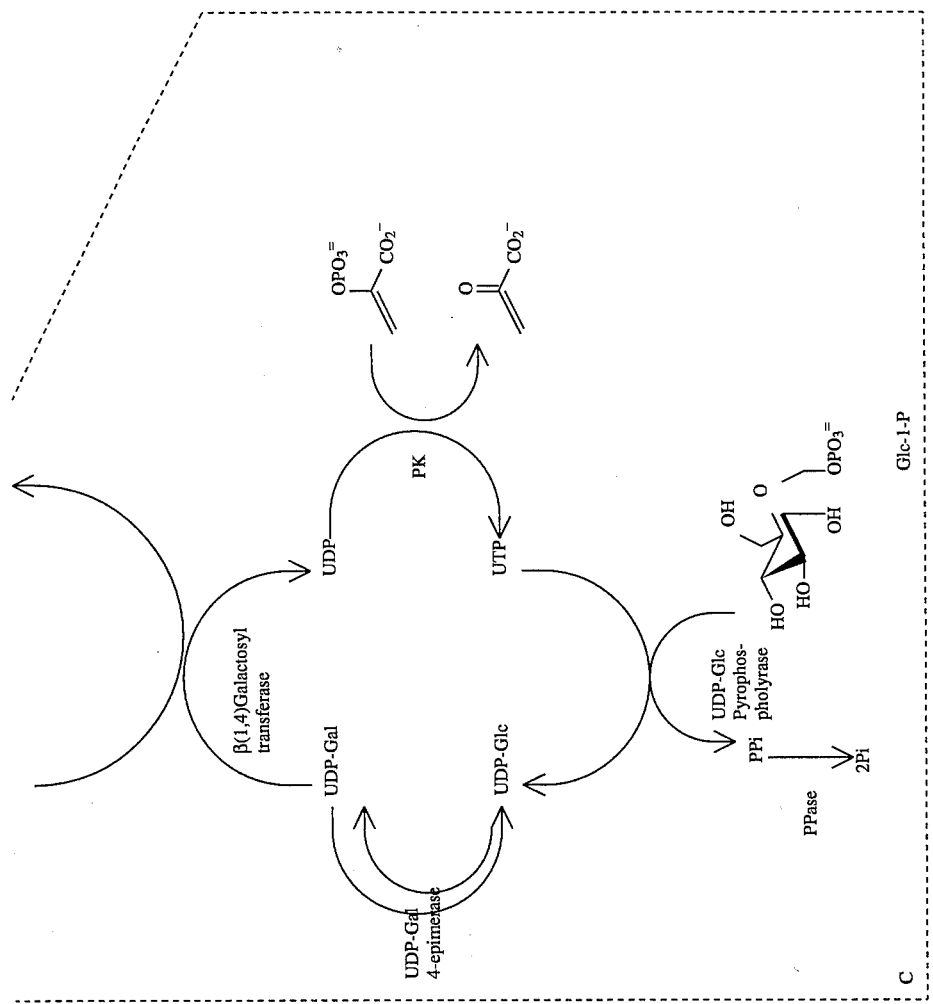

According to such a further glycosylation (cycle D, Scheme 3), sialyl LacNAc serves as an acceptor saccharide in the reaction mixture of Scheme 2, further comprising α1,3 fucosyltransferase, fucose 1-phosphate (Fuc-1-P), GTP and GDP-Fuc pyrophosphorylase.

All of the above reactions, as exemplified in Scheme 3, can proceed in the presence of one another (i.e., the same reaction vessel) because of the unique specificity of the glycosyltransferase and pyrophosphorylase enzymes employed. For example, Gal is not transferred to any other acceptor saccharide than GlcNAc because the β1,4 galactosyltransferase enzyme used does not have specificity for such other acceptor saccharides. Thus, a unique oligosaccharide can be designed and synthesized in accordance with the glycosylation method of the present invention by selecting and using specific enzymes.

2. Components (a) Acceptor Saccharides

As set forth above, an acceptor saccharide can be an aza sugar, such as a deoxy-aza sugar. The synthesis of several dideoxy-azasugars and their derivatives began with the aldol condensation of (RS)3-azido- 2-hydroxypropanal and DHAP catalyzed by FDP aldolase, rhamnulose-1-phosphate aldolase, or fuculose- 1-phosphate aldolase, or (RS)3-azido-2-hydroxypropanal plus acetaldehyde, acetone, or propionaldehyde, in the case of DERA. (RS)3-Azido-2-hydroxypropanal is prepared by the acid hydrolysis of 3-azido-2-hydroxypropanal diethyl acetal as described in Durrwachter et al., *J. Org. Chem.*, 53:4175 (1988). The addition of one of the above-mentioned aldolases to (RS)3-azido-2-hydroxypropanal plus DHAP provided Compounds 101, 104 or 108 as are shown on the left side of Scheme 4, below. Both rhamnulose-1-phosphate aldolase and fuculose-1-phosphate aldolase accept the (S)-aldehyde as substrate, whereas FDP-aldolase is selective for the (R)-enantiomer [Pederson et al., *Tetrahedron Lett.*, 29; 645 (1988)].

Palladium (Pd)-mediated reductive amination of phosphorylated Compounds 104 and 108 gave Compounds 106, 109 and 110 (at about a 1:1 ratio) respectively, each in approximately 90 percent total yield. In the same manner, the phosphorylated Compound 101c was hydrogenated directly to Compound 103c, also in high yield. These products are shown on the right side of Scheme 4.

Scheme 4

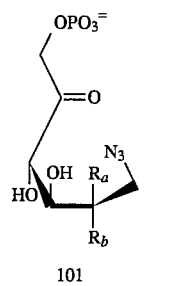

101

FDP Aldolase Product

-continued
Scheme 4

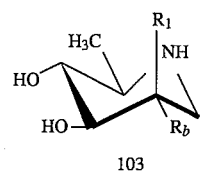

103 a: $R_a$ = OH, $R_b$ = H
b: $R_a$ = AcNH, $R_b$ = H
c: $R_a$ = H, $R_b$ = OH
d: $R_a$ = H, $R_b$ = AcNH
e: $R_a$ = F, $R_b$ = H
f: $R_a$ = OEt, $R_b$ = H

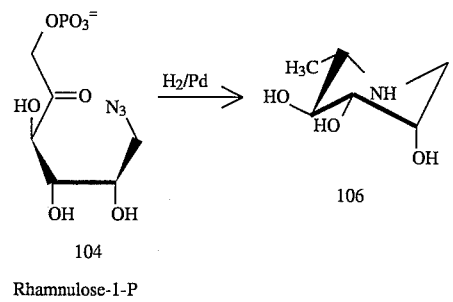

104
Rhamnulose-1-P
Aldolase Product

106

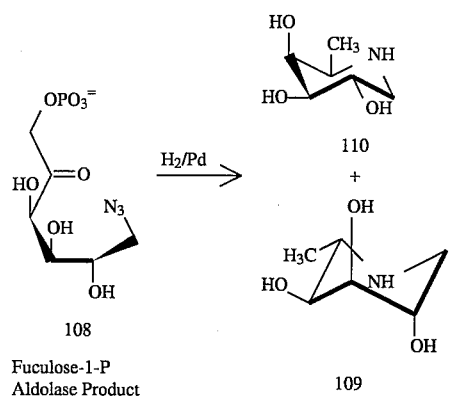

108
Fuculose-1-P
Aldolase Product

110
+
109

The synthesis of N-acetyl derivatives of an azasugar of Scheme 4 proceeds similarly from the reaction of DHAP with (RS)3-azido-2-acetamidopropanal diethyl acetal, which is prepared from 3-azido-2-hydroxypropanal as described in Pederson et al., *J. Org. Chem.*, 55:4897 (1990). A key element in the synthesis of these N-acetyl dideoxyazasugars is the preparation of Compound IV and its enantiomer as is shown in Scheme 5, below, and in which Roman numerals are used for intermediate compounds leading to the azido α-ketose phosphate.

Scheme 5

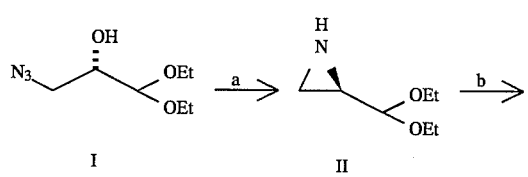

I
II

-continued
Scheme 5

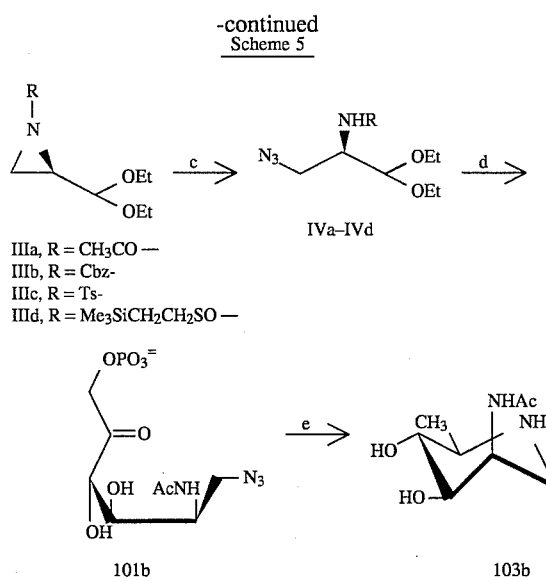

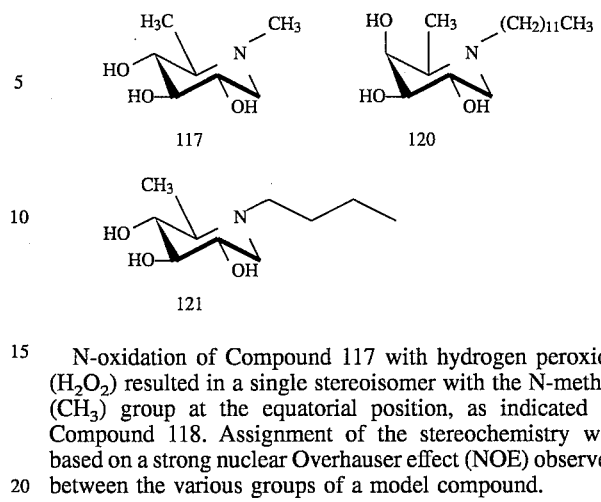

Thus, Compound I (>98 percent ee) prepared previously [Von der Osten et al., *J. Am. Chem. Soc.*, 111:3924 (1989); Pederson et al., Heterocycles, 28:477 (1989)] was converted to Compound II [Pederson et al., *J. Org. Chem.*, 55:489 (1990)] in step a, followed by N-acetylation to Compound IIIa (95 percent ee). Nucleophilic opening of aziridine Compound IIIa with sodium azide in the presence of zinc chloride (ZnCl$_2$) gave Compound IVa in 60 percent yield, in step c. The other protecting "R" groups are as shown in Scheme 5. Higher yields (75–86 percent) were obtained with other protecting groups (e.g. IIIb–IIId; Cbz=carbobenzoxy, Ts=p-toluenesulfonyl). The protecting group of IIId can be removed by fluoride [Weinreb et al., *Tetrahedron Lett.*, 2099 (1986)].

Acid hydrolysis was used to unmask the aldehyde protecting group of Compound IVa. The unmasked product of Compound IVa (3 equivalents) was condensed with 1 equivalent of dihydroxyacetone phosphate (DHAP) in the presence of FDP aldolase at pH 6.5 to give Compound 101b (60 percent) in step d. Palladium catalyzed cyclization of Compound 101b provided Compound 103b, step e.

Compound 101d was prepared similarly from the enantiomer of Compound I. Thus, starting with racemic Compound I, a mixture of Compounds 103b and 103d in a 12:1 ratio was obtained.

Starting with enantiomerically pure aldehyde substrates, Compounds 103b and 103d were obtained separately.

The reductive aminations are all diastereoselective and consistent with the previous finding [von der Osten et al. *J. Am. Chem. Soc.*, 111:3924 (1989)] that hydrogen would attack the imine intermediate in a facial selective manner to avoid the torsional strain developed during the reduction (e.g., reactions with Compounds 101a–101f and Compound 104). An additional finding in this study is that hydrogen always approaches from the side opposite to the axial substituent (e.g., reactions with Compounds 101a, 101b, 101e, 104 and 108) and this steric effect seems to override the torsional strain effect. The A$_{1,2}$ strain (e.g., Compounds 101 or 104) seems not to affect the stereochemical course of the reduction.

Compound 103c was N-methylated to give Compound 117. Similar alkylation with a longer alkyl group such as lauryl or butyl provides Compounds 120 and 121, respectively.

N-oxidation of Compound 117 with hydrogen peroxide (H$_2$O$_2$) resulted in a single stereoisomer with the N-methyl (CH$_3$) group at the equatorial position, as indicated in Compound 118. Assignment of the stereochemistry was based on a strong nuclear Overhauser effect (NOE) observed between the various groups of a model compound.

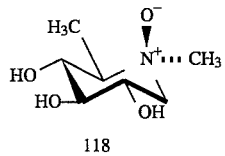

Synthesis of Compounds 114a–c also begins with 3-azido-2-hydroxypropanal, with formation of the precursor azaketose being catalyzed by DERA. DERA is unique in that it can catalyze the aldol condensation of two aldehydes. Therefore, in the case of Compound 114a the reactants were (RS)3-azido-2-hydroxypropanal and acetaldehyde to provide Compound 113a; Compound 114b was formed via the reaction of (RS)3-azido-2-hydroxypropanal and acetone to form Compound 113b; and Compound 114c was formed by reacting (RS)-3-azido-2-hydroxypropanal with propionaldehyde to form Compound 113c. None of the resulting azidoketoses or azidoaldoses contained phosphate groups, so reductive cyclization yielded Compounds 114a–c directly from parent Compounds 113a–c. Compounds 113a–c and 114a–c are shown below.

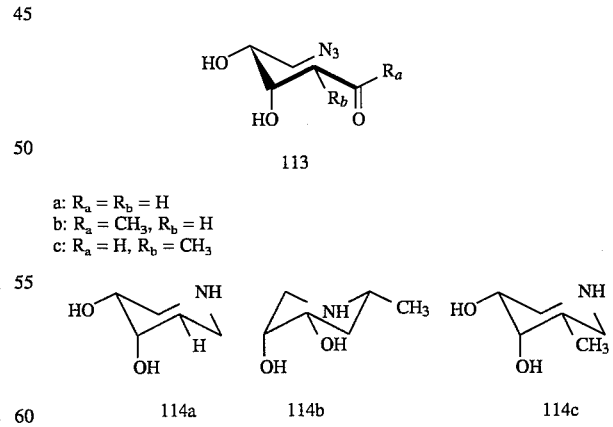

(b) Enzymes
(i) Nucleotide-sugar-pyrophosphorylase
As set forth above, nucleotide-sugar-pyrophosphorylases can be obtained from commercial sources, isolated and purified from tissue or obtained in recombinant form.
For example, CMP-sialic acid synthetase can be isolated and purified from cells and tissues containing the synthetase enzyme by procedures well known in the art. See, e.g., Gross et al., *Eur. J. Biochem.*, 168:595 (1987); Vijay et al., *J. Biol. Chem.*, 250(1):164 (1975); Zapata et al., *J. Biol. Chem.*, 264(25):14769 (1989) and Higa et al., *J. Biol. Chem.*, 260(15):8838 (1985). The gene for this enzyme has also been sequenced. Vann et al., *J. Biol. Chem.*, 262:17556 (1987). Shames et al. also recently reported overexpression of the gene for use in a gram scale synthesis of CMP-NeuAc. Glycobiology, 1:187 (1991).

In one embodiment, grey matter from bovine brain is homogenized, the homogenate centrifuged to form a pellet and a supernatant, and the supernatant lyophilized to yield a powder. The lyophilized powder is reconstituted in distilled water, homogenized and centrifuged to yield a supernatant and a fluffy pellet containing the CMP-sialic acid synthetase. The synthetase enzyme is double extracted from the fluffy pellet with KCl to yield a semi-purified extract. Contaminating amounts of nucleoside phosphatase and O-acetyl esterase are removed from the semi-purified extract by sequential ammonium sulfate precipitation and dialysis. Higa et al., *J. Biol. Chem.*, 260(15):8838 (1985).

In another embodiment, CMP-sialic synthetase is obtained from transformed host cells using genetic engineering and recombinant DNA technologies. One such method for obtaining CMP-sialic acid synthetase has been reported by Zapata et al., *J. Biol. Chem.*, 264(25):14769 (1989). In this embodiment, plasmid pSR35 containing the gene for *E. coli* native CMP-sialic acid synthetase is digested with Eco RI and Hind III to yield a 2.7 kb fragment, which is inserted into Eco RI-Hind III digested vector pKK223-3 (Pharmacia LKB Biotechnology Inc.) to form plasmid pWA1. Plasmid pWA1 is then used to transform *E. coli*. The transformed *E. coli* are reported to express native CMP-sialic synthetase to a level 10–30 fold higher than in non-transformed bacteria. Zapata et al., *J. Biol. Chem.*, 264(25):14769 (1989).

In another and preferred embodiment, a native or modified CMP-sialic acid synthetase is obtained from host cells transformed with a novel bacteriophage lambda vector system recently described by Huse et al., Science, 246:1275 (1989). Detailed descriptions of this method for obtaining native or modified CMP-sialic acid synthetase are set forth in Examples 2 and 9.

According to one aspect of this preferred embodiment, genomic DNA is extracted from *E. coli* strain K235 (ATCC 13207), and the gene for CMP-sialic acid synthetase is isolated via polymerase chain reaction (PCR) amplification in the presence of two custom-designed polynucleotide primers (see Example 2). One primer contains an Eco RI restriction site, a ribosomal binding sequence, a start codon, and an oligonucleotide corresponding to the N-terminal hexapeptide of the enzyme The second primer contains, from 3' to 5' an Xba I restriction site, a stop codon, a decapeptide tag sequence, and a sequence corresponding to the C-terminal heptapeptide of the enzyme. The amplified gene was cloned into a lambda ZAP™ (Stratagene Cloning Systems, La Jolla, Calif.) vector at the Eco RI and Xba I sites for the construction of a phagemid (CMPSIL-1) for expression in *E. coli* Of a modified synthetase enzyme that includes the decapeptide tag.

The decapeptide tag serves as a marker to facilitate the selection of positive clones and can be removed by another PCR (polymerase chain reaction) with primers that do not contain the decapeptide tag sequence if the native enzyme is desired.

The native enzyme was also prepared by expression from another phagemid (CMPSIL-W10) in *E. coli*. This phagemid was constructed from CMPSIL-1 as discussed hereinafter by removal of the decapeptide tag condons using PCR technology, followed by digestion of CMPSIL-1 and the PCR product with Eco RI and Xba I, and religation of the appropriate DNA sequences.

The native and the modified enzymes have similar $k_{cat}$ and $K_m$ for NeuAc and CTP. The modified enzyme is more active than the native enzyme at higher pH values (See Example 9 hereinafter). Studies on specificity indicate that both enzymes have high specific activity for C-9 modified NeuAc derivatives at neutral pH (See Example 9 hereinafter).

It was particularly surprizing that DNA coding for an emzyme as large as native or modified CMP-sialic acid synthetase could be successfully cloned into and translated from this phage vector. Prior reports had only described use of DNA coding for an antibody Fab fragment (about 50,000 kd), which is about 15–20 percent of the size of the present DNA and protein.

Transfected *E. coli* containing phagemid CMPSIL-1 produce approximately 100 U/L of CMP-sialic acid synthetase as the modified enzyme compared to <0.1 U/L for the wild-type, non-transformed strain, corresponding to a >1,000-fold increase of enzyme activity. Such a transformed *E. coli* was deposited on Feb. 19, 1991 with the American Type Culture Collection, Rockville, Md. and assigned ATCC accession No 68531. *E. coli* transformed with phagemid CMPSIL-W10 produce approximately 35 U/L of native CMP-sialic acid synthetase.

(ii) Glycosyltransferases

Glycosyltransferases can also be obtained from a variety of sources. By way of example, β1,4 galactosyltransferase from bovine milk (GalT) can be produced in recombinant form. GalT, like many other glycosyltransferases, is primarily present in the golgi apparatus in a membrane-bound form, which, after proteolysis generates a soluble active form, the socalled "catalytic domain" which soluble form appears in body fluids such as milk and serum. Paulson, et al., *J. Biol. Chem.*, 264:17615 (1989).

The catalytic domain of bovine GalT is composed of 324 amino acids corresponding to the C-terminal sequence of the intact 402-amino acid membrane-bound enzyme. The catalytic or active domain of human GalT is very similar to bovine GalT both in sequence (>90 percent homology) and substrate specificity. The active domain has been cloned into an *E. coli* expression system pIN-GT (See FIG. 1). This expression system incorporates a fusion of the catalytic domain of GalT with the signal sequence of omp A, the major lipoprotein of prokaryotes, so that the enzyme is translocated to the periplasmic space where it is released from the signal sequence by action of signal peptidase to give enzymatically active GalT. Aoki, et al., *EMBO*, 9:3171 (1990).

The recombinant GalT enzyme produced via this expression system contains an additional tripeptide Ala-Glu-Leu attached to the N-terminal Thr residue of the soluble GalT. To improve the expression level, plasmid pIN-GT in *E. coli* strain SB221 was isolated and transformed into JM109, an *E. coli* strain with a damaged cell wall (ATCC 53323). Shima, et al., *J. Ferm. Bioeng.*, 68:75 (1989).

Approximately $2 \times 10^{-3}$ U of Gait can be obtained from a 150 mL fermentation, corresponding to a 35-fold increase of activities compared to the previous expression in SB221. Aoki, et al., Supra. The enzyme appeared primarily in the chloroform extracted periplasmic fraction as no significant difference in activity excreted into the media was observed.

In a similar mannner, sialyl transferase enzymes can be obtained from commercial sources, (Sigma Chemical Company, St. Louis, Mo.; Boehringer Mannheim, Indianapolis, Ind. and Genzyme, Cambridge, Mass.), isolated and purified from animal tissues such as bovine submaxillary gland and rat liver [See e.g., Gross et al., *Eur. J. Biochem.*, 168:595 (1987) and Higa et al., *J. Biol. Chem.*, 260(15):8838 (1985)] or in recombinant form [See e.q., Ernst et al., *J. Biol. Chem.*, 264:3436 (1989); Masibay et al., *Proc. Natl. Acad. Sci. U.S.A.*, 86:5733 (1989); Toghrol et al., *Biochemistry*, 29:2349 (1990); Appert et al., *EMBO*, 9:3171 (1990) and Joziasse et al., *Eur. J. Biochem.*, 191:75 (1990)].

B. Glycosidase Methods

An alternative synthetic method for the production of the oligosaccharides of the present invention uses the enzyme β-galactosidase. According to such a method a monosaccharide acceptor of this invention is reacted with a β-galactoside derivative. A preferred β-galactoside derivatives is a p-nitrophenyl β-galactoside.

Thus, for example when Compound 5 from Table 2 is reacted with p-nitrophenyl β-galactoside in the presence of β-galactosidase (EC 3.2.1.23 from *E. coli*) according to Scheme 6 below, Compound 9 is obtained (Example 1F).

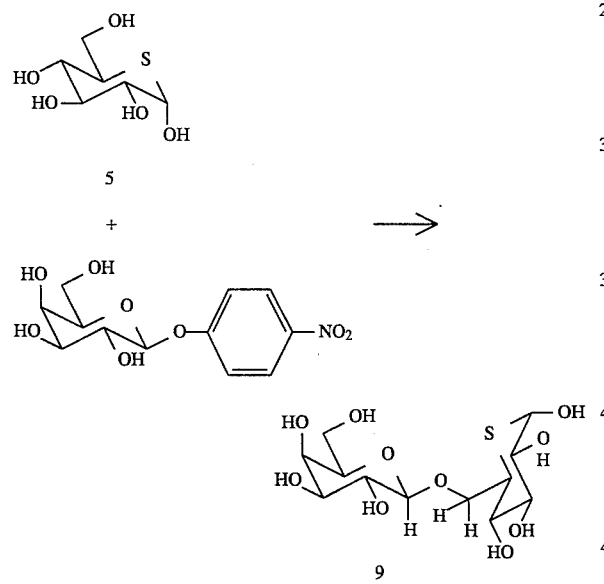

Compound 9 possesses a β1,6 linkage. Thus, in contrast to the method using glycosyltransferase, the glycosidase method produces compounds having a 1,6 glycosidic linkage.

Not all of the monosaccharide acceptors of the present invention are suitable substrates for β-galactosidase. For example, when Compound 3 or 4 from Table 2 are used as a substrate, no product was obtained. Neither azasugar was an inhibitor of β-galactosidase. p-Nitrophenyl β-galactoside was hydrolyzed by the enzyme at the same rate in the absence and presence of the azasugars.

Confirmation of the structure and linkage of synthesized oligosaccharide compounds is accomplished by nuclear magnetic resonance (NMR) spectroscopy using $^1H$ and $^{13}C$ NMR data (at 300 MHz or 500 MHz, and 125 MHz, respectively). The $^1H$-NMR chemical shift assignment for each proton is established by extensive decoupling experiments.

Typically, a large downfield shift (0.1–0.3 ppm) for the protons attached to the carbon in a glycosidic linkage relative to the starting monosaccharide is observed. Correspondingly, the other protons experience little shifts. $^1H$-Nuclear Overhauser effect (NOE) experiments are used to further confirm the linkage and conformation.

For example, Compound 9 displayed a 4 percent enhancement of one of the H-6 resonances of the 5-thioglucose when the H-1 of galactose was irradiated, indicative of the close proximity of the H-6 of the 5-thioglucose to the H-1 of the galactose moiety. Additionally, in the $^{13}C$-NMR spectra, a downfield shift of the C-6 resonance was observed, along with no significant shifts for the other carbon signals. Such data indicate that Compound 9 has a 1,6 linkage.

Further evidence for the assignment of the regiochemistry of a disaccharide linkage is provided by the analysis of the 1H spectra of the per-acetylated disaccharide. Thus, the H-1 to H-4 resonances of a 5-thio-D-glucose moiety (Compound 5 from Table 2) experiences a large downfield shift of 1.3 to 1.8 ppm (relative to the free disaccharide) upon acetylation. Correspondingly, the H-5 and H-6 resonances experience only minor shift (−0.33 to +0.38 ppm) upon acetylation.

The Compositions

The present invention also contemplates a composition that comprises a glycosidase- or glycosyltransferase-inhibiting amount of a beforedescribed oligosaccharide dispersed in an aqueous medium. Preferably, the aqueous medium is a pharmaceutically acceptable, non-toxic medium such as normal saline, phosphate-buffered saline, Ringer's solution or the like as are well known in the art. The aqueous medium can also comprise blood, serum, plasma or lymph of a mammal such as a mouse, rat, rabbit, guinea pig, dog or human to which the azapyranose is administered.

A glycosidase- or glycosyltransferase-inhibiting amount is an amount that inhibits a preselected glycosidase or glycosyltransferase enzyme by at least 25 percent, more preferably by about 50 percent, and most preferably by about 75 percent or more.

It appears that a glycosidase inhibitor can be used as a substrate for another glycosidase (e.g., β-galactosidase). For example, Compound 5 from Table 1 is an inhibitor of α-glucosidase.

Compounds 3, 4, 5 and 6 from Table 1 are potent inhibitors of exoglucosidases (e.g., β-glucosidase), and their glycosides are inhibitors of endoglucosidases: several natural and synthetic products of this type are potent endoglycosidase inhibitors. See, e.g., Kajimoto, et al., *J. Am. Chem. Soc.*, 113:6187 (1991); and Liotta, et al., *J. Am. Chem. Soc.*, 111:783 (1989).

Further, Compounds 2i and 2o from Table 1 can inhibit α-1,3/4-fucosyltransferase due to the lack of an appropriately oriented 3-OH group. Lowe, et al., *Cell*, 63:475 (1990). The data of Table 1a show that Compound 8 is of similar inhibitory potency to Compound whereas Compound 10a is more inhibitory than either compound. The FucT used for these studies was provided by Dr. J.B. Lowe of the University of Michigan, Ann Arbor, Mich.

Compound 2j from Table 1 is useful for the synthesis of Le$^x$ [Galβ1,4(Fucα1,3)GlcNAc] and sialyl Le$^x$ [NeuAcα2, 3Galβ1,4(Fucα1,3)GlcNAc] as described in Scheme 3. A chemical-enzymatic synthesis of sialyl Le$^x$ can be carried out with peracetylation of Compound 2j from Table 1 followed by selective deprotection of the 3-oallyl group with a Ru catalyst [Corey, et al., *J. Org. Chem.*, 38:3224 (1973)] to liberate the 3-OH group for fucosylation.

The deoxy-azasugars are known to inhibit glycosidase activity as shown below in Table 3.

TABLE 3

Glycosidase Inhibition

| Compound | Brewer's Yeast (BY) or Sweet Almond (SA) | $K_i(M)$ |
| --- | --- | --- |
| 103c | α-Glucosidase (BY) | $1.56 \times 10^{-3}$ |
|  | β-Glucosidase (SA) | $7.8 \times 10^{-4}$ |
| 117 | α-Glucosidase (BY) | $1.78 \times 10^{-3}$ |
|  | β-Glucosidase (SA) | $1.4 \times 10^{-4}$ |
| 118 | α-Glucosidase (BY) | $6.95 \times 10^{-3}$ |
|  | β-Glucosidase (SA) | $1.49 \times 10^{-3}$ |
| Controls |  |  |
| 119 | α-Glucosidase (BY) | $3.69 \times 10^{-4}$ |
|  | Type I (calf liver) | $7.0 \times 10^{-8}$ |
|  | β-Glucosidase (SA) | $4.3 \times 10^{-5}$ |
| 122 | α-Glucosidase (BY) | $>1.0 \times 10^{-2a}$ |
|  | β-Glucosidase (SA) | $8.0 \times 10^{-5}$ |
| 123 | α-Glucosidase (BY) | $8.67 \times 10^{-6}$ |
|  | Type I (calf liver) | $1.0 \times 10^{-6a}$ |
|  | β-Glucosidase (SA) | $1.8 \times 10^{-5b}$ |
|  | α-D-Mannosidase (jack bean) | $4.0 \times 10^{-4}$ |
|  | β-D-Galactosidase (jack bean) | No inhibition[c] |

[a]Schweden et al., Arch. Biochem. Biophys., 248:335 (1986)
[b]Dale et al., Biochemistry, 24:3530 (1985)
[c]No significant inhibition observed with 10 mM inhibitor in the assay.

A before-described oligosaccharide is dispersed in the aqueous medium. Such dispersal includes suspensions as well as true solutions, which are ultimate dispersions, in the aqueous medium.

The following examples illustrate specific embodiments of this invention and are not limiting of the specification and claims in any way.

EXAMPLES

Example 1: Synthesis of Oligosaccharides

A. (β-D-Galactopyranosyl- (1,4) -5-thio-D-glucopyranose), Compound 7 from Table 1

5-thioglucose, Compound 5 from Table 1, (100 mg, 500 mmol), was reacted with 5 U of Galt (Sigma Chem. Co., St. Louis, Mo.), UDP-glucose (350 mg, 500 mmol), α-lactalbumin ( 0.1 mg/mL) and UDP-glucose epimerase ( 10 U) in 10 mL of 50 mM sodium cacodylate (pH 7.0) containing 5 mM of $MnCl_2$. GalT had a specific activity of 4–7 U/mg (1 U=1 mmol of UDP-Gal transferred per minute). The purified enzyme had a reported specific activity of 15 U/mg using GlcNAc as an acceptor. The $K_m$ value for UDP-Gal is 0.5 mM. The reaction mixture was incubated at 37° C. for two days. The product was isolated via a Dowex 1 formate column followed by gel filtration (Bio Gel P-2) to give 90 mg of the title compound in 50 percent yield.

$^1$H-NMR ($D_2O$, 500 MHz) δ4.95 (d, $J_{1,2}$=3 Hz, H-1α5ThioGlc), 4.51 (d, $J_{1,2}$=8 Hz, H-1 Gal), 4.05 (dd, $J_{5,6}$=5 Hz, $J_{6,6}$=12 Hz H-6'5ThioGlc Hz), 3.83–3.9 (H-4 Gal; H-4 5ThioGlc; H-6 5ThioGlc), 3.8 (dd, $J_{2,3}$=9.6 Hz, H-2 5ThioGlc), 3.65–3.75 (H-5 Gal, H-6 Gal; H-6' Gal, H-3 5ThioGlc), 3.62 (dd, $J_{2,3}$=10 Hz, $J_{3,4}$=3.5 Hz, H-3 Gal), 3.53 (dd, H-2 Gal), 3.32 (ddd, $J_{4,5}$=10.5 Hz, $J_{5,6}$=2.5 Hz, $J_{5,6}$=5 Hz, H-5 5thioGlc); $^{13}$C-NMR (125 MHz, $D_2O$) δ for Gal 103.2 (C-1), 71.7 (C-2), 72.7 (C-3), 69.0 (C-4), 5.8 (C-5), 61.5 (C-6); for 5ThioGlc 73.3 (C-1), 75.7 (C-2), 73.0 (C-3), 82.3 (C-4), 42.5 (C-5), 59.7 (c-6). HRMS (M+Cs$^+$) calcd 490.9988, found 491. 0022.

B. β-D-Galactopyranosyl-(1,4)-2-acetamido-6-O-acetyl-2-deoxy-D-glucopyranose, Compound 9-e About 20 mg (76 mmol) of 3-O-AcetylGlcNAc, Compound 1f from Table 1, was reacted with about 1 equivalent of UDPGlc (50.5 mg) in 1 mL of 0.05M Nacacodylate/HCl containing 0.05 mM NAD$^+$, 10 mM DTT, and 5 mM $MnCl_2$, pH 7.0. UDPGlc epimerase (1 U) and galactosyltransferase (2 U) were added. The mixture was shaken at 37° C. and after two days another 2 U of galactosyltransferase were added. After four days the solution was lyophilized and the residue was purified with a silica gel column chromatography to obtain 6 mg of the title compound.

$^1$H NMR ($D_2O$) δ1.98 (s, 3H, NAc), 2.08 (s, 3H, OAc), 3.50–3.57 (m, 1H, 2-H, (glcNAc), 3.63–3.82 (m, 6H, 2'-H (gal), 3'-H, 4'-H, 5'-H, 3-H, 4-H), 3.85–3.97 (m, 2H, 6'-$H_2$), 4.01 (ddd, J=7 Hz, J=4 Hz, J=2.2 Hz, 5-Ha), 4.10–4.19 (m, 5-Hb), 4.21 (dd, J=12 Hz, J=4 Hz, 6-$H_a$), 4.22 (d, J=7.8 Hz, 1-Ha), 4.23 (d, J = 7.8 Hz, 1-Hb), 4.29 (dd, J=2.2 Hz, J=12 Hz, 6-$H_b$b), 4.35–4.48 (m, 6-$H_2$b). $^{13}$C NMR δ21.0, 22.7 (2CH$_3$), 54.4, 56.8 (C-2'), 61.8, 63.8 (C-6, C-6,), 69.3, 70.1 71.7, 73.3 76.3 (C-2', C-3', C-4', C-5', C-3, C-4, C-5), 79.4 (C-4), 91.4, 96.1 (C-1), 104.0 (C-1'), 174.5, 175.0 (2CO). HRMS calcd. for ($C_{12}H_{27}O_{12}N+Cs^+$): 558.0588; found: 558. 0590.

C. Allyl β-D-galactopyranosyl-(1,4)-2-acetamido- 2,3-dideoxy,β-D-glucopyranoside, Compound 2i Allyl-1,3-deoxy-GlcNAc, Compound 1i from Table 1, was reacted with UDPGlc in 1 mL of 0.05M Nacacodylate/HCl containing 0.05 mM NAD$^+$, 10 mM DTT, and 5 mM $MnCl_2$, pH 7.0. UDPGlc epimerase (1 U) and galactosyltransferase (2 U) were added. The mixture was shaken at 37° C. and after two days another 2 U of galactosyltransferase were added. After four days the solution was lyophilized and the residue was purified with a silica gel column chromatography to obtain the title compound.

$^1$H NMR ($D_2O$) δ1.62 (1 H, q, J=12.18 Hz, H-3ax), 1.94 (3 H, s, NHAc), 2.46 (1 H, br dt, J=4.61, 12.57 Hz, H-3eq), 3.44 (1 H, dd, J=8.04, 9.92 Hz, H-2'), 4.41 (1 H, d, J=7.82 Hz, H-1'), 4.51 (1 H, d, J= 8.38 Hz, H-1); $^{13}$C NMR ($D_2O$) δ22.45, 35.78, 49.23, 61.03, 61.26, 68.89, 70.55, 71.26, 73.03, 74.19, 75.52, 78.85, 102.01, 104.21, 118.60, 133.81, 174.12; HRMS Calcd for $C_{17}H_{29}NO_{10}Cs$ (M+Cs$^+$): 540.0846. Found: 540.0846.

D. β-D-Galactopyranosyl-(1,4)-D-glucal, Compound 8

Compound 6 from Table 1, was reacted with UDPGlc in 1 mL of 0.05M Na-cacodylate/HCl containing 0.05 mM NAD$^+$, 10 mM DTT, and 5 mM $MnCl_2$, pH 7.0. UDPGlc epimerase (1 U) and galactosyltransferase (2 U) were added. The mixture was shaken at zero degrees C and after four days another 2 U of galactosyltransferase were added. After four days the solution was lyophilized and the residue was purified with a silica gel column chromatography to obtain the title compound.

$^1$H-NMR (500 MHz, $D_2O$) δ6.4 (dd, $J_{1,2}$=6 Hz, $J_{1,3}$=1.6 Hz, H-1 Glucal), 4.7 (dd, $J_{2,3}$=2.6 HZ, H-2 Glucal) 4.49 (d, $J_{1,2}$=7.8 Hz, H-1 Gal) , 4.35 (br dt, $J_{2,3}$=2.6 Hz, $J_{3,4}$=6.5 Hz, H-3 Glucal), 3.99 (d, $J_{4,5}$=9.3 Hz, $J_{5,6}$=$J_{5,6}$=3.7 HZ, H-5 Glucal), 3.85–3.9 (H-4 Gal; H-6 and H-6' Glucal), 3.82 (dd, H-4 Glucal), 3.68–3.75 (H-5, H-6, H-6' Gal), 3.63 (dd, $J_{2,3}$=10 Hz, $J_{3,4}$=3.4 Hz, H-3 Gal), 3.5 (dd, $J_{1,2}$=8.6 Hz, H-2 Gal). $^{13}$C-NMR (125 MHz, $D_2O$) δ for Gal 103.9 (C-1), 71.9 (C-2), 73.5 (C-3), 69.5 (C-4), 76.3 (C-5), 62.0 (C-6); for glucal 144.9 (C-1), 102.7 (C-2) 68.3 (C-3), 78.4 (C-4), 77.7 (C-5), 60.6 (C-6). HRMS (M+Cs$^+$) calcd. 441.0162, found 441.0121.

E. β-D-Galactopyranosyl-(1,4)-deoxynojirimycin, Compound 10a

Compound 3 from Table 1, was reacted with UDPGlc in 1 mL of 0.05M Na-cacodylate/HCl containing 0.05 mM NAD$^+$, 10 mM DTT, and 5 mM $MnCl_2$, pH 7.0. UDPGlc epimerase (1 U) and galactosyltransferase (2 U) were added. The mixture was shaken at 37° C. and after four days another 2 U of galactosyltransferase were added. After four days the solution was lyophilized and the residue was purified with a silica gel column chromatography to obtain the title compound.

$^1$H-NMR (D$_2$O, 500 MHz) δ4.3 (d, J$_{1,2}$=7.5 Hz, H-1 Gal), 3.76 (dd, J$_{5,6}$=3.0 Hz, J$_{6,6}$=12.5 Hz, H-6' DNJ), 3.74 (br d, J$_{3,4}$=3 Hz, H-4 Gal), 3.7 (dd, J$_{5,6}$=5.0 Hz, H-6 DNJ), 3.52–3.65 (m, H-6 Gal, H-6' Gal, H-5 Gal, H-2 DNJ, H-4 DNJ), 3.5 (dd, J$_{2,3}$=10.5 Hz, H-3 Gal), 3.39 (t, J$_{2,3}$=J$_{3,4}$=9.5 Hz, H-3 DNJ), 3.38 (dd, H-2 Gal), 3.13 (dd, J$_{1eq,1ax}$=12.5 Hz, J$_{1eq,2}$=5.0 HZ, H-1eq DNJ), 2.85–2.90 (m, H-5 DNJ), 2.56 (br t, J$_{1ax,2}$=12 Hz, H-1ax DNJ). $^{13}$C-NMR (125 Hz, D$_2$O) δ for Gal 103.7 (C-1), 71.7 (C-2), 73.2 (C-3), 69.2 (C-4), 76.3 (C-5), 61.8 (C-6); for DNJ 47.4 (C-1), 69.04 (C-2), 76.2 (C-3), 78.9 (C-4), 59.4 (C-5), 60.0 (C-6). HRMS (M+Cs$^+$) calcd. 458.0427, found 458.04444.

F. β-D-Galactopyranosyl-(1,6)-5-thio-D-glucopyranose, Compound 9

β-Galactosidase from *E. coli* (EC 3.2.1.23:0.50 mg, 172 U) was added at 23° C. to a solution of 4-nitrophenyl β-D-galactopyranoside (150 mg, 0.50 mmol) and 5-thio-D-glucose (49 mg, 0.25 mmol) in Na$_2$HPO$_4$/MgCl$_2$ buffer (4 mL of a 0.10M solution in Na$_2$HPO$_4$ and 10 mM in MgCl$_2$, pH 7.0) and Tris (1 mL of a 0.05M solution, pH 7.3). The reaction was maintained at 23° C. with periodic monitoring by TLC. After 58 hours, the reaction was terminated by heating at 100° C. for 30 minutes. The solution was filtered and lyophilized and the residue was purified by column chromatography (silica gel, 3:2:1 ethyl acetate-acetic acid-water). The fraction containing the disaccharide was further purifed by gel filtration chromatography using a Bio-Gel P-2 column (2×40 cm, 200–400 mesh) eluted with H$_2$O to afford the title compound (26.4 mg, 29.5 percent based on 5-thio-D-glucose) as a white amorphous solid (Rf= 0.44, silica gel, 3:2:1 EtOAc-HOAc-H$_2$O). The silica gel chromatography also afforded galactose and 5-thio-D-glucose. Analysis of the disaccharide indicated a mixture of a to b anomers in a ratio of 11:1. A Anomer: ("A" refers to the 5-thioglucose moiety while "B" refers to the galactose moiety.) The differences in coupling constants are due to round-off error.)

$^1$H NMR (500 MHz, D$_2$O) δ4.82 (d, J=3.0 Hz, 1H, H1-A), 4.22 (d, J=8.0 Hz, 1H, H1-B), 4.01 (dd, J=2.5, 11.0 Hz, 1H, H6-A), 3.82 (dd, J=5.5, 11.0 Hz, 1H, H6-A), 3.74 (d, J=3.0 Hz, 1H, H4-B), 3.63–3.54 (m, 3H, H2-A, H3-A, H5-B), 3.50 (t, J=10.5 Hz, 1H, H4-A), 3.48–3.45 (m, 2H, H6-B), 3.46 (dd, J=3.5, 10.0 Hz, 1H, H3-B), 3.36 (app. t, J=9.0 Hz, 1H, H2-B), 3.20–3.14 (m, 1H, H5-A); $^{13}$C NMR (125 MHz, D$_2$O) δ103.8, 75.6, 74.0, 73.7, 73.6, 73.1, 71.1, 69.1, 68.8 (CH$_2$), 61.4 (CH$_2$), 41.6; exact mass calcd for C$_{12}$H$_{22}$O$_{10}$SCs (M+Cs$^+$) 490.9988, found 491.0013.

G. =-D-Galactopyranosyl-(1,6)-5-thio-D-glucopyranose octaacetate

Pyridine (0.9 mL, 11.1 mmol), Ac20 (0.14 mL, 1.48 mmol), and (GlcNAc)$_2$ Table 1 (33 mg, 0.09 mmol) were combined at 0° C. The reaction mixture was allowed to warm to 23° C. maintained for 23 hours, and diluted with ethyl acetate (10 mL). The organic phase was rinsed with 1N HCl (10 mL) and the acidic fraction was extracted with ethyl acetate (2×20 mL). The combined organic phases were rinsed with brine (10 mL), dried (MgSO$_4$), and concentrated. The residue was purified by column chromatography (silica gel, 3:1 EtOAc-toluene) to afford the per-acetylated title disaccharide (24 mg, 93 percent) as a colorless glass (Rf=0.61, silica gel, 3:1 EtOAc-toluene). Analysis of the disaccharide indicated a mixture of α to β anomers in a ratio of 6:1.

α Anomer: $^1$H NMR (500 MHz, CDCl$_3$) δ6.12 (d, J=3.5 Hz, 1H, H1-A), 5.42 (app t, J=10.0 Hz, 1H, H3-A), 5.38 (dd, J=1.0, 3.5 Hz, 1H, H4-B), 5.21 (dd, J=3.0, 10.0 Hz, 1H, H2-A), 5.19 (app t, J=11.0 Hz, 1H, H4-A), 5.18 (dd, J=8.0, 10.5 Hz, 1H, H2-B), 4.99 (dd, J=3.5, 10.5 Hz, 1H, H3-B), 4.40 (d, J=9.0 Hz, 1H, H1-B), 4.16 (dd, J=6.5, 11.0 Hz, 1H, H6-B), 4.10 (dd, J=6.5, 11.0 Hz, 1H, H6-B), 4.05 (dd, J=3.5, 10.0 Hz, 1H, H6-A), 3.88 (dt, J=1.0, 7.0 Hz, 1H, H5-B), 3.57 (ddd, J=3.5, 7.0, 10.5 Hz, 1H, H5-A), 3.49 (dd, J=7.5, 10.5 Hz, 1H, H6-A), 2.18 (s, 3H, OAc), 2.14 (s, 3H, OAc), 2.09 (s, 3H, OAc), 2.052 (s, 3H, OAc), 2.046 (s, 3H, OAc), 2.01 (s, 3H, OAc), 1.99 (s, 3H, OAc), 1.98 (s, 3H, OAc); $^{13}$C NMR (62 MHz, CDCl$_3$) δ170.3, 170.2, 170.1, 169.7, 169.6, 169.4, 169.1, 101.2, 73.1, 72.3, 70.8, 70.4, 68.1, 67.3 (CH$_2$), 66.8, 61.0 (CH$_2$), 40.8, 20.9, 20.8, 20.6, 20.5; exact mass calcd for C$_{28}$H$_{38}$O$_{18}$SCs (M+Cs$^+$) 827.0833, found 827.0823.

These syntheses demonstrate that Gait and β-galactosidase can be used as catalyst for the preparation of disaccharides on milligram scales with weak acceptor substrates. Given that the enzyme is relatively stable, GalT (and perhaps other glycosyltransferases) seems amenable for the small-scale synthesis of a number of unusual oligosaccharides.

All the subject disaccharides possess similar glycosidic torsional angle as evidenced by the significant NOE's (6–10 percent) between H-1' and H-4. This observation is consistent with that reported by Lemieux that the glycosidic torsional angle is mainly determined by the exo-anomeric effect.

Example 2: Synthesis of Sialyl N-Acetyllactosamine

Sialyl N-acetyllactosamine (NeuAcα2,6Galβ1,4GlcNAc) was synthesized in an enzyme-catalyzed method with the in situ regeneration of CMP-sialic acid according to scheme 4 set forth above.

Neuraminic acid (NeuAc), CMP, ATP, PEP (monosodium salt), MgCl$_2$.6H$_2$O, MnCl$_2$.4H$_2$O, KCl, pyruvate kinase (PK, EC 2.7.1.40), nucleoside monophosphate kinase (NMK, EC 2.7.4.4) and inorganic pyrophosphatase (PPase, EC 3.6.1.1) were purchased from Sigma Chemical Co., St. Louis, Mo. Siaα2,6Gal sialyl transferase (EC 2.4.99.1) was obtained as a generous gift and can be purchased from Sigma Chemical Co., St. Louis, Mo. CMPNeuAc synthetase (EC 2.7.7.43) was obtained from *E. coli* transformed with a CMP-NeuAc gene according to the method set forth below.

NeuAc (0.92 g, 3 mmol), Galβ1,4GlcNAc (1.1 g, 3 mmol), CMP (0.1 g, 30 μmol), ATP (16 mg, 3 μmol), PEP (2.8 g, 6 mmol), MgCl$_2$. 6H$_2$O (0.61 g, 3 mmol), MnCl$_2$.4H$_2$O (0.15 g, 0.8 mmol), KCl (0.22 g, 3 mmol), NMK or MK (450 U), PK (6,000 U), PPase (300 U), CMP-NeuAc synthetase (24 U) , and Siaα2,6Gal sialyl transferase (4 U) were mixed with 150 ml of HEPES buffer (0.2M, pH 7.5) to form a reaction mixture and the reaction mixture maintained under argon at about 25° C. for about 48 hours. After the disappearance of NeuAc (determined by thin-layer chromatography) the reaction mixture was reduced in volume to 20 ml by lyophilization and the lyophilized reaction mixture applied to a Bio Gel P2 (200–400 mesh) column with water as the mobile phase. The trisaccharide-containing fractions were eluted, collected and lyophilized to give pure Neuα2,6Galβ1,4GlcNAc in 97 percent yield.

$^1$H-NMR δ1.701 (1H, t, J=12.5 Hz, H-3$_{ax}$ of NeuAc), 2.007 (3H, s, NHAc of GlcNAc), 2.004 (3H, s, NHAc of NeuAc), 2.649 (1H, dd, J=5.0 and 12.5 Hz, H-3$_{eq}$ of NeuAc, 4.43 1,d, J=8.0 Hz, H-1 of Gal), 4.73 (0.5H, d, J=8.0 Hz, H-1b of GlcNAc), and 5.178 (0.5H, d, J=2.5 Hz, H-1a of GlcNAc).

The turn-over number for ATP was about 1000 and that of CMP, CDP, CTP and CMP-NeuAc was about 100.

These data show that a glycosyl compound can be sialylated in an efficient, enzyme-catalyzed, selfcontained, cyclic, synthetic method involving the in situ regeneration of CMP-sialic acid. This synthetic method provides a novel, high-yield (97 percent) scheme for the large-scale preparation of sialylated glycosyl compounds.

A. Preparation of Recombinant CMP-NeuAc Synthetase

The gene coding for CMP-N-acetylneuraminic acid (CMP-NeuAc) synthetase (EC 2.7.7.43) was amplified from total DNA of *E. coli* strain K-235 through a primer-directed polymerase chain reaction. The gene was fused with a modified ribosome binding site of the original CMP-NeuAc synthetase gene and a decapeptide tag sequence which served as a marker for screening of expressed proteins. The gene was cloned into lambda ZAP™ vector at Eco RI and Xba I sites and overexpressed in *E. coli* Sure at a level approximately 1000 times that of the wild type.

*E. coli* strain K235 (ATCC 13207) was obtained from American Type Culture Collection and maintained on LB (Luria-Bertani) medium (one liter contains: Bacto Tryptone, 25g; Yeast extract, 10 g; NaCl, 3 g: pH 7.0). Genomic DNA was extracted from the *E. coli* according to the method described by Maniatis et al., Molecular Cloning: A Laboratory Manual, Cold Spring Harbor Laboratory, Cold Spring Harbor, N.Y. (1989).

The CMP-NeuAc synthetase gene was isolated via PCR amplification in the presence of two custom-designed primers (Table 4).

to PCR amplification.

The amplified gene was cloned into lambda ZAP™ II vector at the Eco RI and Xba I sites for the construction of phagemid for expression of the enzyme in *E. coli*.

Lambda Zap™ II is a derivative of the original Lambda Zap™ vector (ATCC#40,298) that maintains all of the characteristics of the original Lambda Zap™ including 6 unique cloning sites, fusion protein expression, and the ability to rapidly excise the insert in the form of a phagemid (Bluescript SK-), but lacks the SAM 100 mutation, allowing growth on many Non-Sup F strains, including XL1-Blue. The Lambda Zap™ II vector was constructed as described by Short et al., [*Nucleic Acids Res.*, 16:7583 (1988)] by replacing the Lambda S gene contained in a 4254 base pair (bp) DNA fragment produced by digesting Lambda Zap™ with the restriction enzyme Nco I. This 4254 bp DNA fragment was replaced with the 4254 bp DNA fragment containing the Lambda S gene isolated from Lambda gt10 (ATCC#40,179) after digesting the vector with the restriction enzyme Nco I. The 4254 bp DNA fragment isolated from lambda gt10 was ligated into-the original Lambda Zap™ vector using T4 DNA ligase and standard protocols for such procedures described in *Current Protocols in Molecular Biology*, Ausubel et al., eds., John Wiley and Sons, N.Y., 1987.

The DNA obtained from the PCR amplification was purified on 0.6 percent agarose gel. The DNA band corresponding to 1.3 kb was separated from the agarose and electro-eluted. The DNA was then extracted with phenol/chloroform and precipitated with ethanol overnight at 20° C. The precipitated DNA was disclosed in a proper restriction enzyme buffer supplied by Boehringer Mannheim Biochemical Co. (Indianapolis, Ind.) and digested with 40

TABLE 4

Primer CMP5

5' AT ATT <u>GAATTCT</u> AAACT AGT CG<u>CC AAGGAGAC</u> AGT C<u>AT AAT GAGA</u>
          Eco RI                   Shine Dalgarno       Start <u>ACAAAAATT ATT GCG</u>  3'              (SEQ ID NO: 1)
        gene N-terminal Primer CMP3

5' GC<u>GCTCTAGA</u>CTATT AAGAACCGT AGT CCGGAACGT CGT ACGGG
        Xba I stop                  Decapeptide tag T<u>ATTTAACAATCTCCGCT ATTTC</u>  3'     (SEQ ID NO: 2)
        gene C-terminal Primer CMP5 contained an Eco RI restriction site, a ribosomal binding sequence, a start codon and an oligonucleotide corresponding to the N-terminal hexapeptide of the enzyme (underlined above). Primer CMP3 contained an Xba I restriction site, a stop codon, a decapeptide tag sequence and a sequence corresponding to the C-terminal heptapeptide of the enzyme (also underlined above).

Figure 2:
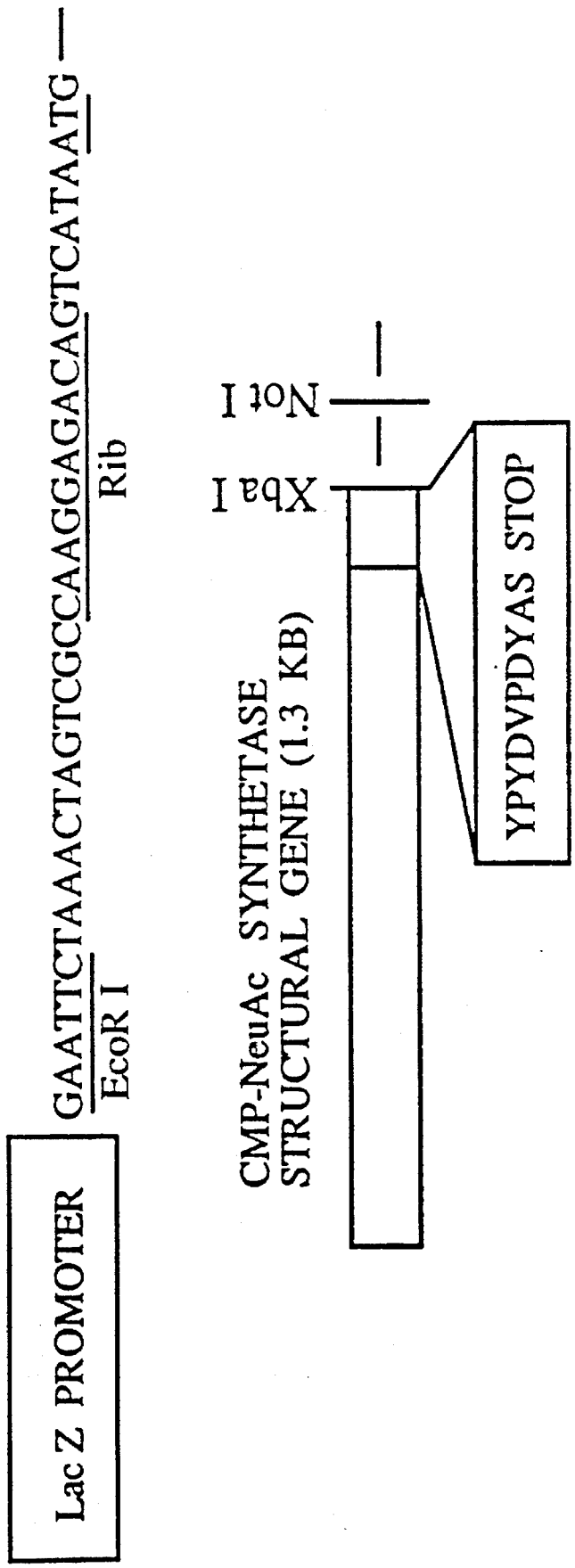
FIG. 2 is a schematic diagram showing the construction of the DNA insert containing the 1.3 kb PCR amplification product that includes the CMP-NeuAc synthetase structural gene as well as the upstream Lac Z promoter and linking DNA having an Eco RI restriction site (underlined), a ribosome binding site (Rib, sequence underlined) and an ATG (underlined) start signal, and the downstream amino acid residue sequence of the tag peptide and DNA stop signal (boxed), followed downstream by Xba I and Not I restriction sites, and the arms from lambda Lcl vector according to Example 2.

PCR amplification was performed in a 100 μL reaction mixture containing 2 μL (2 μg) of *E. coli* strain K235 DNA, 400 nmol of primers CMP5 and CMP3, 200 μM of different dNTPs, 50 mM KCl, 10 mM Tris-HCl (pH 8.3), 2 mM MgCl$_2$, 0.01 percent (w/v) gelatin, 0.1 percent (v/v) Triton X-100, and 2 units of *Thermus Aquaticus* DNA polymerase. The reaction was overlaid with mineral oil and subjected to 35 cycles of amplification. The cycle conditions were set as denaturation at 94° C. for one minute, annealing at 60° C. for two minutes, and elongation at 72° C. for 1.5 minutes. The primers were annealed with *E. coli* DNA at 94° C. for two minutes followed by slow cooling to room temperature prior units/μg DNA of Eco RI and Xba I at 37° C. for two hours. The digested DNA was then recovered by phenol/chloroform extraction and ethanol precipitation and resuspended in a TE buffer (pH 7.5). This DNA was used as an insert. The arms were also prepared from the digestion of vector lambda Lc1 with 20 Units/mg DNA of Eco RI and Xba I and recovered with ethanol precipitation after extraction with phenol/chloroform. Vector lambda LcI was obtained as a generous gift from Dr. R. A. Lerner (Scripps Clinic and Research Foundation, La Jolla, Calif.). The insert was then ligated with the arms and packaged with a packaging kit as suggested by the manufacturer (Stratagene Co., San Diego, Calif.). The PCR amplification product insert with lambda Lcl arms is shown in FIG. 2.

After packaging, the phage solution was used to infect host strain XL1-Blue (Stratagene Co., San Diego, Calif.) and plated on LB agar plates at 37° C. After plaque formation was observed, a nitrocellulose membrane previously soaked with 0.5 mM IPTG (Isopropyl-β-D-thiogalactopyranoside)

solution was carefully placed on the top of the agar-and incubated at 25° C. overnight (about 15 hours). The nitrocellulose membrane was then used for screening with alkaline phosphatase conjugated with the anti-decapeptide tag antibody. Positive clones with intense blue color plaques were cored from the agar plates and transferred to sterile microfuge tubes containing 500 µL of SM buffer and 20 µl of $CHCl_3$. For extension, 200 µl of the phase stock was mixed with 200 µL of LX1-Blue cells ($OD_{660}$=1.0) and 2 µL of R408 helper phage ($1 \times 10^{11}$ pfu/ml from Stratagene Co.), and the mixture incubated at 37° C. for 10 minutes. Excised plasmids were used to infect XL1-Blue cells [Short et al. *Nucleic Acids Res.*, 16:7583 (1988)], plated, and analyzed for expression of the enzyme by ELISA and enzyme activity assays.

Figure 3:
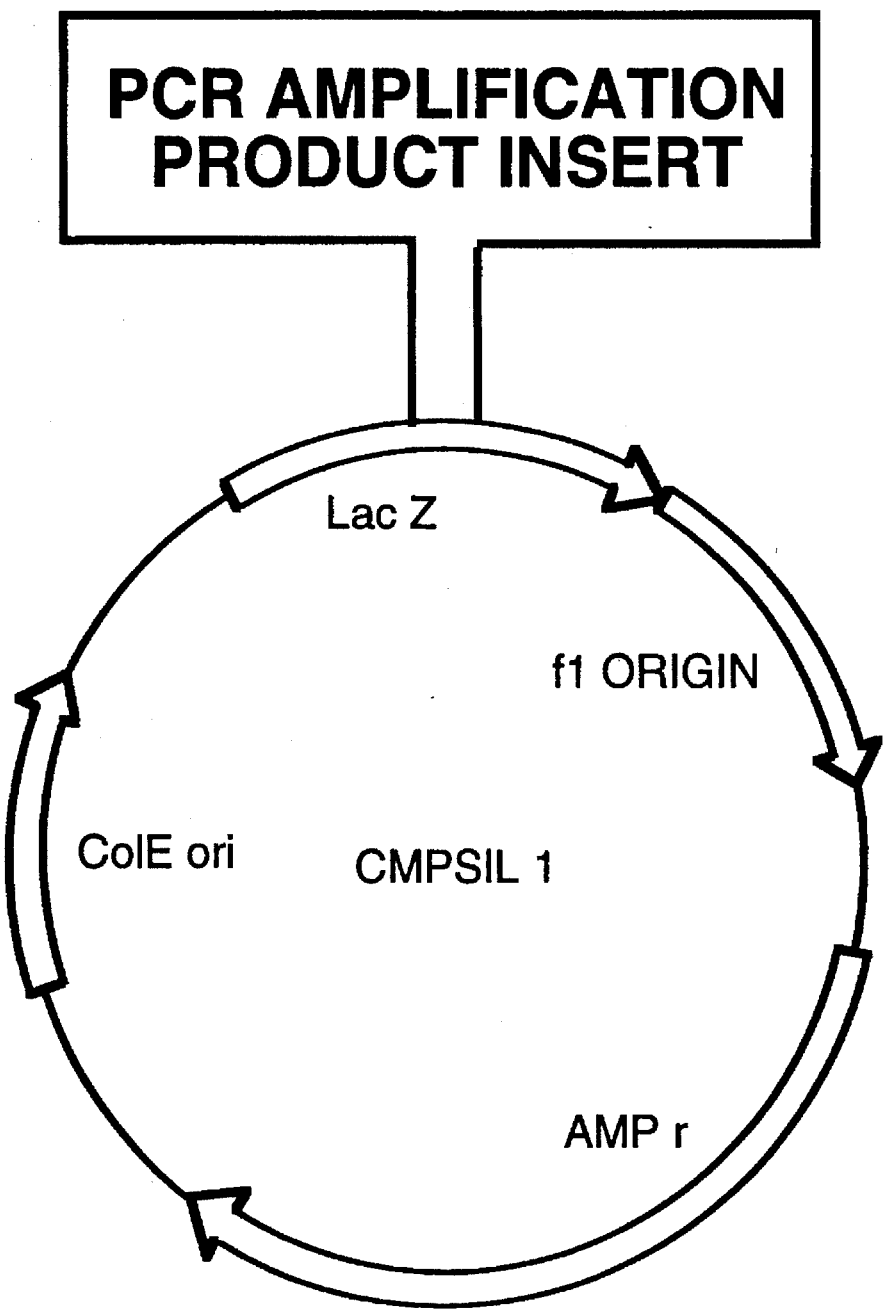
FIG. 3 is a schematic diagram showing the major features of phagemid CMPSIL-1. The PCR amplification product insert from FIG. 2 is shown at the top. The orientations of the insert and other genes are also shown.

One clone which produced higher CMP-NeuAc synthetase was isolated and designated as strain SIL-B3 and the phagemid contained therein designated CMPSIL-1 (FIG. 3). Phagemid CMPSIL-1 was isolated from strain SIL-B3 using a plasmid isolation kit (Qiagen Inc., Studio City, Calif.) and transformed to *E. coli* Sure competent cells (Stratagene Co., San Diego, Calif.). Transformed cells were plated on LB agar plates containing 250 µg/mL ampicillin and screened for high enzyme production using the ELISA assay. One strain, designated *E. coli* SIL-S22 (ATCC 68531), produced about 100 units of CMP-NeuAc synthetase activity per liter of culture broth. This production of CMP-NeuAc synthetase is over 1000 times greater than the amount of CMP-NeuAc synthetase produced by wild-type, non-transformed *E. coli* and over 30 times greater than the amount of CMP-NeuAc synthetase produced by the transformed cells described by Zapata et al., *J. Biol. Chem.*, 264(25):14769 (1989).

*E. Coli* strain SIL-S22 were grown on LB-rich medium containing 250 µg/mL ampicillin to mid-logarithmic phase ($OD_{660}$ about 0.6–0.7) and induced with 0.5 mM IPTG for 10 hours at 30° C. The culture broth was centrifuged at 10,000× g for 20 minutes at 4° C. and the resulting cell pellet was washed with a buffer containing 0.2M Tris (pH 7.5), 0.2 mM dithiothreitol and 20 mM $MgCl_2$. After washing, the cell pellet was resuspended in the same buffer and disrupted by a French pressure cell at 16,000 lb/in$^2$ and centrifuged at 23,000 ×g for 60 minutes. The resulting supernatant was assayed for enzyme activity assay according to the method of Vann et al., *J. Biol. Chem.*, 262:17556 (1987) except that the developed color was extracted with cyclohexanone.

The enzyme was incubated in a 250 µl buffer containing 5.5 mM CTP, 2.8 mM N-acetylneuraminic acid, 0.2M Tris, 20 mM $MgCl_2$ and 0.2 mM DTT, pH 9.0. After the mixture was incubated at 37° C. for 30 minutes, 50 µl of 1.6 M $NaBH_4$ was added to destroy excess NeuAc at room temperature for 15 minutes. The mixture was then put in ice bath and 50 µl of $H_3PO_4$ was added to destroy $NaBH_4$. The mixture was kept at zero degrees C for five minutes then incubated at 37° C. for 10 minutes to cleave the phosphoester bond of the formed CMP-N-acetylneuraminic acid. The free N-acetylneuraminic acid was oxidized with 50 µl of 0.2M $NaIO_4$ at room temperature for 10 minutes, and 400 µl of 4 percent $NaAsO_2$ in 0.5N HCl was added. The solution mixture was then transferred to a test tube containing 1 ml of 0.6 percent thiobarbituric acid in 0.5M $Na_2SO_4$, and heated in boiling water for 15 minutes. After the solution was cooled, 1 ml of the solution was taken out and mixed with 1 ml of cyclohexanone. The mixture was shaken and centrifuged, and the upper layer was taken for the measurement at 549 nm.

CMP-NeuAc was isolated by affinity chromatography using the anti-decapeptide antibody or Orange A (Amicon C., Danvers, Mass.) as ligand followed by gel filtration. Huse et al., *Science*, 246:1275 (1989). The cell free extract (30 mL) obtained as described above was passed through an Orange A Dye column (1.5 mg/ml gel, 3cm×30cm) and washed with 200 ml of Tris buffer (0.2M Tris, 0.2 mM DTT and 2 mM $MgCl_2$, pH 7.5). The enzyme was eluted with a linear gradient from 0M KCl to 1M KCl in the same buffer. The active fraction was pooled and concentrated to 5 ml by ultrafiltration. The concentrated enzyme solution was then passed through an FPLC gel filtration column (Superose 12 h 10/30, Pharmacia Co.) at a flow rate of 0.2 ml/minute and the active fractions were collected. The protein concentration was determined by BCA assay kit (Pierce Co., Rockford, Ill.). The purity of the protein was judged by SDS PAGE (Phastsystem, Pharmacia Co.).

Example 3: Synthesis of a Sialyl Trisaccharide

Two procedures have been combined to synthesize a sialyl trisaccharide. The enzymatic aldol reaction (cycle B in Scheme 2) was first introduced to the Scheme 1: ManNAc was converted to NeuAc catalyzed by NeuAc aldolase (EC 4.1.3.3) in the presence of pyruvic acid. Although NeuAc aldolase also catalyzes the reverse reaction (NeuAc to ManNAc and pyruvate), the produced NeuAc is irreversibly incorporated into cycle A of Scheme 2 via CMP-NeuAc catalyzed by CMP-sialic acid synthetase coupled with inorganic pyrophosphatase (PPase)-catalyzed decomposition of the released inorganic pyrophosphate. The sialyl LacNAc was obtained in 89 percent yield after a Bio-Gel P-2 column chromatography. The experimental procedure is as follows:

To a 1.65 mL of HEPES buffer (200 mM, pH 7.5) were added ManNAc (43 mg, 180 mmol), LacNAc (22 mg, 60 mmol), CMP (2.0 mg, 6 mmol), ATP (0.32 mg, 0.6 mmol), PEP sodium salt (56 mg, 240 mmol), $MgCl_2.6H_2O$ (12.2 mg, 60 mmol), $MnCl_2.4H_2O$ (3.0 mg, 16 mmol), KCl (4.4 mg, 60 mmol), pyruvic acid sodium salt (33 mg, 300 mmol), NeuAc aldolase (EC 4.1.3.3; 45 U), MK (EC 2.7.4.3; 100 U), PK (EC 2.7.1.40; 120 U), PPase (EC 3.6.1.1; 6U, mercaptoethanol (0.22 mL), CMP-NeuAc synthetase (EC 2.7.7.43; 0.3 U in 1 mL of 0.1M Tris buffer, pH 9), and a(2,6)sialyltransferase (EC 2.4.99.1; 0.08 U). The final volume of the reaction mixture was 3 mL. The reaction was conducted at room temperature for two days under argon. After disappearance of the starting material judged by TLC ($R_f$: LacNAc, 0.63; NeuAc, 0.31; sialyl LacNAc; 0.30; CMP-NeuAc, 0.19 in 1M $NH_4OAc$/iPrOH 1:2.4, v/v), the reaction mixture was directly applied on a Bio-Gel P-2 (200–400 mesh) column (2×36 cm) and eluted with water. The trisaccharide-containing fractions were pooled and lyophilized to give sialyl LacNAc (37 mg, 89 percent)

The LacNAc synthesizing cycle (C in Scheme 2) and the above-mentioned cycle (A+B in Scheme 2) were also combined. The experimental procedure is as follows:

To a 2.6 mL of HEPES buffer (200 mM, pH 7.5) was added ManNAc (43 mg, 180 mmol), GlcNAc (13.3 mg, 60 mmol), Glc-I-P (21.5 mg, 60 mmol), CMP (2.0 mg, 6 mmol), UDP (2.8 mg, 6 mmol), ATP (0.32 mg, 0.6 mmol), PEP sodium salt (75 mg, 320 mmol), $MgCl_2.6H_2O$ (16.3 mg, 80 mmol), $MnCl_2.4H_2O$ (4.0 mg, 20 mmol), KCl (6.0 mg, 80 mmol), pyruvic acid sodium salt (33 mg, 300 mmol) NeuAc aldolase (45 U), (100 U), PK (120 U), PPase (12 U), mercaptoethanol (0.33 mL), galactosyl transferase (EC 2.4.1.22; 1 U), UDP-Glc pyrophosphorylase (EC 2.7.7.9; 1 U), UDP-Gal 4-epimerase (EC 5.1.3.2; 1 U), CMP-NeuAc synthetase (0.3 U in 1 mL of 0.1M Tris buffer, pH 9), and a (2,6) sialyltransferase (0.08 U). The final volume of the reaction mixture was 4 mL. The reaction was complete in two days, and pure sialyl LacNAc (9 mg; 22 percent) was isolated based on the above-mentioned procedure.

These data demonstrate the efficient synthesis of a sialyl trisaccharides starting from GlcNAc, ManNAc, Glc-I-P, and catalytic amounts of CMP, UDP (0.1 equivalents each) and ATP (0.01 equivalent) with no tedious separate preparations of sugar nucleotides, which are regenerated in situ. The pyruvate generated from PEP is used as a substrate in the NeuAc aldolase reaction.

Example 4: Synthesis of Monosaccharide Acceptors

A. 2-Acetamido-3-O-acetyl-2-deoxy-D-glucopyranose, Compound 1f

The synthesis of 2-acetamido-3-O-acetyl-2-deoxy-D-glucopyranose, Compound 1f, was accomplished by the scheme outlined below.

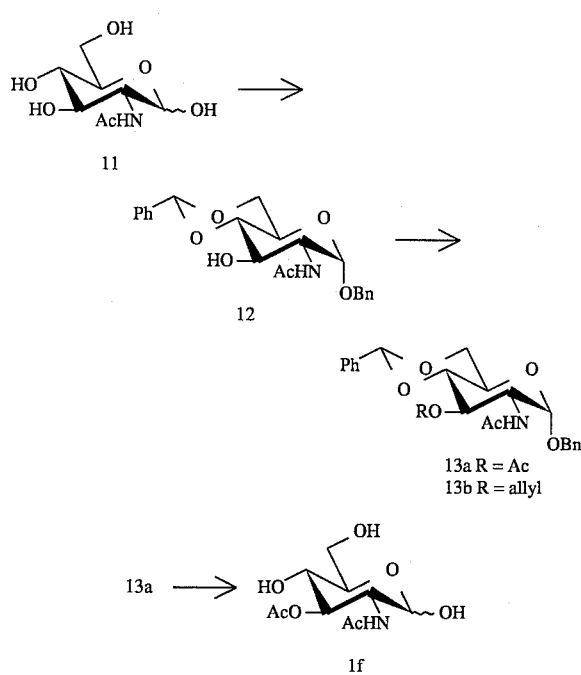

Compound 3.2 ( 2 g, 5 mmol), prepared from Compound 11 by standard procedures, was dissolved in 20 mL dry pyridine and treated with four equivalents (2.6 g) of acetic anhydride. The mixture was refluxed for 10 hours, then quenched with ice and extracted with chloroform. The extract was washed with 2N HCl (2×100 mL), water (50 mL) and brine (50 mL). After being dried over MgSO₄ and evaporation, the product, benzyl 2-acetamido-3-O-acetyl-4,6-O-benzylidene-2-deoxy-α-D-glucopyranoside, Compound 13a, was crystallized from ethyl acetate to yield 1.43 g (65 percent).

$^1$H NMR (d-6 acetone) δ1.93 (s, 3H, NHAc), 2.06 (s, 3H, COCH$_3$), 3.72–4.28 (m, 5H, H-2, 4, 5, 6a, 6b), 4.44, 4.68 (2d, J=14 Hz, 2H, CH$_2$Ph), 4.79 (d, J= 4 Hz, 1H, H-1), 5.08 (s, 1H, benzylic), 5.27 (dd, J=10 Hz, J=9.5 Hz, 1H, 3-H), 7.25–7.40 (m, 5H, Ar), 8.50 (d, J=9 Hz, 1H, NH).

Compound 13a (800 mg, 2 mmol) was dissolved in 100 mL of ethanol and 20 mL of acetic acid and the mixture was hydrogenated under 50 psi at room temperature using 250 mg of five percent Pd/C. After filtration through Celite, evaporation, and column chromatography, Compound 1f (350 mg, 67 percent) was obtained and further crystallized from methanol/ethyl ether.

$^1$H NMR (D$_2$O) δ1.94 (s, 3H, OAc), 2.06 (s, 3H, NAc), 3.36 (ddd, J=9, 5, and 2.5 Hz, H-5b), 3.51 (t, J =9.5 Hz, H-4b), 3.56 (t, J=9.5 Hz, H-4a), 3.72 (dd, J =12, 5 Hz, H-6.a) , 3.78 (dd, J=12, 2.5 Hz, H-6ba) , 3.87 (ddd, J=9.5, 5 and 2.5 Hz, H-5a), 4.05 (dd, J= 0.5, 3.5 Hz, H-2a), 4.72 (d, J=9 Hz, H-1b), 4.95 (dd, J=10.5, 9 Hz, H-3b), 5.07 (d, J=3.5 Hz, H-1a), 5.18 (dd, J=10.5, 9 Hz, H-3a). $^{13}$C NMR (D$_2$O) δ21.3, 22.7 (2CH$_3$), 53.2 (C-2), 61.3 (C-6), 68.7, 72.3, 74.8, 76.7 (C-3, C-4, C-5), 91.9, 95.9 (C-1), 174.8, 175.3 (2CO).

B. 2-Acetamido-2-deoxy-3-O-propyl-D-glucopyranose, Compound 1h

The synthesis of Compound 1h was accomplished by the scheme outlined below.

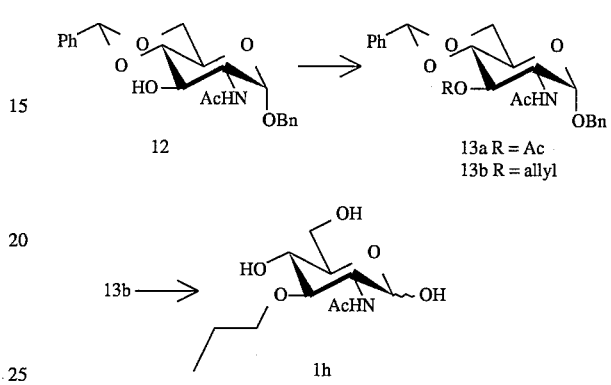

Compound 12 (2 g, 5 mmol) was dissolved in 30 mL THF. NaH (240 mg, 60 percent mineral oil dispersion, 1.2 equivalent) was added at zero degrees C and subsequently followed by 0.52 mL of allyl bromide (1.2 equivalents). The mixture was heated to reflux for 12 hours and then quenched with ice and NH$_4$Cl solution. After extraction with water (100 mL) and brine (50 mL), dried over MgSO$_4$ and evaporated. Recrystallization from ethyl acetate/hexane gave 1.32 g of Benzyl 2-acetamido- 3-O-allyl-4,6-O-benzylidene-2-deoxy-α-D-glucopyranoside, Compound 13b (60 percent).

$^1$H NMR (d-6 acetone) 6 1.85 (s, 3H, NHAc), 3.60–4.30 (m, 8H, H-2, 3, 4, 5, 6a, 6b, CH$_2$ of allyl), 4.50, 4.72 (2d, J=15 Hz, CH$_2$Ph), 4.81 (d, 1H, J=4 Hz, 1H, H-1), 5.03–5.25 (m, 2H, CH$_2$=C of allyl), 5.13 (s, 1H, benzylic), 5.75–5.96 (m, 1H, CH=of allyl), 7.30– 7.50 (m, 5H, Ar), 8.12 (d, J=9 Hz, 1H, NH).

Compound 13b (440 mg) was dissolved in 10 mL of ethanol and 5 mL of cyclohexane. 100 mg of PdO was added and the mixture was refluxed for 16 hours. The catalyst was removed by filtration and the filtrate was evaporated. After column chromatography with silica gel (CHCl$_3$/methanol/hexane 6:2:1) , Compound 1h was obtained (120 mg, 46 percent).

$^1$H NMR (D$_2$O) δ0.92 (t, J=7 Hz, 3H, CH$_3$), 1.56 (m, 2H, H-2'$_x$), 1.96 (s, 3H, NHAc), 3.23–3.85 (m, 7H, H-3, 4, 5, 6, 1'), 3.93 (dd, J=9 Hz, J=4 Hz, H- 2a) 4.58 (d, J=8 Hz, H-1b), 5.02 (d, J=4 Hz, H-1a).

C. Methyl 2-acetamido-3-O-allyl-2-deoxy-α-D-glucopyranoside, Compound 1g

The synthesis of Compound 1g was accomplished by the scheme outlined below.

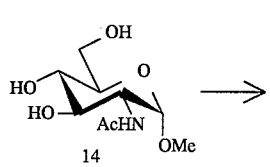

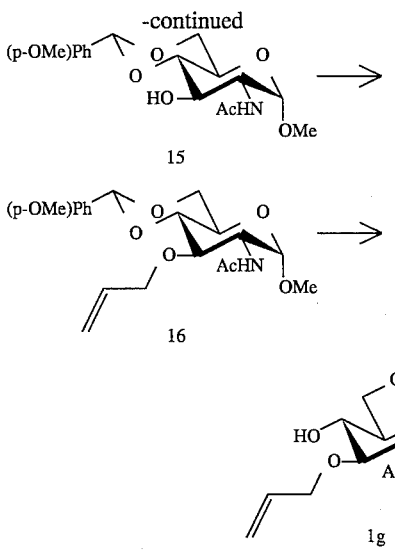

Compound 1.6 (500 mg, 1.15 mmol) prepared from Compound 14 via Compound 15 by standard protection and alkylation methods, was dissolved in 4 mL of concentrated acetic acid. The solution was stirred for 2 hours at 80° C. After evaporation of the acetic acid the residue was purified by column chromatography (ethyl acetate/methanol 20:1) on silica gel to yield 157 mg (50 percent) of Compound 1g.

$^1$H NMR (d-5 pyridine) δ2.16 (s, 3H, NHAc), 3.32 (s, 3H, Ar-OMe), 3.66 (s, 3H, C-I-OMe), 3.80–4.08 (m, 5H, 3-H, 4-H, 5-H, 6-H2), 4.35 (dd, J=9.5 Hz, J= 4.5 Hz, 1H, 2-H), 4.16–4.60 (m, 2H, CH$_2$ of allyl), 4.78– 4.90 (m, 1H, 5-H), 5.04–5.40 (m, 2H, CH$_2$=C), 5.74 (s, H, benzylidene), 5.90–6.10 (m, 1H, CH=C of allyl), 7.00–7.70 (m, 4H, ar), 8.95 (d, J=9 Hz, NH).

D. Allyl 2-acetamido-2,3-dideoxy-β-D-glucopyranoside, Compound 1i

The synthesis of Compound 1i was accomplished by the scheme outlined below.

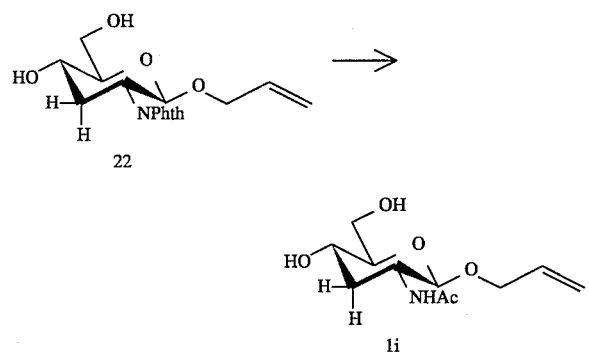

A mixture of allyl 2,3-dideoxy-2-phthalimido-β-D-glucopyranoside, Compound 22, (100 mg, 0.30 mmol) and BuNH$_2$ (4 mL) in MeOH (20 mL) was refluxed for 10 hours, then cooled and evaporated. Acetic anhydride (2 mL) was added to a solution of the residue in MeOH (10 mL) at 0°–5° C. and the mixture was stirred for three hours at 0°–5° C. The mixture was concentrated, and the residue was triturated in MeOH with Et$_2$O to give Compound 1i (40 mg, 54 percent).

$^1$H NMR (D$_2$O) δ1.52 (1 H, q, J=12.35 Hz, H- 3ax), 1.98 (3 H, s, NHAc), 2.25 (1 H, dt, J=4.76, 12.38 Hz, H-3eq), 3.39 (1 H, ddd, J=2.30, 6.44, 9.45 Hz, H-5), 3.59 (1 H, dt, J=4.79, 9.45 Hz, H-4), 3.65 (1 H, dd, J=6.44, 12.30 Hz, H-6a), 3.73 (1 H, ddd, J= 4.76, 8.45, 12.90 Hz, H-2), 3.84 (1 H, dd, J=2.30, 12.30 Hz, H-6b), 4.49 (1 H, J=8.45 Hz, H-1); $^{13}$C NMR (D$_2$O) δ22.30, 36.52, 49.24, 61.22, 64.57, 80.09, 102.03, 118.54, 133.67, 174.03; HRMS Calcd for C$_{11}$H$_{19}$NO$_5$Cs (M+Cs$^+$): 378. 0318. Found: 378. 0318.

E. Allyl 2-acetamido-2-deoxy-3-O-methoxycarbonyl-β-D-glucopyranoside, Compound 1k The synthesis of Compound 1k was accomplished by the scheme outlined below.

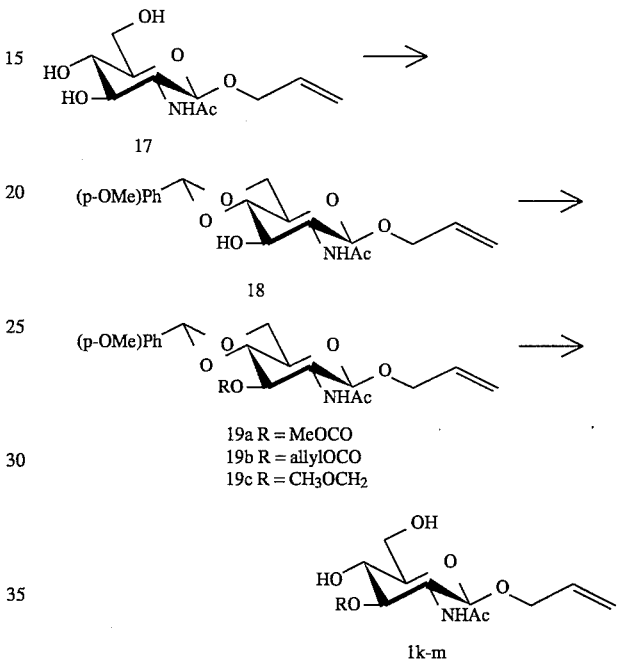

p-Methoxy benzaldehyde ( 30 mL) was treated with 5 g of dry ZnCl$_2$. After stirring for one hour, Compound 17 (4 g, 15 mmol) was added to the mixture at room temperature. The reaction mixture was stirred for 16 hours and then treated with 100 mL of CHCl$_3$ and 100 mL of water. The combined organic solutions were washed with 100 mL of brine and drying over MgSO$_4$. The solvent was removed in vacuo. The product was recrystallized from ethyl acetate/ hexane to yield 4.2 g (74 percent) of allyl 2 -acetamido-2-deoxy-4,6-O-p-methoxybenzylidene-β-D-glucopyranoside, Compound 18.

$^1$H NMR (d-5 pyridine) δ2.08 (s, 3H NHAc), 3.67 (s, 3H, OCH$_3$), 3.70 (ddd, J=9 Hz, J=4 Hz, J 32 2 Hz, 1H, 5-H), 3.98–4.03 (m, 2H, 6-H2), 4.27 (ddd, J= 12.5 Hz, J=5 Hz, J=1 Hz, 1H, CH$_{2a}$–C=C), 4.46 (dd, J =12 Hz, J=4 Hz, 1H, CH$_{2b}$–C=C) , 4.52–4.70 (m, 3H, 2-H, 3-H, 4-H), 5.13 (d, J=8.5 Hz, 1H, 1-H), 5.18 (dd, J= 9 Hz, J = 1 Hz, 1H, CH$_{2a}$=C) , 5.48 (dd, J=17 HZ, J=2 HZ, 1H, CH$_{2b}$=C), 5.77 (s, 1H, benzylidene), 5.98–6.14 (m, 1H, CH=C), 6.9514 7.60 (m, 4H, CH, ar), 9.10 (d, J=8 Hz, 1H, NH) .

Compound 18 (400 mg, 1.06 mmol) was dissolved in 3 mL of pyridine. At zero degrees C, 380 mg (4 equivalents) of methyl chloroformate were added. After stirring for 14 hours, the reaction was quenched with ice water. The precipitate was filtered off and washed extensively with water and ether. The remaining solid was dried and used without further purification to yield 395 mg of allyl 2-acetamido-2-deoxy-3-O-methoxycarbonyl- 4,6-O-p-methoxybenzylidene-β-D-glucopyranoside, Compound 19a (86.5 percent).

¹H NMR (d-5 pyridine) δ2.12 (s, 3H, NHAc), 3.60, (s, 3H, COOCH₃), 3.66–3.80 (m, 1H, 5-H), 3.85–4.08 (m, 2H, 6-H₂), 4.23–4.47 (m, 2H, CH₂–C=C), 4.45–4.55 (m, H, 4-H), 4.62 (ddd, J=9 Hz, J=8 Hz, 1H, 1-H), 5.15– 5.50 (m, 2H, CH₂=C), 5.20 (d, J=8 Hz, 1H, 1-H), 5.70 (s, 1H, benzylidene), 5.84 (dd, J=9.5 Hz, J=9.5 Hz, H, 3-H), 5.95 (m, 1H, CH=C), 6.90–7.6- (m, 4H, CH, Ar), 9.40 (d, J=8 Hz, 1H, NH).

Compound 19a (0.5 mmol) was treated with 2 mL of glacial acetic acid and stirred for 5 hours at 60° C. The acetic acid was removed in vacuo and the crude product, Compound 1k, was purified by column chromatography (silica gel, chloroform/MeOH/hexane= 6:1:1) .

¹H NMR (D₂O) δ1.82 (s, 3H, NHAc), 3.38 (ddd, J=10 Hz, J=4.5 Hz, J=2 Hz, 1H, 5-H), 3.53 (dd, J= 9.5 Hz, J=9 Hz, 1H, 2-H), 3.56–3.82 (m, 3H, 4-H, 6H₂), 4.02 (dd, J=13 Hz, J=6 Hz, 1H, CH₂–C=C), 4.20 (dd, J=13 Hz, J=5 Hz, 1H, CH₂ᵦ–C=C), 4.57 (d, J=8 Hz, 1H, 1-H), 4.66 (dd, J=10 Hz, J=9.5 Hz, 1H, 3-H), 5.07–5.22 (m, 2H, CH₂=C), 5.62–5.83 (m, 1H, CH=C). Yield: 112 mg, 70 percent.

F. Allyl 2-acetamido-3-O-allyloxycarbonyl-2-deoxy-β-D-glucopyranoside, Compound 1l The synthesis of Compound 1l was accomplished by a similar scheme to that outlined above in Example 5E.

Starting with 400 mg of Compound 18 and 480 mg of allyl chloroformate, allyl 2-acetamido-3-O-allyloxycarbonyl- 2-deoxy-4,6-O-p-methoxybenzylidene-β-D-glucopyranoside, Compound 19b was obtained. Yield: 347 mg, 71 percent.

¹H NMR (d-5 pyridine) δ2.16 (s, 3H, NHAc), 3.65 (s, 3H, OCH]), 3.65–3.75 (m, 1H, 5-H), 3.84–3.94 (m, 2H, 6Ha), 4.20–4.65 (m, 6H, 2-H, 4-H, 2CH₂–C=C), 4.95–5.49 (m, 5H, 2CH₂=C, 3-H), 5.22 (d, J=8 Hz, 1H, 1-H), 5.72 (s, 1H, benzylidene), 5.95–6.13 (m, 2H, CH=C), 7.00–7.70 (m, 4H, CH, Ar), 9.20 (d, J=8 Hz, 1H, NH).

Compound 19b (0.5 mmol) was treated with 2 mL of glacial acetic acid and stirred for five hours at 60° C. The acetic acid was removed in vacuo and the crude product Compound 1l, was purified by column chromatography (silica gel, chloroform/MeOH/hexane= 6:1:1).

¹H NMR (D₂O) δ1.76 (s, 3H, NHAc), 3.28–3.38 (m, 1H, 5-H), 3.42–3.76 (m, 4H, 2-H, 4-H, 6-H₂), 3.96 (dd, J=13 Hz, J=6 Hz, 1H, CH₂ₐ–C=C), 4.14 (dd, J= 13 Hz, J=5 Hz, 1H, CH₂ᵦ–C=C) , 4.50 (d, J=8 Hz, 1H, 1-H), 4.35–4.70 (m, 2H, CH₂–C=C, alloc), 5.0–5.18 (m, 5H, 2CH₂=C, 3-H), 5.60–5.84 (m, 2H, CH=C). Yield: 108 mg, 66 percent.

G. Allyl 2-acetamido-2-deoxy-3-O-methoxymethyl-β-D-glucopyranoside, Compound 1m

The synthesis of Compound 1m was accomplished by a similar scheme to that outlined above in Example 5E.

To a solution of Compound 18 (400 mg, 1.05 mmol) in 10 mL of THF were added 50 mg of NaH (60 percent in oil) at zero degrees C. After stirring for one hour, the reaction mixture was treated with 170 mg of chloromethylmethyl ether. The reaction was complete after 16 hours, and was quenched with water. The precipitate of allyl 2-acetamido-2-deoxy-3-O-methoxymethyl- 4,6-O-p-methoxybenzylidene-β-D-glucopyranoside, Compound 19c, was filtered off and washed with water and ether, and was used without further purification. Yield: 285 mg, 64 percent.

¹H NMR (d-5 pyridine) δ2.16 (s, 3H, NHAc), 3.45 (s, 3H, OCH3), 3.65 (s, 3H, ar-C-OCH₃), 3.65 (s, 3H, ar-C-OCH₃), 355–3.70 (m, 1H, 5-H), 3.80–3.94 (m, 2H, 6H₂), 4.18–4.55 (m, 4H, 2-H, 4-H, CH₂–C=C), 4.80–5.45 (m, 6H, CH₂=C, OCH₂O, 1-H, 3-H), 5.66 (s, 1H, benzylidene), 5.92–6.10 (m, 1H, CH=C), 6.90–7.65 (m, 4H, CH, Ar), 9.25 (d, J=8 Hz, 1H, NH).

Compound 19c (0.5 mmol) was treated with 2 mL of glacial acetic acid and stirred for five hours at 60° C. The acetic acid was removed in vacuo and the crude Compound 1m product was purified by column chromatography (silica gel, chloroform/MeOH/hexane= 6:1:1) .

¹H NMR (D₂O) δ1.80 (s, 3H, NHAc), 3.14 (s, 3H, OCH₃), 3.20–3.70 (m, 4H, 3-H, 4-H, 6-H₂), 3.92 (dd, J=13 Hz, J=6 Hz, 1H, CH₂ₐ–C=C), 4.10 (dd, J=13 Hz, J=5 HZ, 1H, CH₂ᵦ–C=C) , 4.35 (d, J=8 HZ, 1H, 1-H), 4.50 (d, J=7.5 Hz, 1H, OCH₂ₐO), 4.60 (d, J=7.5 Hz, 1H, OCH₂ᵦO), 4.98–5.14 (m, 2H, CH₂=C), 5.57–5.74 (m, 1H, CH=C). Yield: 110 mg, 72 percent.

H. 2-Acetamido-2-deoxy-D-allopyranose, Compound 1o

The synthesis of Compound 1o was accomplished by the scheme outlined below.

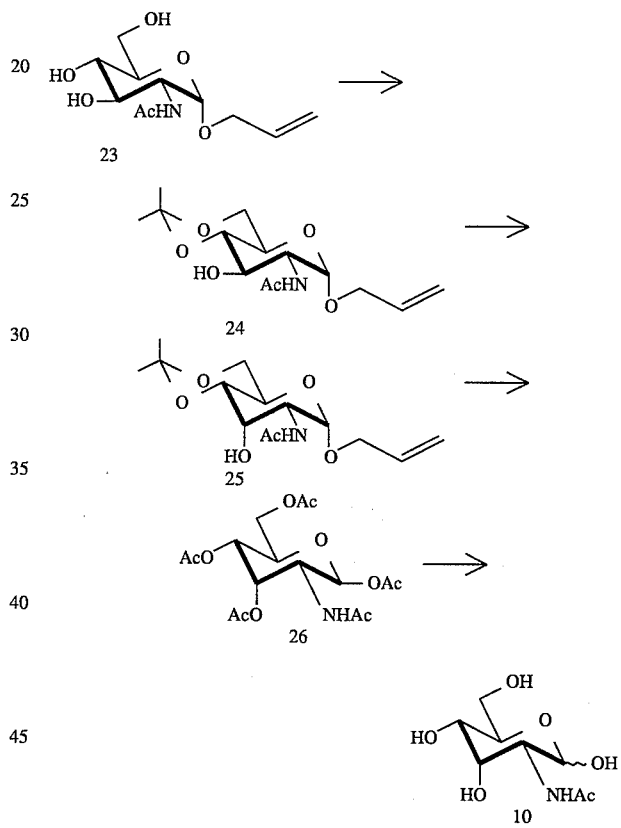

A solution of allyl 2-acetamido-2-deoxy-α-D-glucopyranoside, Compound 23, (2.95 g, 11.3 mmol), 2,2-dimethoxypropane (2,.35 g, 22.6 mmol; 2.78 mL) and p-toluenesulfonic acid monohydrate (172 mg, 0.90 mmol) in acetone (80 mL) was stirred for two days at room temperature. During this time, another amount of 2,2-dimethoxypropane (2.35 g, 22.6 mmol; 2.78 mL) was added to the mixture. After the addition of Et3N (1 mL), the mixture was concentrated in vacuo. The residue was chromatographed on silica gel, with toluene-EtOAc (1:2 1:3) to give allyl 2-acetamido-2-deoxy-4,6-O-isopropylidene-α-D-glucopyranoside, Compound 24 (2.26 g, 66 percent); mp 108.5°–109.0° C. (from EtOAc-hexane).

¹H NMR (CDCl₃) δ1.44, 1.53 (3 H, s, CH₃), 2.04 (3 H, s, NHAc), 4.84 (1 H, d, J=3.78 Hz, H-1); ¹³C NMR (CDCl₃) δ19.01, 23.24, 29.01, 54.00, 62.14, 63.44, 68.34, 70.56, 74.62, 96.94, 99.87, 118.05, 133.29, 171.37; HRMS Calcd for C₁₄H₂₃NO₆ (M⁺): 434.0580. Found: 434.0600.

A mixture of Compound 24 (1.0 g, 3.32 mmol) and Ac₂O (5 mL) in DMSO (10 mL) was stirred for 10 hours at room temperature, and poured into ice-cold aqueous NaOAc. The mixture was stirred for three hours, and extracted with CHCl₃. The extracts were successively washed with aqueous NaHCO₃ and water, dried over anhydrous MgSO₄, and concentrated. NaBH₄ (380 mg, 10.1 mmol) was added to a cooled solution of the residue in CH₂Cl₂ (10 mL), EtOH (10 mL), and water (2 mL) at 0°–5° C., and the mixture was stirred for 20 minutes at 0°–5° C. To the mixture were added acetone (5 mL) and saturated. NH₄Cl (5 mL), and the mixture was stirred for 10 minutes. The mixture was concentrated and the residue was dissolved in CHCl₃ and water, and the aqueous layer was extracted with CHCl₃. The extracts were washed with water, dried over anhydrous MgSO₄, and concentrated. The residue was chromatographed on silica gel, with toluene-EtOAc (1:3), to give allyl 2-acetamido-2-deoxy- 4,6-O-isopropylidene-α-D-allopyranoside, Compound 25, (612 mg, 61 percent); mp 113.5°–114.5° C. (from EtOAc-hexane).

¹H NMR (CDCl₃) δ1.45, 1.52 (3 H, s, CH₃), 2.04 (3 H, s, NHAc), 2.78 (1 H, d, J=6.78 Hz, OH), 3.68 (1 H, dd, J=2.77, 9.70 Hz, H-6a), 3.73–3.84 (1 H, m) , 3.90–4.04 (4 H, m, H-3,4, 6b, allylic), 4.24 (1 H, br dt, J=3.52, 8.97 Hz, H-2), 4.86 (1 H, d, J=3.97 Hz, H-1), 5.21–5.34 (2 H, m, vinylic of allyl), 5.81–5.87 (1 H, m, vinylic of allyl), 6.38 (1 H, d, J=9.13 Hz, NH); ¹³C NMR (CDCl₃) δ19.01, 23.16, 28.95, 49.42, 58.36, 62.33, 68.38, 69.06, 71.06, 97.15, 99.62, 118.32, 133.17, 169.66; HRMS Calcd for C₁₄H₂₃NO₆Cs (M+Cs⁺): 434.0580. Found: 434.0551.

A mixture of Compound 25 (489 mg, 1.62 mmol), PdCl₂ (317 mg, 1.79 mmol), and NaOAc (320 mg, 3.90 mmol) in AcOH (10 mL) and water (0.5 mL) was heated at 80° C. for 10 hours. After cooling, the mixture was filtrated through a Celite pad, and the filtrate was concentrated. The residue was chromatographed on silica gel, with CHCl₃-EtOAc-MeOH (5:2:1), to give the main product, which was acetylated with Ac₂O (5 mL) and pyridine (5 mL) to afford 2-acetamido-1,3,4,6-tetra-O-acetyl-2-deoxy-β-D-allopyranose, Compound 26 (142 mg, 23 percent) after recrystallization from EtOAc-hexane; mp 170.5– 171.0° C.

¹H NMR (CDCl₃) δ1.96, 1.98, 2.08, 2.13, 2.18 (3 H, s, 4× OAc, NHAc), 4.08–4.27 (3 H, m, H-5,6a,6b), 4.48 (1 H, dt, J=2.98, 9.20 Hz, H-2), 4.98 (1 H, dd, J =2.81, 9.87 Hz, H-4), 5.57 (1 H, br t, J=2.93 Hz, H-3), 5.56–5.61 (1 H, br s, NH), 5.89 (1 H, d, J=8.72 Hz, H-1); ¹³C NMR (CDCl₃) δ 20.42, 20.71, 20.93, 23.01, 49.39, 61.94, 66.18, 69.62, 70.96, 91.35, 169.04, 169.51, 169.71, 169.98, 170.68; HRMS Calcd for C₁₆H₂₃NOCs (M+Cs⁺): 522.0376. Found: 522.0376.

A mixture of Compound 26 (77 mg, 0.20 mmol) and methanolic NaOMe (1 mL; M solution) in MeOH (10 mL) was stirred for three hours at room temperature, and was neutralized with Dowex 50W-X8 [H⁺] resin. After the resin was removed by filtration, the filtrate was concentrated. The residue was triturated with MeOH and Et₂O to give Compound 1o (40 mg, 90 percent) as a fluffy solid (α/β=1:2.8).

¹H-NMR (D₂O) δ2.00 (s, NHAc of β-isomer), 2.02 (s, NHAc of α-isomer), 4.91 (d, J=8.72 Hz, H-1 of β-isomer), 5.09 (d, J=3.50 Hz, H-1 of α-isomer); ¹³C NMR (D2O) δ (β-isomer) 54.7, 61.6, 66.9, 70.2, 74.2, 92.8, 171.5; HRMS Calcd for C₈H₁₅NO₆Cs (M+Cs⁺): 353. 9954. Found: 353.9975.

I. Methyl 2-acetamido-2-deoxy-D-glucopyran- 3-uloside, Compound 1q

The synthesis of Compound 1q was accomplished by the scheme outlined below.

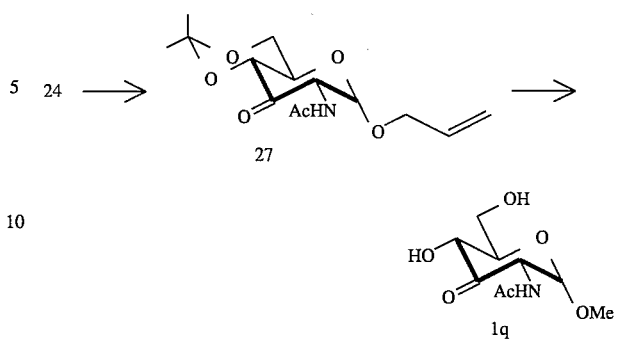

A mixture of Compound 24 (690 mg, 2.3 mmol) and Ac₂O (5 mL) in DMSO (10 mL) was stirred for 10 hours at room temperature, and poured into ice-cold aqueous NaOAc. The mixture was stirred for three hours at room temperature, and extracted with CHCl₃. The extracts were successively washed with aqueous NaHCO₃ and water, dried over anhydrous MgSO₄, and concentrated. The residue was chromatographed on silica gel, with toluene-EtOAc (1:4), to give the product, which was crystallized from EtOAc-hexane, to give allyl 2-acetamido-2-deoxy- 4,6-O-isopropylidene-α-D-glucopyran-3-uloside, Compound 27 (343 mg, 50 percent); mp 156.0°–156.5° C.

¹H NMR (CDCl₃) δ1.51, 1.53 (3 H, s, CH₃), 2.07 (3 H, s, NHAc), 3.92–4.03 (4 H, H-5, 6a, 6b, allylic), 4.11–4.20 (1 H, m, allylic), 4.39–4.51 (1 H, m, H-4), 4.95 (1 H, ddd, J=1.05, 4.25, 7.98 Hz, H-2), 5.18–5.34 (2 H, m, vinylic of allyl), 5.32 (1 H, d, J=4.25 Hz, H-1), 5.73–5.91 (1 H, m, vinylic of allyl), 6.34 (1 H, d, J=7.98 Hz, NH); ¹³C NMR (CDCl₃) δ18.72, 22.98, 28.77, 58.72, 62.65, 66.94, 68.80, 76.15, 100.15, 100.46, 118.32, 132.73, 170.04, 196.30; HRMS Calcd for C₁₄H₂₁NO₆Cs (M+Cs⁺): 432.0423. Found: 432.0438.

A mixture of Compound 27 (170 mg, 0.57 mmol), PdCl₂ (121 mg, 0.68 mmol), NaOAc (112 mg, 1.36 mmol) in acetic acid (10 mL) and water (0.5 mL) was heated at 80° C. for 10 hours. After cooling, the mixture was filtered through a Celite pad, and the filtrate was concentrated. The residue was chromatographed on silica gel, with CHCl₃-EtOAc-MeOH (5:2:1), during the column chromatography methyl glycoside was formed, to give the product, which was dissolved in water and lyophilized to give Compound 1q (55 mg, 44 percent).

¹H NMR (D₂O) δ2.042 (3 H, s, NHAc), 3.36 (3 H, s, OMe), 3.76–3.94 (3 H, m, H-5,6a,6b), 4.43 (1 H, dd, J = 0.95, 9.58 Hz, H-4), 4.90 (1 H, dd, J=0.98, 4.12 Hz, H-2), 5.16 (1 H, d, J = 4.08 Hz, H-1); ¹³C NMR (D₂O) δ22.00, 55.68, 59.53, 61.00, 72.49, 75.08, 100.85, 174.83, 204.65; HRMS Calcd for C₉H₁₅NO₆Cs (M+Cs⁺): 365.9954. Found: 365.9960.

J. Methyl 2-acetamido-2-deoxy-α-D-allopyranoside, Compound 1s

A solution of methyl 2-azido-4,6-O-benzylidene-2-deoxy-α-D-allopyranoside (200 mg, 0.65 mmol) and PPh₃ (208 mg, 0.79 mmol) in CH₂Cl₂ (10 mL) and water (0.5 mL) was stirred for four hours at room temperature, and the mixture was concentrated in vacuo. Active anhydride (2 mL) was added to a solution of the residue in MeOH (10 mL) at 0°–5° C. and the mixture was stirred for two hours at 0°–5° C. After the mixture was concentrated, the residue was chromatographed on silica gel, with toluene-EtOAc(1:2), to give 4,6-O-benzylidene derivative of Compound 21 (110 mg, 72 percent), which was treated with 80 percent AcOH (10 mL) for 3 hours at 80° C. After the mixture was concentrated and dissolved in Et$_2$O and water. The aqueous layer was washed with Et$_2$O, and the aqueous layer was concentrated. The residue was triturated with MeOH and Et$_2$O to give 1s (50 mg, 45 percent); [α]$_D$+77.9° (c 0.68, H$_2$O).

$^1$H NMR (D$_2$O) δ2.00 (3H, s, NHAc), 3.33 (3H, s, OMe), 3.62 (1H, dd, J=2.64, 9.39 Hz, H-4), 3.69–3.89 (3 H, m, H-5,6a,6b), 3.96–4.02 (2H, m, H-2,3), 4.71 (1H, d, J=3.76 Hz, H-1); $^{13}$C NMR D$_2$O) δ 22.22, 50.29, 55.84, 61.19, 66.44, 67.33, 69.63, 98.20, 174.19.

K. (2R) -methyl- ( 3R, 4R, 5S ) -trihydroxypiperidine; (1,5,6-Trideoxy-1,5-imino-D-glucitol), Compound 103c A solution of (R)-3-azido-2-hydroxypropanal diethyl acetal (Compound I; 480 milligrams (mg), 2.54 millimoles (mmol)) in 10 milliliters (mL) of a hydrogen chloride (HCl; pH 1) buffer solution was stirred at 70° C. for four hours. Gas chromatography analysis [J&W Scientific DB-5 column (15 m×0,522 mm), 40° C. for one minute to 250° C. at 20° C./minute] showed complete hydrolysis of the acetal (retention time of starting material 6.33 minutes, corresponding aldehyde 2.65 minutes). The solution was adjusted to pH 7, then DHAP (2 mmol) was added and the solution readjusted to pH 7. Rabbit muscle FDP aldolase (400 units) was then added, and the solution was stirred slowly for 36 hours. Enzymatic assay showed no DHAP remaining.

Barium chloride (BaCl$_2$. 2H$_2$O) [1.22 grams (g), 4.80 mmol] and two equivalent volumes of acetone were added to the solution. The solution was maintained at −20° C. for about 18 hours. The precipitate was recovered, and treated with Dowex X 50(H$^+$) in 20 mL water to remove barium cation. After filtration, the solution was adjusted to pH 7 and then lyophilized to obtain Compound 101c (550 mg, 1.79 mmol, 90 percent based on DHAP) as a white hygroscopic solid: R$_f$=0.46 percent palladium/carbon catalyst (Pd/C) under 45 pounds per square inch (psi) of hydrogen (H$_2$) for 18 hours. The catalyst was removed by filtration and the filtrate was concentrated and chromatographed on a short silica gel column [chloroform (CHCl$_3$): methanol (MeOH): H$_2$O= 5:5:2] to yield the title compound, Compound 103c (250 mg, 95 percent) as a white fluffy compound: R$_f$=0.60 (2-propanol: NH$_4$OH: H$_2$O=6:3:2); [α]$_D^{23}$+12.0° (c 2 5, H$_2$O); $^1$H-NMR D$_2$O) δ 1.10 (3H, d, J=6.4 Hz, CH$_3$), 1.27 (3H, d, J=6.8 Hz, 5-epimer-CH$_3$), 2.48 (1H, t, J$_{1a,1e}$= J$_{1a,2}$=12 HZ, H-1a), 2.63 (1H, dd, J$_{5,6}$=6.4, J$_{5,4}$=3.6 Hz, H-5), 3.03 (1H, t, J$_{3,4}$=J$_{4,5}$=9 Hz, H-4), 3.47– 3.52 (1H, m, H-2) ppm; $^{13}$C-NMR D$_2$O) δ 16.82, 48.22, 55.76, 69.98, 75.37, 77.83 ppm. HRMS (M+H$^+$) calculated 148.1001, found 148.0979.

L. (2R)-methyl-(3R,4R,5R)-trihydroxypiperidine; (1,5,6-Trideoxy-1,5-imino-D-mannitol), Compound 103a A solution of (S)- or (RS)-3-azido-2hydroxypropanal diethyl acetal (480 mg, 2.54 mmol) in 10 mL of the pH 1 buffer solution was stirred at 70° C. for four hours. Gas chromatography analysis (J&W Scientific DB-5 column (15 m×0.522 mm), 40° C. for one minute to 250° C. at 20° C./minute) showed complete hydrolysis of the acetal (retention time of starting material 6.33 minutes, corresponding aldehyde 2.65 minutes). The solution was adjusted to pH 7, then DHAP (2 mmol) was added and the solution readjusted to pH 7. Rabbit muscle FDP aldolase (400 units) was then added, and the solution was stirred slowly for 36 hours. Enzymatic assay showed no DHAP remaining.

Barium chloride (BaCl$_2$.2 H$_2$O) (1.22 g, 4.80 mmol) and two equivalent volume of acetone were added to the solution. The solution was maintained at −20° C. for about 18 hours. The precipitate was recovered, and treated with Dowex X 50(H$^+$) in 20 mL water to remove barium cation. After filtration, the solution was adjusted to pH 7 and then lyophilized to obtain the phosphorylated azidoketose.

A solution of this azido e-ketose phosphate in 10 mL of water was hydrogenated with 50 mg 10 percent Pd/C under 45 psi of hydrogen for 18 hours. The catalyst was removed by filtration and the filtrate was concentrated and chromatographed on a short silica gel column (CHCl$_3$:MeOH: H$_2$O= 5:5:2) to yield the title compound, Compound 103a: R$_f$0.12 (CHCl$_3$:MeOH: H$_2$O= 5:5:1.5); [α]$_D^{23}$ −4° (c=2.5, H$_2$O)

$^1$H-NMR D$_2$O) δ 1.213 (3H, d, J=6.5 Hz, CH$_3$), 2.893 (1H, dd, J$_{4,5}$=9.5 Hz, J$_{5,6}$=6.5 Hz, H-5), 3.00 (1H, d, J$_{1a,1e}$=13.5 Hz, H-1a), 3.16 (1H, dd, J$_{1e,1a}$= 3.5 HZ, J$_{13,2}$=3 HZ, H-1e), 3.45 (1H, t, J$_{13,2}$=J$_{2,3}$=3 HZ, H-2), 3.46 (1H, t, J=9.5 Hz, H-4), 3.675 (1H, dd, J$_{3,4}$=9.5 HZ, J$_{2,3}$=3 HZ, H-3) ppm; $^{13}$C-NMR (D$_2$O) δ 15.24 (CH$_3$), 48.31(C-1), 56.17(C-5), 66.74, 70.88, 72.92 ppm. HRMS (M+H$^+$) calculated 148. 0974, found 148.0900.

M. (2R)-Methyl-(3R,4R)-(5R)-N-acetylpiperidine; (1,5, 6-trideoxy-1,5-imino-N-acetylglucosamine; Compound 103b), and (2R)-methyl-(3R,4R)-dihydroxy-( 5S)-N-acetylpiperidine; (1,5,6-trideoxy- 1,5-imino-N-aceytylmannosamine; Compound 103d To a mixture containing 100 mL of dichloromethane ( CH$_2$Cl$_2$), 5.27 g ( 36.3 mmol) of (R) -2-(diethoxymethyl)aziridine (Compound II, 95 percent ee) and 40.0 g (289.4 mmol) of potassium carbonate (K$_2$CO$_3$) was added 4.0 mL (42.4 mmol) of acetic anhydride. The mixture was stirred at room temperature for 10 hours, filtered, and the filtrate was removed under reduced pressure. The residue was purified by silica gel column chromatography to yield 4.27 g of Compound IIIa: 63 percent yield; [α]$_D^{23}$ +84.23° (c 15, CHCl$_3$)

$^1$H-NMR (CDCl$_3$) δ 1.22, 1.25 (each 3H, t, J= 7.0 Hz, CH$_2$CH$_3$), 2.17 (3H, s, CH$_3$CO), 2.28 (1H, d, J= 3.3 Hz, CH$_2$ of aziridine) 2.35 (1H, d, J=6Hz, CH$_2$ of aziridine) , 2.68 (1H, m, CH of aziridine), 3.51–3.78 (4H, m, OCH$_2$), 4.40 (1H, d, J=4.5 Hz, CH(OEt)$_2$) ppm; $^{13}$C-NMR (CDCl$_3$) δ 15.6 (2C), 23.8, 27.7, 38.3, 63.2, 63.3, 101.6, 183.2 ppm. HRMS (M+H$^+$) calculated 188.1286, found 188.1290.

Compounds IIIb, IIIc and IIId were similarly prepared using appropriate blocking groups.

To a mixture containing 423.0 mg (2.26 mmol) of Compound IIIa and 1.9 g (29.5 mmol) of sodium azide in 18 mL of dimethyl formamide (DMF) was added 18.0 mL of zinc chloride [1.0M solution in ether], and the reaction mixture was stirred at 75° C. for three days. The mixture was extracted with ethyl acetate (EtOAc) and the organic layer was washed with water, dried over magnesium sulfate (MgSO$_4$) and concentrated. The residue was purified by silica gel chromatography (hexane: EtOAc = 3:2) to yield 318.6 mg of Compound Ira [61 percent yield, [α]$_D^{23}$ −23.8° (c 0 15, CHCl$_3$)].

$^1$H-NMR (CDCl$_3$) δ 1.23 (6H, t, J=7.1 Hz, CH$_2$CH$_3$), 2.03 (3H, s, CH$_3$CO), 3.45–3.61 and 3.66–3.76 (6H, m), 4.24 (1H, m, -CHNH), 4.53 (1H, d, J=3.9 Hz, -CH(OEt)$_3$), 5.83 (1H, d, J=7.8 Hz, -NH) ppm; $^{13}$C-NMR (CDCl$_3$) δ 15.5, 15.6, 23.7, 50.8, 51.0, 63.7, 64.4, 101.3, 170.5 ppm. HRMS (M + Cs$^+$) calculated 363. 0433, found 363. 0450.

The aldehyde liberated from racemic Compound IVa (1g) was mixed with 18 mL of DHAP (71.3 mmol), and the pH was adjusted to 6.5 with 1 normal (N) sodium hydroxide (NaOH). To this solution, rabbit muscle FDP aldolase (400 units) was added, and the mixture was stirred slowly for 4.5 hours. The mixture was passed through Dowex 1 (HCO$_2^-$) and eluted with water (400 mL) 0.1 molar (M) sodium chloride (NaCl; 250 mL), 0.4M NaCl (700 mL), and 0.5M NaCl solution, successively.

After adding 200 mL of water to the fraction eluted by the 0.4 M NaCl solution (700 mL) that contained Compound 101b, Pd/C (103.0 mg) was added, and the mixture was hydrogenated under the pressure of 50 psi for one day. The catalyst was filtered off and the filtrate was lyophilized. The residue was treated with a mixed solvent [chloroform ($CHCl_3$): methanol (MeOH): $H_2O$=6:4:1]. The soluble portion was collected and purified by silica gel chromatography ($CHCl_3$: MeOH: $H_2O$ =6:4:0.7) to yield Compounds 103b and 103d in a 12:1 ratio. Starting with enantiomerically pure aldehyde substrates, Compounds 103b and 103d were separately obtained.

Compound 103d: $^1$H-NMR $D_2O$) δ 1.33 (3H, d, J= 6.3 Hz, H-6), 1.94 (3H, s, $CH_3CO$), 2.85 (1H, t, J=12.5 Hz, H-1a), 3.10 (1H, m, H-5), 3.36 (1H, dd, J=12.5 and 4.9 Hz, H-1e), 3.39, 3.51 (each 1H, t, J=9.8 Hz, H-3,4), 3.99 (1H, ddd, J=12.5, 9.8 and 4.9 Hz, H-2) ppm; $^{13}$C-NMR $D_2O$) δ 14.8, 22.3, 44.0, 48.2, 54.9, 72.9, 73.1, 174.2 ppm. HRMS (M+Na$^+$) calculated 211.1059, found 211.1053.

Compound 103b: $^1$H-NMR $D_2O$) δ 1.34 (3H, d, J= 6.6 Hz, H-6), 1.97 (3H, s, $CH_3CO$), 3.10 (1H, m, H-5), 3.15, 3.43 (each 1H,dd, J=13.7 and 3.0 Hz, H-1), 3.62 (1H, t, J=9.4 Hz, H-4), 3.80 (1H, dd, J=9.4 and 4.6 Hz, H-3), 4.32 (1H, dt, J=4.6 and 3.0 Hz, H-2) ppm; $^{13}$C-NMR $D_2O$) δ 14.5, 22.4, 44.4, 47.6, 55.0, 69.9, 70.0, 174.7 ppm. HRMS (M+Na$^+$) calculated 211.1059, found 211.1050.

N. (1,2R)-dimethyl-(3R,4R,5S)-trihydroxypiperidine; (N-Methyl-1,5,6-trideoxy- 1,5-imino-D-glucitol), Compound 117

Compound 103c (47 mg, 0.32 mmol), formaldehyde (300 ml, 37 percent by weight solution) and 10 mg of 10 percent Pd/C were hydrogenated under 45 psi of hydrogen in 10 mL of MeOH/$H_2O$ (1:1) solution for one day. After filtration, the solvent was removed under reduced pressure to yield Compound 117 (52 mg, quantitative yield) as hygroscopic material: $R_f$=0.65 (2-propanol: $NH_4OH$: $H_2O$=6:3:2); [a]$_D^{23}$ +4.58° (c 1.75, $H_2O$)

$^1$H-NMR ($D_2O$) δ 1.12 (3H, d, J=6.5 Hz), 2.36 (1H, dd, J=11.5, 6.5 Hz), 2.63 (1H, d, J=5 Hz), 3.02– 3.06 (2H, m), 3.18 (1H, t, J=9.5 Hz), 3.48–3.53 (1H, m) ppm; $^{13}$C-NMR ($D_2O$) δ 16.96, 43.87, 61.17, 65.96, 0.68, 76.64, 79.95 ppm. HRMS (M+H$^+$) calculated 61.1052, found 162.1129.

O. (1,2R) -dimethyl-(3R, 4R, 5S)-trihydroxypiperidine oxide; (N-Methyl-1,5,6-trideoxy- 1,5-imino-D-glucitol oxide), Compound 118

Hydrogen peroxide (42 mg, 50 percent by weight solution) was added to a 1 mL $H_2O$ solution containing Compound 117 (10 mg, 0.062 mmol) and the mixture was stirred at room temperature for three days. The solvent was removed under reduced pressure to obtain pure Compound 118 (10 mg, 91 percent) as a single stereoisomer of white hygroscopic compound: $R_f$=0.53 (2-propanol: $NH_4OH$: $H_2O$=6:3:2); [a]$_D^{23}$ +5.40° (C 3.00, $H_2O$).

$^1$H-NMR ($D_2O$) δ 1.12 (3H, d, J=6.5 Hz, $CH_3$), 3.14 (1H, dd, J$_{5,4}$=10, $J$5, $CH_3$=6.5 Hz, H-5) , 3.20 (1H, t, J$_{2,3}$=J$_{3,4}$=10 Hz, H-3), 3.28 (1H, t, J$_{1a,1e}$=J$_{1a,2}$ 10 HZ, H-1a), 3.39 (1H, dd, J$_{13,1a}$=10, J$_{1e,2}$=5 Hz, H-1e), 3.41 (1H, t, J$_{3,4}$=J$_{4,5}$=10 Hz, H-4), 3.88 (1H, td, J$_{1a,2}$=J$_{23}$=10, J$_{2,1e}$=5 HZ, H-2) ppm; $^{13}$C-NMR $D_2O$) δ 8.65, 55.89, 67.85, 64.52, 70.21, 70.60, 75.44 ppm. HRMS (M+H$^+$) calculated 177.2009, found 177.2014.

P. (2S) -methyl-(3S, 4S, 5S )-trihydroxypiperidine; [1,6-L-rhamnanojirimycin (rhamnojirimycin)], Compound 106

To an aqueous solution of (RS) or (R)-3-azido- 2-hydroxypropanal, prepared by heating a suspension of 3-azido-2-hydroxypropanal diethyl acetal (1.1g, 5.8 mmol) in pH 1.0 buffer (40 mL) at 45° C. for 12 hours, were added DHAP (1.9 mmol) and Tris buffer (675 mM, KCl 750 mM, pH=7.5; 5.0 mL), and the pH value of the resulting solution was adjusted to 7.5 with 1N NaOH. To prepare a source for rhamnulose-1-phosphate aldolase, E. coli strain K-40 was treated with lysozyme (from egg white; 10 mg) in Tris buffer (45 mM, potassium chloride (KCl) 50 mM, pH= 7.5; 20 mL) for one hour at 35° C. One gram of this E. coli preparation was added to the above pH-adjusted solution, and the mixture was stirred slowly until 90 percent of DHAP was consumed.

After the reaction, the solution was adjusted to pH 7.0, $BaCl_2.2H_2O$ (950 mg, 3.9 mmol) was added, and the resulting precipitate was removed by centrifugation. Acetone (twice the volume) was added to the supernatant. The mixture was kept in a refrigerator for two hours and the precipitate newly appeared was collected. To remove the barium ion, Dowex 50 (H$^+$) was added with stirring followed by filtration. The solution was lyophilized and the residue was purified by silica gel chromatography ($CHCl_3$:MEOH: $H_2O$=8:2:0.1) to yield the phosphorylated azidoketose, Compound 104. 1

Compound '04 in ethanol (30 mL) containing Pd/C (20 mg) was hydrogenated at 50 psi for one day. The catalyst was filtered off and the filtrate was concentrated. The residue was purified by silica gel chromatography ($CHCl_3$:MeOH: $H_2O$=6:4:1~5:5:2) to yield Compound 106.

Compound 104a (dephosphorylated): Yield 55 percent (based on DHAP), $^{13}$C-NMR ($CD_3OD$) δ 54.6, 64.2, 76.8, 77.6, 81.1, 103.3 ppm.

Compound 106: $^1$H-NMR $D_2O$) δ 1.00 (3H, d, J=6.5, 5-$CH_3$), 2.30 (1H, m, H-5), 2.56 (1H, d, J=14.4, H-1a), 2.78 (1H, dd, J=14.4, 2.3, H-1e), 3.14 (1H, t, J=9.9, H-4), 3.35 (1H, dd, J=9.9, 2.9, H-3), 3.82 91H, bs, H-2) ppm; $^{13}$C-NMR ($D_2O$) δ 17.4, 48.6, 55.6, 69.8, 74.3, 74.5 ppm. HRMS (M+Cs$^+$) calculated 279. 9950, found 279.9950.

Q. (2R)-Methyl-(3S,4R,5S)-trihydroxypiperidine; (D-1, 6-D-dideoxygalactojirimycin), and (2S)-methyl-(3S, 4R,5S)-trihydroxypiperidine; (L-1,6-dideoxyaltrojirimycin), Compounds 110 and 109

To an aqueous solution of (RS)- or (R)-3-azido- 2-hydroxypropanal, prepared by heating a suspension of 3-azido-2-hydroxypropanal diethyl acetal (1.1g, 5.8 mmol) in pH 1.0 buffer (40 mL) at 45° C. for 12 hours, were added DHAP (1.9 mmol) and Tris buffer (675 mM, KCl 750 mM, pH = 7.5; 5.0 mL), and the pH was adjusted to 7.5 with 1N NaOH. To prepare a source for fuculose-1-phosphate aldolase, E. coli strain K-58 was treated with lysozyme (from egg white; 10 mg) in Tris buffer (45 mM, potassium chloride (KCl) 50 mM, pH=7.5; 20 mL) for one hour at 35° C. One gram of this E. coli preparation was added to the above pH-adjusted solution, and the mixture was stirred slowly until 90 percent of DHAP was consumed. E. coli fuculose-1-phosphate aldolase has been cloned and overexpressed, providing an alternate source for the enzyme [Ozaki et al., J. Am. Chem. Soc., 112:4970 (1990)].

After the reaction, the solution was adjusted to pH 7.0, $BaCl_2.2H_2O$ (950 mg, 3.9 mmol) was added, and the resulting precipitate was removed by centrifugation. Acetone (twice the volume) was added to the supernatant. The mixture was kept in a refrigerator for two hours and the precipitate newly appeared was collected- To remove the barium ion, Dowex 50 (H$^+$) was added with stirring followed by filtration. The solution was lyophilized and the residue was purified by silica gel chromatography ($CHCl_3$: MEOH: $H_2O$=8:2:0.1) to yield a phosphorylated azidoketose, Compound 108, in 20 percent (based on DHAP). Compound 108: $^{13}$C-NMR (CD$_3$OD) δ 52.7, 66.7, 71.9, 72.8, 80.1, 104.4 ppm.

A solution of Compound 108 in ethanol (30 mL) containing Pd/C (20 mg) was hydrogenated at 50 psi for one day. The catalyst was filtered off and the filtrate was concentrated. The residue was purified by silica gel chromatography (CHCl$_3$: MeOH: H$_2$O=6:4:1~5:5:2) to yield an approximately equimolar mixture of Compounds 109 and 110.

Compound 110: [α]$_D$ +18.2° (c 1.1, MeOH), $^1$H-NMR (D$_2$O) δ 1.20 (3H, d, J=6.7, 5-CH$_3$), 2.71 (1H, t, J=12.0, H-1a), 3.30 (1H, qd, J=6.7, 1.5, H-5), 3.31 (1H, dd, J=12.0, 5.5, H-1e), 3.50 (1H, dd, J=9.7, 3.0, H-3), 3.87 (1H, dd, J=3.0, 1.5, H-4), 3.90 (1H, ddd, j=11.5, 9.5, 5.5 Hz, H-2) ppm; $^{13}$C-NMR (D$_2$O) δ 14.4, 46.5, 55.3, 64.8, 70.3, 73.5 ppm. HRMS (M$^{+H+}$) calculated 148.0974, found 148.0974.

R. (2R)-Methyl-5-fluoro-(3R, 4R, 5R)-trihydroxypiperidine; (2,6-Dideoxy-2-fluoromannojirimycin), Compound 103e To a stirring solution of 3-azido-2-hydroxypropanal diethyl acetal (7.32 g, 38.73 mmol) in dry benzene (50 mL) was added diethylaminosulfurtrifluoride (DAST; 20.6 mL) at −78° C. After the addition, the solution was stirred at room temperature for an hour, then heated to 70° C. for 12 hours. The reaction was quenched by the addition of methanol at zero degrees C and diluted with water. After dichloromethane extraction, the organic layer was dried over MgSO$_4$ and concentrated in vacuo. The crude product was purified with silica gel column chromatography (hexane: ether=9:1, volume/volume) to yield 3-azido-2-fluoropropanal diethyl acetal as an oil (65 percent); R$_f$=0.84 EtOAc: hexane=2:3).

$^1$H-NMR (CD$_3$Cl) δ 1.215~1.219 (6H, m) 3.526 (2H, din, J=15.3 Hz), 3.642~3.670 (2H, m), 3.680~3.808 (2H, m), 4.514 (1H, dm, J=45.9 Hz) ppm.

A mixture of racemic 3-azido-2-fluoropropanal diethyl acetal (750 mg, 3.93 mmol) and 1N HCl (20 mL) was heated at 65° C. for 30 hours. The mixture was cooled to room temperature and DHAP (1 mmol) was added, and the pH value was adjusted to 7 with 10N NaOH. Rabbit muscle FDP aldolase (500 Units) was added to the pH-adjusted solution and the resulting solution was stirred slowly for 36 hours. Enzymatic determination indicated that all of the DHAP had been consumed. The solution was then filtered and lyophilized. The yellow syrup was treated with methanol and filtered to remove the insoluble material. The methanol was removed under reduced pressure to provide Compound A solution containing this product (20 mg) and 10 percent Pd/C (5 mg) in 10 mL methanol was hydrogenated at 50 psi for one day. The catalyst was filtered off and the solvent was removed under reduced pressure. The crude product was purified by silica gel column chromatography (CHCl$_3$:MeOH=3:1) to yield 2,6-dideoxy-2-fluormannojirimycin, Compound 103e.

S. 1,6-Dideoxyidojirimycin; Compound 111

Compound 111 is prepared in a manner similar to that used for the preparation of Compound 106 (Example 5) except that (S)-3-azido-2-hydroxypropanal is utilized with DHAP and rhamnulose-1-phosphate aldolase.

T. (3S, 4S)-Dihydroxypiperidine, Compound 114a; (3R, 4R)-dihydroxy-(6R)-methypiperidine, Compound 114b; (3S,4S)-dihydroxy-(5R)-methypiperidine, Compound 114c Compound 114a was produced by the DERA-catalyzed condensation of (RS)3-azido-2-hydroxypropanal, prepared as above, and acetaldehyde. Resulting Compound 113a was recoverd and hydrogenated over Pd/C as described before to provide Compound 114a.

Compound 114a: $^1$H-NMR D$_2$O) δ 1.51 (2H, m, H-2), 2.55 (1H, ddd, J=13.1, 7.6, 4.8, H-1), 2.67 (1H, dd, J=13.4, 3.0, H-5), 2.90 (1H, dd, J=13.4, 5.7, H-5), 2.86–2.96 (1H, m, H-1), 3.67 (1H, dt, J=5.9, 2.5, H-4), 3.74 (1H, ddd, J=7.6, 4.6, 3.0 H-3)ppm; $^{13}$C-NMR D$_2$O) δ 29.9 (C-2), 41.9 (C-1), 48.1 (C-5), 68.8, 69.3 (C-3, C-4) ppm. HRMS (M+): Calcuated: 117.0790, found 117.0785.

Compound 114a was produced by the DERA-catalyzed condensation of (RS)3-azido-2-hydroxypropanal, prepared as above, and acetone. Resulting Compound 113b was recovered and hydorgenated over Pd/C as described above to provide Compound 114b.

Compound 114b: $^1$H-NMR (CDCl$_3$) δ 1.05 (3H, d, J =6.3, H-1), 1.27 (1H, q, J=12.4, H-3a), 1.67 (1H, ddd, J=12.5, 4.7, 2.5, H-3e), 2.55 (1H, ddq, 12.6, 6.3, 2.5, H-2), 2.62 (1H, dd, J=13.4, 1.3, H-6a), 3.06 (1H, dd, J=13.4, 2.9, H-6e), 3.25 (3H, br s, 2 OH, NH), 3.53 (1H, ddd, J=11.9, 4.7, 3.0, H-4), 3.69 (1H, br s, H-5) ppm; $^{13}$C-NMR (CDCl$_3$) δ 22.1 (C-1), 37.7 (C-3), 50.1, 50.5 (C-2, C-6), 67.2 69.9 (C-4, C-5) ppm. HRMS (M+Cs$^+$): Calculated 264.0001, found 264.0000.

Compound 114c was produced by the DERA-catalyzed condensation of (RS)3-azido-2-hydroxypropanal, prepared as above, and propionaldehyde. Resulting Compound 113c was raecovered and hydrogenated over Pd/C as described above to provide Compound 114c.

Compound 114c: $^1$H-NMR D$_2$O) δ 0.91 (3H, d, J= 7.0, CH$_3$), 1.77–1.82 (1H, m, H-2), 2.45 (1H, t, J= 12.4, H-la), 2.67 (1H, t, J=11.7, H-5a), 2.70 (1H, dd, J=12.4, 4.8, H-1e), 2.90 (1H, dd, J=11.9, 4.6, H-5e), 3.72 (1H, ddd, J=11.7, 5.1, 3.0, H-4), 3.85 (1H, br s, H-3) ppm; $^{13}$C-NMR D$_2$O) δ 15.4 (CH$_3$), 35.5 (C-2), 44.8, 45.7 (C-1, C-5), 67.0, 72.6 (C-3, C-4) ppm. HRMS (M+Cs$^+$) Calculated 264.0001, found 264.0003.

Example 6. Inhibition Studies

A. Inhibition Study

Materials: All of the buffers, enzymes, and substrates were purchased from Sigma and used as received. These included piperazine-N,N'-bis(2-ethanesulfonic acid) (PIPES), sodium acetate (NaOAc), ethylenediaminetetraacetic acid (EDTA), β-D-glucosidase (from sweet almond), p-nitrophenyl β-D-glucoside, p-nitrophenyl α-D-glucosidase, p-nitrophenyl β-D-glucoside, β-N-acetyl-D-glucosaminedase, p-nitrophenyl β-N-acetyl-D-glucosaminide, α-D-mannosidase and p-nitrophenyl α-D-mannoside.

B. Preparation of solutions:

(a) PIPES buffer (0.05M with 0.01 mM EDTA, pH 6.5): To 1 liter (L) deionized H$_2$O were added 15.1 g PIPES and 35.7 mg EDTA. The pH was adjusted to 6.5 with NaOH (10M).

(b) PIPES-NaOAc buffer (0.01M PIPES, 0.2M NaOAc and 0.01 mM EDTA, pH 6.5). This buffer was prepared according to the literature procedure [Dale et al., Biochemistry, 24:3530 (1985)].

(c) β-D-Glucosidase: The stock enzyme solution was prepared by dissolving 15 mg of solid protein (4 units/mg) in 1 mL PIPES-NaOAc buffer solution. This stock enzyme solution was diluted 5-fold for the enzymatic assay.

(d) α-D-Glucosidase: 1.5 mg of solid protein (70 units/mg) were dissolved in 1 mL PIPES-NaOAc buffer solution and used for assays without further dilution.

(e) β-N-Acetyl-D-Glucosaminidase: 25 units of the protein were suspended in 0.55 mL of 3.2M ammonium sulfate [(NH$_4$)$_2$SO$_4$] solution as distributed by Sigma.

(f) α-D-Mannosidase: 5 mg of the solid protein were suspended in 1 mL of 3.0M (NH$_4$)$_2$SO$_4$ and 0.1 zinc acetate (ZnOAc), as distributed by Sigma.

(g) Substrate solutions: all substrates were dissolved in the corresponding buffer solution for enzymatic assay.

C. General Procedure for Enzyme Assay

For each inhibitor, five inhibitor concentrations, ranging from zero to three times $K_i$, were generally used to determine the $K_i$ value. At each inhibitor concentration, six substrate concentrations, spanning from 0.4 $K_m$ to 4 $K_m$, were used to obtain a single Lineweaver-Burk plot. The amount of enzyme added in each assay was adjusted so that less than 10 percent of the substrate, with its lowest substrate concentration, would be consumed within 45 seconds. Since all of the substrates have p-nitrophenol as leaving group, the assays were monitored at 400 nanometers (nm), where the molecular extinction coefficient, $\epsilon$, was calibrated to be $3204.5 M^{-1} cm^{-1}$ at pH 6.5. The following illustrates the detailed procedure.

To a 1 mL disposable cuvette were added 950 microliters (μL) of the NaOAc-PIPES buffer solution, 20 μL of the inhibitor solution and 20 μL of the p-nitrophenyl β-D-glucoside solution (100 mM in PIPES-NaOAc buffer, pH 6.5). The solution was well mixed and 20 μL of the β-D-glucosidase solution were injected into the cuvette to start the reaction. The reaction was monitored at 400 nm on a Beckman DU-70 photospectrometer for 45 seconds and the initial hydrolysis rate was calculated. The same procedure was repeated with five other substrate concentrations. After all the initial rates were accumulated, the corresponding Lineweaver-Burk plot at that inhibitor concentration was constructed.

PIPES-NaOAc buffer was used for all the enzymes except β-N-acetyl-D-glucosaminidase, for which PIPES buffer was used.

Exemplary $K_i$ data are provided in the Table 3, above.

Example 7: Expression of Galt in E. coli Strain JM109

The plasmid pIN-GT (See FIG. 1) in E. coli strain SB221 was isolated and transformed into strain JM109 (ATCC 53323) using a well known protocol. The transformants were introduced directly into 150 mL LB media and grown without induction overnight at 37° C. Cells were harvested by centrifugation at 4,000×g at 4° C. The cells were resuspended in 3 mL LB media and 1 mL chloroform was added. The mixture was allowed to stand at room temperature for 15 minutes before addition of 30 mL of 50 mM HEPES buffer, pH 7.4. Similarly, SB221 was freshly transformed and grown as a control. The enzyme was isolated and the activity was determined according to reported procedures.

Example 8: Studies with Focosyltransferase

Further studies of synthesis and inhibition using UDP-fucose as donor, fucosyltransferase and N-acetyllactosamine (Galβ1,4GlcNAc) as acceptor were carried out, as were inhibition studies with oligosaccharides. Those studies are discussed below.

A. Results

The $K_m$ for N-acetyllactosamine at 0.2 mM GDP-fucose was determined to by ±3 mM. Galactose β1,4-glucal (Table 1, from Compound 6) and 3-deoxy-N-acetyllactosamine (Table 1, Compound 1y) did not exhibit any inhibitory effect up to concentrations of 50 mg/mL under the described conditions. Galactose β1,4-5-thioglucose (Table 1, from Compound 5) proved to be a good substrate for fucosyltransferase in that a reaction with 5 mM of this compound reacted 2–5 times faster than N-acetyllactosamine. Galactose 1,4-deoxynojirimycin (Table 1, Compound 4) was an inhibitor of fucosyltransferase with an $IC_{50}$ approximately equal to 40 mM. During the course of these studies, it was noted that GDP-fucose exhibits very strong substrate inhibition against the synthesis of the trisaccharide. Assay for Fucosyltransferase The assay procedure for determining fucosyltransferase activity was essentially as described by Lowe et al., *Genes and Development*, 4:1288 (1990); Lowe et al, *Cell*, 63:475 (1990) with some minor modifications.

For some studies, a stock solution (mix A) containing 1 mM GDP-fucose, 67500 cpm $^{14}$C-GDP-fucose (Amersham Corp., 290 mCi/mmol), 25 mM ATP, 50mM fucose, and 250 mM sodium cacodylate buffer, pH 6.2 was mixed fresh the day of use and stored on ice.

A second set of solutions (mixes B1–B6) contained N-acetyllactosamine in varied concentrations from 1.5 to 50mM and 100 mM $MnCl_2$. These solutions were also made fresh each day and stored on ice. Assays proceeded by mixing 2 μL of mix A with 2 μL of one of the B mixes. To this solution, 5 μL of water were added followed by initiation of the reaction by addition of 1 μL enzyme solution. This assay mixture was gently mixed and allowed to incubate at 37° C. for 30 minutes.

For other studies, such as those using a recombinant fucosylα1,3/4transferase (EC 2.4.1.65) whose results are shown in Table 1a, a stock mixture containing 0.25 mM $^{14}$C-GDP-fucose (5000 cpm/μL), 6.25 mM ATP, 25 mMMnCl$_2$ are 62.5 mM cacodylate buffer, pH 6.2, was admixed fresh on the day of use, and stored on ice. To that solution, Fuc T was added immediately before use, and the reaction was initiated by the combination of 16 μL of that mixture with 4 μL of 100 mM acceptor substrate. The resulting admixture was then incubated at 37° C. for 30–240 minutes, depending upon the acceptor substrate (reactant compound) under study.

Simultaneous to these assays, another assay was performed and handled identically in the absence of lactosamine for determination of the background radioactivity either inherent in the study or from the generation of $^{14}$C-fucose by the action of some contaminating phosphatase.

Upon completion of the incubation, 400 μL of a 20 percent (v/v) suspension of QAE-Sephadex was added. These suspensions were gently mixed at room temperature for 10 minutes before centrifugation at 13,000 rpm for one minute. From the supernatant fluid, 100 μL were extracted and mixed with 10 mL of scintillation cocktail. The radioactive content was measured on a Beckmann LS1701 scintillation counter. Care was taken to insure that less than 10 percent of the enzymatic reaction had taken place over the 30 minute incubation period.

The Michaelis constant ($K_m$) for lactosamine in the presence of 0.2 mM GDP-fucose was determined by fitting the data to equation 1 by nonlinear regression analysis.

$$v=(V_{max})S/(K_m+S) \qquad \text{equation 1}$$

In the above equation, v=reaction rate, $V_{max}$=maximal velocity, and S=N-acetyllactosamine concentration.

Inhibition studies were carried out in an analogous manner in the presence of 2 mM N-acetyl-lactosamine and varied concentrations from 1 to 50 mg/mL of (a) galactosylβ1,4glucal (Compound 8), (b) galactosylβ1,4deoxynojirimycin (Compound 10a, (c) galactosylβ1,4-5-thioglucose (Compound 7), and (d) 3-deoxy-N-acetyllactosamine (Compound 2i). Percent inhibition was calculated as the fraction of inhibited activity to the uninhibited reaction rate. These fractions were plotted verus inhibitor concentration. The data was fit to a straight line (equation 2) by linear regression, and 50 percent inhibitory concentration ($IC_{50}$) was extrapolated from this line as the inhibitor concentration that would give 50 percent inhibition of the fucosyltransferase reaction. In this equation, m=slope and b=y-intercept.

*Percent inhibition=m([inhibitor])+b*     equation 2

The results of these assays are shown in Table 1a.

Example 9: Comparison of Native and Modified CMP-sialic acid synthetase enzymes

A. Preparation of enzymes

1. Construction of plasmids for the native and modified CMP-N-sialic acid synthetase enzymes The 1.3 kb NeuAc gene coding for the native CMP-sialic acid synthetase was amplified by PCR using the primers shown below as SEQ ID NO's: 4 and 5 with pWA1 plasmid DNA as a template. Innis et al., *PCR Protocols, A guide to methods and applications;* Academic Press, San Diego, Calif. (1990).

Forward Primer     (SEQ ID NO: 4)
5' ATATTGAATTCAGAAGGAGATATACATATG
    Eco RI    Rib           Start AGAACAAAAATTATT 3'
    gene N-terminal Reverse Primer     (SEQ ID NO: 5)
5' GCGCAAGCTTCATTTAACAATCTCCG 3'
    Hind III    gene C-terminal The PCR product was purified by phenol extraction followed by gel filtration on a Bio Gel P-10 spin columns in TE buffer. The purified oligonucleotide was digested with Eco RI and Hind III and purified by an agarose gel electrophoresis in low melting point agarose. This fragment was then ligated into plasmid pKK 223-3 under the control of the tac promotor. Zapata et al., *J. Biol. Chem.*, 264:14769 (1989) and Tabor et al., *Proc. Natl. Acad. Sci. USA*, 82:1074 (1985). This plasmid was designated pWG123. Plasmid pWG123 was then transformed into *E. coli* Sure strain obtained from Stratagene Co.

The construction of plasmid CMPSIL-1, which contains the modified CMP-NeuAc synthetase gene (Example 2), was accomplished by the method of Ichikawa et al., *J. Am. Chem. Soc.*, 113:4698 (1991). The CMP-NeuAc synthetase gene was fused with the decapeptide tag sequence Tyr-Pro-Tyr-Asp-Val-Pro-Asp-Tyr-Ala-Ser (SEQ ID NO:3) at the C-terminus, cloned into a lambda ZAP™ vector at EcoRI and XbaI sites and overexpressed in *E. coli* Sure strain.

To subclone the native CMP-sialic acid synthetase gene insert (without the decapeptide tag sequence) into plasmid CMPSIL-1, primer CMP5 (SEQ ID NO:1) in Table 4 was used for the forward primer and the primer shown below (SEQ ID NO:6) was used as the reverse primer in PCR as described previously.

Reverse Primer     (SEQ ID NO: 6)
5' GCGCTCTAGACTATTATTTAACAATCTCCGCTATT 3'
    Xba I    Stop       gene C-terminal The amplified PCR inserts and CMPSIL-1 plasmid were then digested with Eco RI and Xba I (40 U/mg DNA) for one hour at 37° C. and the digested DNA purified on 1 percent agrose gel. The purified native CMP-sialic acid synthetase gene insert and digested CMPSIL-1 plasmid were ligated with T4 DNA ligase (4U from Stratagene Co.) at 4° C. overnight (about 18 hours) to form plasmid CMPSIL-W10.

The above procedure thus produced a second phagemid (CMPSIL-W10) fromn CMPSIL-1 whose DNA was identical to that of CMPSIL-1 except for the absence of a sequence encoding the decapeptide tag.

The plasmid CMPSIL-W10 was then transformed into *E. coli* Sure strain and plated on LB agar plates containing 250 mg/mL ampicillin. The positive clones were selected by the assay of CMP-NeuAc synthesis activity after growth on LB medium and induced with IPTG as discussed in Example 2. The resulting *E. coli* Sure strain containing phagemid CMP-SIL-W10 produced native or wild-type CMP-Sialic acid synthetase in an amount of about 35 U/L.

The bacteria that harbored plasmids were grown on LB rich media (Bacto Trypton, 25 g; yeast extract, 10 g; NaCl, 3g; pH 7.0 in 1 L) containing 250 mg/ml ampicillin to mid-logarithmic phase ($OD_{660}$ about 0.6–0.7) at 37° C., and then induced with 0.5 mM IPTG (isopropyl β-D-thiogalactopyranoside) for 10 hours at 30° C. with shaking. The cells were harvested by centrifugation (10,000×g, 20 minutes, 4° C.) and disrupted by a French pressure cell at 16,000 lb/in$^2$. The cell debris was removed by centrifugation at 23,000×g for 60 minutes and the supernatant (cell free extract) was used for enzyme purification.

The cell free extract (30 mL) from 1 liter of culture was passed through the Orange A Dye column (1.5 mg/mL gel, 3 cm×30 cm) and washed with 200 mL of 0.2M Tris/HCl buffer containing 0.02M $MgCl_2$ and 0.2 mM dithiothreitol (DTT), pH 7.5. The enzyme was eluted with a linear gradient from zero to 1M KCl in the same buffer (total 200 mL). The active fractions were pooled and dialyzed in 2 L of 0.2M Tris/HCl buffer (pH 7.5) containing 0.02M $MgCl_2$ and 0.2 mM DTT. This enzyme preparation was used for synthesis directly. The enzyme was further purified tOTabOUt 95 percent purity by FPLC using a Superose 12 HR 10/30 column from Pharmacia for use in kinetic studies.

2. Kinetic studies

The activity of the native or the modified CMP-NeuAc synthetase was assayed using a thiobarbituric acid method described by Vann et al., *J. Biol. Chem.*, 262:17556 (1987). Briefly, the enzyme was added to a 250 mL buffer containing 5.5 mM CTP, 2.8 mM N-acetylneuraminic acid, 0.2M Tris, 20 mM $MgCl_2$ and 0.2 mM DTT, pH 9.0, to form a mixture. After the mixture was incubated at 37° C. for 30 minutes, 50 mL of 1.6M $NaBH_4$ was added to destroy excess NeuAc, and the mixture was heated at room temperature for an additional 15 minutes. The mixture was then put in the ice bath and 50 mL of $H_3PO_4$ were added to destroy $NaBH_4$.

The resulting mixture was kept at zero degrees C for five minutes then incubated at 37° C. for 10 minutes to cleave the phosphoester bond of the formed CMP-NeuAc. The free NeuAc was oxidized with 50 mL of 0.2 M $NaIO_4$ at room temperature for 10 minutes, and 400 mL of 4 percent $NaAsO_2$ in 0.5 N HCl were added. The solution mixture was the transferred to a test tube containing 1 mL of 0.6 percent thiobarbituric acid in 0.5M $Na_2SO_4$, and heated in boiled water for 15 minutes. After the solution was cooled, 1 mL of the solution was taken out and mixed with 1 mL of cyclohexanone. That mixture was shaken and centrifuged, and the upper layer was taken for measurement at 549 nm (e=4.11 $mM^{-1}cm^{-1}$).

Initial velocities were measured at various concentrations of CTP (1.25–5 mM) and NeuAc (2–8 mM) for kinetic studies. The data were fitted into the sequential bi-bi substrate rate equation 3, shown below, to derive the Michaelis constants and maximum velocity (V) using a Sigma plot program from Sigma Co.

$$v = \frac{VAB}{AB + K_aB + K_bA + K_{ia}K_b} \qquad \text{equation 3}$$

where A is [CTP], B is [NeuAc], $K_a$ and $K_b$ are the Michaelis constants for CTP and NeuAc, respectively, and $K_{ia}$ is the dissociation constant (or inhibition constant) for CTP.

The specific activities and kinetic constants of the two enzymes were found to be very similar. The native and the modified enzymes had specific activities of 2.1 U/mg and 2.3 U/mg, respectively. For the native enzyme, the $k_{cat}$ was 1.8 s$^{-1}$ and the values for the two substrates, NeuAc and CTP, were 4 mM and 0.31 mM, respectively. The tagged enzyme had a $k_{cat}$ of 1.9s$^{-1}$ and $K_m$'s of 4.8 mM and 1.99 mM, respectively, for NeuAc and CTP.

3. Enzyme stability.

The native and modified enzymes were incubated at room temperature in a 0.2M Tris buffer, pH 7.5, containing 0.02M MgCl$_2$ and 0.2 mM dithiothreitol. At defined time intervals, 30 mL aliquots were removed and assayed for activity as described above. Enzyme stabilities were studied for a period of three days. The native enzyme has a half life of about 800 hours in a phosphate buffer (pH 7.5) at room temperature. On the other hand, the modified enzyme has a half life of about 80 hours, approximately 10 times less stable than the native, wild type.

4. pH profile.

Both enzymes were assayed for the activity in 0.2M Tris buffers, from pH 8 to pH 10.8, and in 50 mM sodium cacodylate buffers, from pH 4.5 to pH 7.5. These buffers were prepared in the presence of 20 mM MgCl$_2$ and 6 mM MnCl$_2$ separately, containing 0.2 mM dithiothreitol. The assay solution containing 5.5 mM CTP and 2.8 mM NeuAc was incubated at 37° C. for 30 minutes, and the amounts of CMP-NeuAc formed were determined based on the thiobarbituric acid assay.

The enzyme activities were studied at various pH values, from pH 4.5 to 10.5, in the presence of two different metal ions, Mg$^{2+}$ and Mn$^{2+}$, which were known to affect the enzyme activity. Similar to the enzyme isolated from the mammalian tissue, the native microbial CMP-sialic acid synthetase was found to have an optimum pH at pH 7 5 in the presence of Mn$^{2+}$, and at pH 9 5 in the presence of Mg$^{2+}$. The tagged enzyme, however, showed an optimum activity at pH 9.5 in the presence of either Mg$^{2+}$ or Mn$^{2+}$.

5. Substrate specificity.

In 250 mL assay solution contained 2.8 mM of each substrate, 5.5 mM CTP, CMP-NeuAc synthetase and 0.2 M Tris buffer with 20 mM MgCl$_2$ and 0.2 mM DTT at pH 7.5 and pH 9.0. The incubation time varied from 15 minutes to five hours depending on the activity of the enzymes toward the substrate analogs. The formation of CMP-NeuAc derivatives was determined by thiobarbituric acid assay.

cMP-sialic acid synthetase from a variety of mammalian tissues was found to be specific for CTP and sialic acids. It accepts some C-9 and C-8 modified sialic acid analogs including fluorescent probesattached at the 9-position. The enzyme from the mammalian system also accepts C-5 modified substrates such as KDN and 5-N-glycolylneuraminic acid as substrates. See, e.g. Shames et al., *Glycobiology,* 1:87 (1991); Auge et al., *Tetrahed. Lett.,* 29:789 (1988); Kean et al., *Methods Enzymol.,* 8:208 (1966); Roseman, S. *Proc. Natl. Acad. Sci.,* 48:437 (1962); Gross et al., *Eur. J. Biochem.,* 168:595 (1987); and Gross et al., *Eur. J. Biochem.,* 117:583 (1988).

The results of substrate specificity studies 10 for the native and modified recombinant CMP-NeuAc synthetase enzymes are summarized in Table 5, below.

TABLE 5

| | | Tagged enzyme | | Native enzyme | |
|---|---|---|---|---|---|
| | | pH 7.5 | pH 9.0 | pH 7.5 | pH 9.0 |
| 201 | (structure: HO-CH2, HO, AcNH, HO, O, COOH, OH) | 1 | 1 | 1 | 1 |
| 202 | (structure: AcO-CH2, HO, AcNH, HO, O, COOH, OH) | 0.98 | 2.26 | 0.92 | 0.48 |
| 203 | (structure: isobutyryl ester, HO, AcNH, HO, O, COOH, OH) | 0.92 | 1.7 | 0.95 | 0.46 |
| | (structure: N3-CH2, HO, AcNH, HO, O, COOH, OH) | 1.2 | 1.34 | 0.99 | 0.49 |

TABLE 5-continued

| | Tagged enzyme | | Native enzyme | |
|---|---|---|---|---|
| | pH 7.5 | pH 9.0 | pH 7.5 | pH 9.0 |
| 204 (structure) | 1.1 | 1.2 | 0.98 | 0.52 |
| 205 (structure) | <0.05 | <0.05 | <0.05 | <0.05 |
| 206 (structure) | <0.05 | <0.05 | <0.05 | <0.05 |
| 207 (structure) | <0.05 | <0.05 | <0.05 | <0.05 |
| 208 (structure) | <0.05 | <0.05 | <0.05 | <0.05 |
| 209 (structure) | <0.05 | <0.05 | <0.05 | <0.05 |
| 210 (structure) | <0.05 | <0.05 | <0.05 | <0.05 |

The cloned enzymes from *E. coli* system have similar substrate specificity to the enzyme from mammalian systems. Several sialic acid analogs were synthesized and tested as substrates for the native and the tagged enzymes at pH 7.5 and pH 9.0.

Both enzymes have high activity for the C-9 modified sialic acid analogs (9-O-acetyl, 9-O-lactyl, 9-deoxy-9-fluoro, and 9-azido-9-deoxy NeuAc); however, the C-5 modified analogs (KDN, 5-deoxy KDN and 10 5-deacetamido-5-epi-5-fluoro NeuAc) were not substrates. These results suggest that the 5-acetamido group of the sialic acids is critical for the substrate recognition by the microbial enzymes.

Although both microbial enzymes have very similar substrate specificity at pH 7.5, they have different specificity at pH 9.0. At pH 7.5, the native enzyme was found to be specific for NeuAc; the relative rates for the C-9 modified NeuAc derivatives decreased to about 50 percent. On the contrary, the relative rates of the C-9 modified analogs for the tagged enzyme are higher than that of N-acetylneuraminic acid (Table 5).

The C-5 and C-9 modified sialic acid derivatives used in this study were prepared via sialic acid aldolase-catalyzed condensation with C-2 and C-6 modified N-acetylmannosamine (ManNAc) derivatives with pyruvate as set forth hereinafter in Example 10.

The 6-0-acylated ManNAc derivatives were prepared via transesterification in DMF catalyzed by a subtilisin variant (8399 or 8397) engineered to be stable in organic solvent. Zhong et al., *J. Am. Chem. Soc.*, 113:683 (1991). The wild type enzyme (BPN') can also be used but requires more amount of enzyme as the variant is about 100 times (for 8399) to 1000 times (for 8397) more stable than the wild type. It is thought that the enzymatic procedure described here for the preparation of 6-0-acyl sugars is much more effective than the reported chemical procedure. [For 9-O- acetyl-N-acetylneuraminic acid and 9-O-lactyl N-acetylneuraminic acid: (a) Auge et al., *Tetrahed. Lett.*, 25:4663 (1984) (6-O-acetyl-ManNAc was prepared chemically); (b) Kim et al., *J. Am. Chem. Soc.*, 110:6481 (1988) (6-O-acetyl-ManNAc was prepared via protease N reaction); (c) Auge et al., *New J. Chem.*, 12:733 (1988) (for 9-O-lactyl-NeuAc from chemically synthesized 6-O-lactyl-ManNAc)]; [For 9-azido-9-deoxy-N-acetylneuraminic acid: (d) Brossmer et al., *Biochem. Biophys. Res. Comm.*, 96:1282 (1980) (no physical data were reported)]; [For 3-deoxy-L-glycero-L-galactononulosonic acid (KDN): (e) Auge et al., *Tetrahedron*, 46:201 (1990)]; [For 3,5-dideoxy-L-glycero-L-galactononulosonic acid (5-deoxy-KDN): (f) Auge et al., *Tetrahed. Lett.*, 30:2217 (1989)].

Example 10: Preparation of sialic acid analogs

The C-5 and C-9 modified sialic acid derivatives used in the synthetase studies described in Example 9 were prepared via sialic acid aldolase-catalyzed condensation with C-2 and C-6 modified N-acetylmannosamine (ManNAc) derivatives with pyruvate. The 6-O-acylated ManNAc derivatives were prepared via transesterification in DMF catalyzed by a subtilisin variant (8399 or 8397) engineered to be stable in organic solvent. Zhong et al., *J. Am. Chem. Soc.*, 113:683 (1991). The wild type enzyme (BPN') can also be used but requires more amount of enzyme as the variant is about 100 times (for 8399) to 1000 times (for 8397) more stable than the wild type.

A. 9-O-Acetyl-N-acetylneuraminic acid (Compound 201)

In 2 mL of DMF were suspended 500 mg (2.2 mmol) of N-acetylmannosamine. Vinylacetate (1 mL, 5 equivalent) and 160 mg of subtilisin mutant 8399 [Zhong et al., *J. Am. Chem. Soc.*, 113:683 (1991)] were then added and the suspension was stirred vigorously at room temperature. The reaction progress was monitored by TLC with ethyl acetate/methanol (⅔). After 5 hours when the formation of the di-acetylated derivatives began, the reaction was stopped by evaporating the vinylacetate and DMF. Methanol was then added to dissolve the sugar. After the enzyme and salt were filtered off, the filtrate was concentrated. The residual syrup was chromatographed on a silica gel, with ethyl acetate/methanol (10/1) to give 6-O-Acetyl N-acetylmannosamine (92 percent) as α/β mixture (3:1) based on the NMR spectrum.

α-Anomer: $^1$H NMR (D$_2$O) δ 1.98 (3H, s, NAc), 2.06 (3H, s, OAc), 3.58 (1H, dd, J=9, 9 Hz, H-4), 3.96 (1H, dd, J=3.5, 9 Hz, H-3), 4.15–4.4 (4H, m, H-2,5,6,6'), 5.04 (d, J=0.9 Hz, H-1a). α/β mixture $^{13}$C NMR (D$_2$O) δ 23.1, 24.7, 56.1, 56.7, 66.5, 66.6, 69.7, 69.8, 71.3, 72.4, 74.6, 76.6, 95.8, 95.9, 176.7, 176.8, 177.6, 178.4. The product was identical to that prepared with protease N reaction.

In a 10 mL of 0.1M potassium phosphate buffer (pH 7.5) were dissolved 10 mM DTT, 0.5 M pyruvate, 100 mg of 6-O-acetylmannosamine, prepared as described above, and 1.5 mg NeuAc aldolase (36 U). The reaction mixture was incubated at 37° C. for 8 days followed by lyophilization. The lyophilized powder was dissolved in a small amount of water and directly applied to a Bio Gel P-2 column (3×90 cm) and eluted with a flow rate of 6 mL/40 minutes at 4° C. To remove the trace amount of contaminated NeuAc due to the hydrolysis of the product, another gel filtration was required. Compound 201 was obtained in 47 percent yield. Its physical data were consistent with the reported data.

B. 9-O-Lactyl-N-acetylneuraminic acid (Compound 202)

ManNAc (200 mg) and 50 mg of subtilisin mutant 8399 were added to a mixture of lactic acid ethyl ester (4 mL) and 400 mL of 0.5 N phosphate buffer (pH 7.5). The reaction mixture was shaken under 50° C. for three days. The solvent was then evaporated and methanol was added to the residue. After the insoluble materials were filtered off, the filtrate was concentrated. The residue was chromatographed on silica gel with ethyl acetate/methanol (5/1) to give 6-O-Lactyl N-acetylmannosamine in 50 percent yield.

$^1$H NMR D$_2$O δ 1.29 (3H, d, J=7 Hz,lactyl-CH$_3$), 1.91 (3H, s, OAc), 3.51 (1H, dd, J=9.5, 9.5 Hz, H-4), 3.92 (1H, dd, J=9.5, 4.2 Hz, H-3), 4.16 (1H, dd, J=1.8, 4.3 Hz, H-2), 4.2–4.4 (3H, m, H-5,6), 4.88 (d, J=0.9 Hz, H-1a), 4.97 (d, J=1.3 Hz, H-1b). $^{13}$C NMR D$_2$O δ 20.10, 22.76, 22.93, 54.17, 54.81, 65.1 67.6, 67.91, 69.43, 70.61, 93.87. HRMS calculated for C$_{11}$H$_{19}$NO$_2$ (M$^+$): 293.1111. Found: 293.1091.

The procedure used to prepare Compound 202 was the same as that used to prepare Compound 201, except that 6-O-Lactyl N-acetylmannosamine was used instead of 6-O-Acetyl N-acetylmannosamine. Another gel filtration purification was required to separate the product from NeuAc to give Compound 202 in 18 percent yield. The physical data of the product were consistent with the reported values.

C. 7,9-Difluoro-7-epi-5-deaminoneuraminic acid (Compound 205)

Compound 205 was prepared using the aldolase reaction described herein except that 4,6-dideoxy-4,6difluoroglucose was used as the substate.

HRMS: calcd 271.0625; found, 271.0649. $^1$H-NMR (500 MHz, D$_2$O) δ 4.7 (m, H-7), 4.5 (dd, H-9, J$_{H-F}$=47.5 Hz, J$_{H-H}$=3 Hz), 4.20 (td, H-8, J$_{H-F}$=18.5, J$_{H-H}$=3.0 HZ), 3.93 (m, H-6), 3.84 (m, H-4), 3.47 (t, H-5, J$_{H-H}$= 10.5 HZ), 2.12 (dd, H-3e, J$_{He-H4}$=2.6 Hz, J$_{He-H3}$=12.5 HZ), 1.74 (dd, H-3a, J$_{H-H4}$=12.5, J$_{H3a-H3e}$=12 HZ). Peak assignment was accomplished by the use of 2D technique.

D. 5-Epi-5-deamino-5-fluoro-neuraminic acid (Compound 206)

Compound 206 was prepared using the aldolase reaction described herein except that 2-deoxy-2-fluoroglucose was used as the aldolase substrate.

HRMS: calcd. 269.0673; found, 269.0651. $^{13}$C-NMR (D$_2$O, CD$_3$OD as standard) δ 174.5 (s, C-1), 96.4 (s, C-2), 34.5 (s, C-3), 65.5 (d, C-4, JC-4,F-5=18 Hz, 91.2 (d, C5, J$_{C-5,F-5}$=191 HZ), 70.7 (d, C-6, J$_{C-6,F-5}$=18 HZ), 71.9 (s, C-7), 72.8 (s, C-8), 63.5 (s, C-9).

E. 3-Deoxy-L-glycero-L-galacto-2-nonulosonic acid (KDN) (Compound 207)

To a 10 mL potassium phosphate buffer (0.1M, pH 7.5) were added 10 mM DTT, 0.5M pyruvate, 0.1M D-mannose and 1.5 mg NeuAc aldolase. The reaction mixture was shaken at 37° C. for three days. The reaction mixture was chromatographed with a Dowex-1 (HCO$_3^-$) resin, eluted with zero to 1M ammonium bicarbonate gradient. The fractions containing KDN were pooled and lyophilized three times repeatedly to remove the volatile salt to give a 78 percent yield of KDN. The physical data of the product were are consistent with the reported.

F. 3,5-Dideoxy-L-glycero-L-galacto-2-nonulosonic acid (5-deoxy-KDN) (Compound 208)

2-Deoxyglucose (0.1M) was added to the solution instead of D-mannose, and the preparation procedure was the same as above. The reaction mixture was shaken for five days and Compound 208 was obtained in 30 percent yield. The physical data of the product were consistent with the reported data.

G. 9-(Dimethylphosphinyl)-9-deoxy-N-acetylneuraminic acid (Compound 209)

A solution of ManNAc (5.0 g, 2.6 mmol), Ac$_2$O (10 mL)

and pyridine (20 mL) was stirred for 10 hours at room temperature, and the mixture was concentrated, followed by coevaporation with toluene. A solution of the residue, benzyl alcohol (20 mL), BF$_3$.OEt$_2$ (1.6 g, 11.3 mmol) in CH$_3$NO$_2$ (150 mL) was gently refluxed for 2.5 hours. After cooling, the mixture was concentrated. The residue was chromatographed on silica gel, with toluene-EtOAc (1:2). The isolated benzyl 2-acetamido- 4,5,6-tri-O-acetyl-2-deoxy-a-D-mannopyranoside and 0.15 g of NaOMe was dissolved in MeOH (100 mL) and the solution was stirred for 30 minutes at room temperature, and neutralized by addition of Dowex 50W-X8 (H$^+$). After the resin was filtered off, the filtrate was concentrated, followed by coevaporation with pyridine. A solution of dimethylphosphinic chloride (1 g, 8.8 mmol) in DMF was added to a cold solution of benzyl 2-acetamido-2-deoxy-a-D-mannopyranoside (0.50 g, 1.6 mmol), 2,6-lutidine (0.34 g, 3.2 mmol) in anhydrous DMF (30 mL) in a dry ice-acetone bath, and the reaction was allowed to slowly warm to room temperature. The reaction was monitered by TLC with (1M NH$_4$OAc/2-proponal/EtOAc, 1/2.4/3.4). After 10 hours, the reaction mixture was directly applied to silica gel chromatography, eluted with CHCl$_3$/EtOAc/MeOH (5/2/1) to give benzyl 2-acetamido-2-deoxy-6-(dimethyl-phosphinyl)-a-D-mannopyranoside (56 percent yield).

$^1$H NMR D$_2$O) δ 1.46 (3H, d, J=13.4 Hz, P-CH$_3$), 1.5 (3H, d, J=13.4 Hz, P-CH$_3$), 1.89 (3H, s, NAc), 3.53 (1H, dd, J=8, 8 Hz, H-4 ), 3.76 ( 1H, dd, J=8, 4.3 Hz, H-3), 4.0 (3H, m, H-5, 6), 4.18 (1H, d, J=4.3 Hz, H-2), 4.44 (1H, d, J=9.2 Hz, Bn-H-1a), 4.55 (1H, d, J=9.2 Hz, Bn-H-1b), 4.76 (1H, s, H-1), 7.28 (5H, s, Bn).

A solution of benzyl 2-acetamido-2-deoxy-6-(dimethylphosphinyl)-α -D-mannopyranoside, prepared as described above, (100mg, 0.26 mmol) in ethanol/water (10 mL; 1/1) was hydrogenated with 50 mg 10 percent Pd/C for 10 hours. The reaction progress was monitered with TLC (EtOAc/AcOH/H$_2$O, 8/2/1). The catalyst was filtered and the filtrate was concentrated to give 2-acetamido-2-deoxy- 6-(dimethylphosphinyl)-α-D-mannopyroside ( 100 percent yield).

$^1$H NMR D$_2$O) δ 1.51 (6H, d, J=13.6 Hz) 1.94 (3H, s, NAc), 3.45 (2H, m), 3.9 (1H, dd, J=8,4.3 Hz, H- 3), 4.1 (3H, m, H-5,6), 4.87, 4.98 (1H, s, H-1).

Sialic acid aldolase catalyzed aldol condensation of 2-acetamido-2-deoxy-6-(dimethylphosphinyl) -α-D-mannopyroside, prepared as described above, and pyruvic acid was conducted for four days. The product was purified with a Bio Gel P-2 at 4° C. to give Compound 209 in 42 percent yield.

$^1$H NMR D$_2$O) δ 1.48 (6H, d, J=14.2 Hz, P-CH$_3$), 1.67 (1H, dd, J=11,13 Hz, H-3ax), 1.9 (3H, s, NAc), 2.08 (1H, dd, J=5.3, 13 Hz, H-2eq), 3.45 (1H, d, J=9.3 Hz, H-7), 3.8–4.0 (6H, m, H-4,5,6,8,9).

H. 9-Azido-9-deoxy-N-acetylneuraminic acid (Compound 203)

A solution of ManNAc (5.0 g, 2.6 mmol), and Ac$_2$O (10 mL) in pyridine (20 mL) was stirred for 10 hours at room temperature, and the mixture was concentrated, followed by coevaporation with toluene. A solution of the residue, allyl alcohol (2.63 g, 45.2 mmol; 3.1 mL), BF$_3$.OEt$_2$ (1.60 g, 11.3 mmol; 1.39 mL) in CH$_3$NO$_2$ (150 mL) was gently refluxed for 2.5 hours. After cooling, the mixture was concentrated. The residue was chromatographed on silica gel, with toluene-EtOAc (1:2) to give allyl 2-acetamido-3,4,6-tri-O-acetyl- 2-deoxy-α-D-mannopyranoside in 6.47 g (74 percent);

$^1$H NMR (CDCl$_3$) δ 1.99, 2.05, 2.06, 2.12 (3H, s, 3×OAc, NHAc), 4.00–4.03 (1H, m, H-5), 4.07 (1H, dd, J=2.45, 12.24 Hz, H-6a), 4.29 (1H, dd, J=5.34, 12.23 Hz, H-6b), 4.63 (1H, ddd, J=1.43, 4.60, 9.11 Hz, H-2), 4.81 (1H, d, J=1.43 Hz, H-1), 5.11 (1H, t, J=10.18 Hz, H-4), 5.36 (1H, dd, J=4.59, 10.19 Hz, H-3), 5.82 (1H, d, J=9.11 Hz, NHAc); $^{13}$C NMR (CDCl$_3$) δ 20.67, 20.74, 23.33, 50.29, 62.42, 66.05, 68.02, 68.64, 69.11, 98.02 , 118.42 , 132.83, 169.89, 169.96, 170.08, 180.55.

A solution of allyl 2-acetamido-3,4,6-tri-O-acetyl-2-deoxy-α-D-mannopyranoside, prepared as described above, (6.46 g, 16.7 mmol) and methanolic NaOMe (2 mL; 1M solution) in MeOH (100 mL) was stirred for two hours at room temperature, and neutralized by addition of Dowex 50W-X8 [H+]. After the resin was filtered off, the filtrate was concentrated followed by coevaporation with pyridine. A solution of tolylsulfonyl chloride (3.50 g, 18.3 mmol) in pyridine (20 mL) and CH$_2$Cl$_2$ (30 mL) was added dropwise to a cooled solution of the residue in pyridine (30 mL) and CH$_2$Cl$_2$ (50 mL) at 0°–5° C. over 30 minutes, and the mixture was stirred for 10 hours at room temperature then cooled. Acetic anhydride (30 mL) was added to the mixture, and the mixture was stirred for five hours at room temperature. The mixture was concentrated, and the residue was chromatographed on silica gel, with toluene-EtOAc (1:2), to give allyl 2-acetamido-3,4-di-O-acetyl- 2-deoxy-6-O-tolylsulfonyl-α-D-mannopyranoside (3.68 g, 44% );

$^1$H NMR (CDCl$_3$) δ 1.98 (6H, s, 2×Ac), 2.04 (3H, s, Ac), 2.46 (3H, s, CH$_3$ of tosyl), 3.96–4.00 (1H, m, H-4), 4.10 (1H, dd, J=4.50, 11.50 Hz, H-6a), 4.30 (1H, dd, J=2.00, 11.50 Hz, H-6b), 4.62 (1H, ddd, J=1.50, 4.50, 9.00 Hz, H-2), 4.78 (1H, d, J=1.50, 4.50, 9.00 Hz, H-2), 4.78 (1H, d, J=1.50 Hz, H-1), 5.16 (1H, t, J=10.0 Hz, H-4), 5.33 (1H, dd, J=4.50, 10.0 Hz, H-3), 6.03 (1H, d, J=9.50 Hz, NHAc); $^1$C NMR (CDCl$_3$) δ 20.59, 20.78, 21.64, 23.26, 50.00, 65.75, 67.99, 68.10, 68.69, 69.20, 98.04, 118.37, 127.89, 129.89, 132.79, 170.28. HRMS calcd. for C$_{22}$H$_{29}$NO$_{10}$S (M$^+$):500.1590. Found: 500.1590.

A solution of allyl 2-acetamido-3,4-di-O-acetyl- 2-deoxy-6-O-tolylsulfonyl-α-D-mannopyranoside, prepared as described above, (3.68 g, 7.37 mmol) and NaI (2.21 g, 14.7 mmol) was gently refluxed for 10 hours, and cooled. The mixture was concentrated, and the residue was chromatographed on silica gel, with toluene-EtOAc (1:2), to give allyl 2-acetamido-3,4-di-O-acetyl- 2,6-dideoxy-6-iodo-α-D-mannopyranoside (2.96 g, 88 percent);

$^1$H NMR (CDCl$_3$) δ 1.99, 2.05, 2.08 (3H, s, 2×OAc, NHAc), 3.19 (1H, dd, J=7.50, 11.0 Hz, H-6a), 3.35 (1H, dd, J=3.0, 11.0 Hz, H-6b), 3.71 (1H, ddd, J=3.0, 7.5, 10.0 Hz, H-5), 4.63 (1H, ddd, J=1.5, 4.5, 9.5 Hz, H-2), 4.82 (1H, d, J=1.5 Hz, H-1), 4.98 (1H, t, J=10.0 Hz, H-4), 5.36 (1H, d, J=4.5, 10.0 Hz, H-3), 5.79 (1H, d, J=9.5, NHAc); $^{13}$C NMR (CDCl$_3$) δ 5.49, 20.74, 23.34, 50.17, 68.51, 69.11, 70.07, 97.76, 118.54, 132.75, 169.93, 169.99. HRMS calcd for C$_{15}$H$_{22}$NO$_7$I (M$^+$): 456.0519. Found: 456.0520.

0.9 Grams of allyl 2-acetamido-3,4-di-O-acetyl- 2,6-dideoxy-6-iodo-α-D-mannopyranoside, prepared as described above, was dissolved in 10 mL of DMF, 3 equivalents of NaN$_3$ were added and the reaction mixture was heated at 100° C. for 10 hours.

The product exhibited the same Rf value (0.7) as the iodo derivative on TLC (ethyl acetate). However on the TLC, the azido derivative was UV invisible, whereas the iodo derivative was UV visible.

After evaporating of the solvent, the residue was directly applied to the silica gel column chromatography, (hexane/ethyl acetate, ⅔) to give allyl 2-acetamido-3,4-di-O-acetyl-6-azido-2,6-dideoxy-α-D-mannopyranoside (0.5 g, 69 percent);

$^1$H NMR (CDCl$_3$) δ 1.92 (3H, s, NHAc), 1.98 (3H, s,

OAc), 1.99 (3H, s, OAc), 3.2 (1H, dd, J=3, 13 Hz, H-6a), 3.27 (1H, dd, J=6.5, 13 Hz, H-6b), 3.87 (1H, ddd, J=3, 6.5, 11.7 Hz, H-5), 3.95 (1H, dd, J=6, 18 Hz, allyl-H-1a), 4.11 (1H, dd, J=6.18 Hz, allyl-H-1b), 4.54 (1H, ddd, J=2, 5.5, 9.8 Hz, H-2), 4.74 (1H, d, J=2 Hz, H-1), 5.02 (1H, dd, J=9.8, 9.8 Hz, H-4), 5.14 (1H, dd, J=2, 11.3 Hz, allyl-H-3a), 5.23 (1H, dddd, J=6, 6, 11.3, 16 Hz, allyl-H-2), 6.17 (1H, d, J=9.8 Hz, NH); $^{13}$C NMR (CDCl$_3$) δ 20.8, 23.50, 67.68, 68.4, 69.2, 97.5, 117.8, 132.4, 169.8, 170.1.

Ailyl 2-acetamido-3,4-di-O-acetyl-6-azido-2,6-dideoxy-α-D-mannopyranoside, prepared as described above, (0.5 mg) was dissolved in 10 mL methanol containing 0.2M MeONa. After five minutes, Dowex 50 cation exchange resin was added to the mixture to neutralize. The resin was filtered and the filtrate was concentrated to yield allyl 2-acetamido-6-azido-2,6-dideoxy-α-D-mannopyranoside (99 percent).

$^1$H NMR (CDCl$_3$) δ 2.03 (3H, s, NAc), 3.4–3.5 (2H, m, H-6a, 6b ), 3.59 (1H, dd, J=9.8, 9.8 Hz, H-4 ), 3.75 (1H, m, H-5), 4.02 (1H, dd, J=9.8, 5 Hz, H-3), 4.18, 4.39 (1H, dd, J=5, 8.1 Hz, H-2), 4.74 (1H, br-s, OH), 4.8 (1H, s, H-1), 4.87 (1H, br-s, OH), 5.23 (1H, dd, J=1.2, 10 Hz, allyl-H-3a), 5.32 (1H, dd, J=17, 1.2 Hz, allyl-H-3b), 5.90 (1H, dddd, J=6, 6, 10, 17 Hz, allyl-H-2), 6.69 (1H, d, J=8.1, NH).

A suspension of allyl 2-acetamido-6-azido-2,6-dideoxy-α-D-mannopyranoside (200 mg) , 1.2 equivalents PdCl$_2$ and 2.4 equivalents of NaOAc were dissolved in 95 percent acetic acid (5 mL). The reaction was stirred at room temperature overnight and concentrated. The residue was purified with silica gel chromatography, (CHCl$_3$/ethyl acetate/ methanol, 5/2/2 ) , to give 2-acetamido-6-azido-2,6-dideoxy-α-D-mannopyranoside in 31 percent yield.

$^1$H NMR D$_2$O) δ 1.66 (1H, 3H, s, NAc), 3.46 (1H, dd, J=9.8, 9.8 Hz, H-4), 3.45–3.55 (2H, m, H-6a, 6b), 3.82 (1H, m, H-5), 3.87 (1H, dd, J=4.6, 9.8 Hz, H-3), 4.15 (1H, dd, J=4.6 Hz, H-2), 4.88 ( d, J=1.2 Hz, H-1b), 4.97 (s, H-1a).

In a 10 mL of 0.1M potassium phosphate buffer (pH 7.5) containing 10 mM DTT and 0.5M pyruvate were dissolved 50 mg of 6-azido-6-deoxy-N-acetylmannosamine and 1.5 mg of NeuAc aldolase. The starting material was consumed in 14 hours. The solution was lyophilized and the purification was carried out with Bio Gel P-2 gel filtration (3×90 cm) chromatography with a flow rate of 6 mL/40 minutes, at 4° C. The fractions containing the product were pooled and freezed dry to give Compound 203 in 84 percent yield.

$^1$H NMR D$_2$O) δ 1.66 (1H, dd, J=1, 13 Hz, H-3ax), 1.89 (3H, s, NAc), 2.05 (1H, dd, J=4.4, 13 Hz, H-eq), 3.31 (1H, dd, J=5.8, 12 Hz, H-9a), 3.37 (1H, dd, J=1.2, 10 Hz, H-7), 3.45 (1H, dd, J=3.3, 12 Hz, H-9b), 3.7–3.9 (4H, m, H-4, 5, 6, 8). HRMS calcd for C$_{11}$H$_{18}$N$_4$D$_8$ (M-H$^-$): 333.1046. Found: 333.1046.

I. 9-Deoxy-9-fluoro-N-acetylneuraminic acid (Compound 204)

A solution of allyl 2-acetamido-2-deoxy-α-D-mannopyranoside, prepared as described above, 2.0 g, and 1.2 equivalents of tritylchloride was stirred for 10 hours at 72° C. After the reaction mixture was cooled to zero degrees C, 2.5 equivalents of benzoyl chloride were added to the mixture. The reaction mixture was allowed to slowly warm to room temperature in two hours. After the reaction was completed, ice water was added, and the reaction mixture was extracted with ethyl acetate. The organic extracts were washed with iN HCl twice, dried and concentrated. The residue was applied to silica gel chromatography, eluted with hexane/ethyl acetate (10/1) to give allyl 2-acetamido-3,4-di-O-benzoyl-2-deoxy-6-O-trityl-α-D-mannopyroside (23 percent yield).

$^1$H NMR (CDCl$_3$) δ 2.05 (3H, s, NAc) , 3.87 (1H, dd, J=9.8, 9.8 Hz, H-4), 4.05 (1H, dd, J=6, 12 Hz, allyl), 4.1 (3H, m, H-5,6,6'), 4.2 (1H, m, allyl), 4.96 (1H, d, J=11.3 Hz, allyl), 5.07 (1H, d, J=11.3 Hz, Allyl), 5.17 (1H, m, allyl), 5.97 (1H, d, J=7.4 Hz, NMAc).

A suspension of 1.5 g of allyl 2-acetamido-3,4-di-O-benzoyl-2-deoxy-6-O-trityl-α-D-mannopyroside, prepared as described above, in 80 percent acetic acid (10 mL) was allowed to stirred for overnight at room temperature. After the reaction mixture was concentrated, the residue was applied to silica gel chromatography, eluted with hexane/ ethyl acetate (5/1) to give allyl 2-acetamido-3,4-di-benzoyl-2-deoxy-α-Dmannopyranoside (90 percent yield).

$^1$H NMR D$_2$O) δ 2.0 (3H, s, NHAc), 3.78 (2H, m, H-5,6), 4.04 (1H, m, H-6), 4.1 (1H, m, allyl), 4.23 (1H, ddd, J=1.26, 5.73, 12.7 Hz, allyl), 4.88 (1H, dd, J= 4.56, 9.24 Hz, allyl), 4.93 (1H, d, J=1.06 Hz, H-1), 5.24 (1H, dd, J=1.25, 10.5 Hz, allyl), 5.33 (1H, dd, J = 1.4, 17.2 Hz, allyl), 5.63 (1H, dd, J=10.1, 10.1 Hz, H-4), 5.91 (1H, dd, J=4.55, 10.34 Hz, H-3), 5.95 (1H, m, allyl), 6.83 (1H, d, J=9.15 Hz, HNAc).

To a stirred solution of (diethylamino)sulfur trifluoride (0.5 mL) in dry diglyme (2mL) was added a solution of allyl 2-acetamido-3,4-di-benzoyl-2-deoxy-α-D-mannopyranoside, prepared as described above, (100 mg) in dry diglyme (3 mL) at room temperature, and the reaction mixture was stirred for one hour at room temperature and three hours at 40° C. After the starting material was consumed, the reaction mixture was poured onto ice-water and extracted with ethyl acetate. The extract was dried, concentrated, and the residue was applied to silica gel chromatography. After the impurity was eluted with hexane, the product was eluted with ether to give the fluorinated product in 89 percent yield. The product was then dissolved in 5 mL of 1N sodium methoxide in methanol to remove benzoyl group. After 20 minutes, Dowex 50W X-8[H$^+$] was added to neutralize the reaction mixture. The resin was filtered and the filtrate was concentrated to give allyl 2-acetamido-2,6-dideoxy-6-fluoro-α-D-mannopyranoside in 99 percent yield. The product (50 mg), 1.2 equivalents of palladium (II) acetate, and 2.5 eq of sodium acetate in 95 percent acetic acid (5 mL) were stirred at 50° C. for 18 hours, and the solvent was removed under vacumn. The residue was applied to silica gel chromatography, eluted with ethyl acetate/methanol (⅔) to obtain 2-acetamido-2,6-di-deoxy-6-fluoro-α-D-mannopyranoside in 73 percent yield.

$^1$H NMR D$_2$O) δ 1.9 (3H, s, NAc), 3.5 (1H, dd, J=10.3, 10.3 Hz, H-4), 3.72 (1H, m, H-5), 3.93 (1H, dd, J=4.5, 10.3 Hz, H-3), 4.16 (1H, d, J=4.5 Hz, H-2), 4.46 (2H, m, H-6), 4.9, 5.0 (1H, s, H-1).

A solution of 2-acetamido-2,6-di-deoxy-6-fluoro-α-D-mannopyranoside, prepared as described above, (20 mg) and pyruvic acid sodium salt (255 mg, 30 equivalents) in 0.1M potassium phosphate buffer (pH 7.5, 10 mL) in the presence of N-acetylneuraminic acid aldolase (100 U) was incubated at 37° C. for 8 days. The reaction mixture was lyophilized and chromatographed with Bio Gel P-2 column to give Compound 204 in 22 percent yield. The physical data were in accordance with reported values. Sharma et al., Carb. Res., 175:25 (1988).

The foregoing is intended as illustrative of the present invention but not limiting. Numerous variations and modifications may be effected without departing from the true spirit and scope of the novel concepts of the invention.

We claim:
1. An oligosaccharide having structural Formula I:

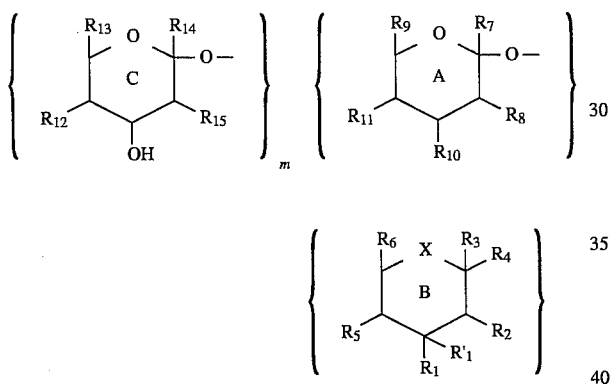

I wherein X is S, or $NR_{16}$, wherein $R_{16}$ is hydrogen, $C_1$–$C_{12}$ acyl or $C_1$–$C_{12}$ alkyl, or $NR_{16}$ is a $C_1$–$C_{12}$ alkyl N-oxide;

$R_1$ is absent, hydroxyl or d-linked fucosyl;

$R'_1$ is hydrogen;

$R_2$ is absent, hydroxyl or acetamido;

$R_3$ and $R_4$ are independently hydrogen, hydroxyl, or a saturated or unsaturated alkoxide or alkoxy alkoxide containing up to five carbon atoms with the proviso that at least one of $R_3$ and $R_4$ is hydrogen;

$R_5$ is absent, hydrogen, hydroxyl, or methyl;

$R_6$ is absent, hydrogen, hydroxymethyl or methyl;

$R_7$ is hydrogen or carboxyl;

$R_8$ is hydrogen, hydroxyl or acetamido;

$R_9$ is selected from the group consisting of hydroxymethyl, methyl and trihydroxypropyl, 3-acetoxy-1,2-dihydroxypropyl, 3-1actyloxy-1,2dihydroxypropyl, 3-azido-1,2-dihydroxypropyl, and 3-fluoro-1,2-dihydroxypropyl when $R_8$ is hydrogen and $R_{11}$ is acetamido;

$R_{10}$ is absent or hydroxyl;

$R_{11}$ is absent, hydroxyl or acetamido;

$R_{12}$ is hydroxyl or acetamido;

$R_{13}$ is selected from the group consisting of hydroxymethyl, and trihydroxypropyl, 3-acetoxy-1,2-dihydroxypropyl, 3-1actyloxy-1,2-dihydroxypropyl, 3-azido-1,2-dihydroxypropyl, and 3-fluoro-1,2-dihydroxypropyl when R15 is hydrogen and $R_{12}$ is acetamido;

$R_{14}$ is hydrogen or carboxyl;

$R_{15}$ is hydrogen, hydroxyl or acetamido; and m is zero or one such that when m is zero, ring C is absent and when m is one, ring C is present;

with the provisos (a) that one of substituents $R_1$, $R_2$ and $R_5$ or a hydroxyl group of $R_6$ is absent from ring B and ring B is joined to ring A through a glycosidic bond to the ring B carbon of the absent substituent, and that a numbered substituent or hydroxyl is only absent when ring A is joined to ring B at the position of that substituent or hydroxyl except as enumerated herein; (b) that when m is one, one of substituents $R_{10}$ and $R_{11}$ or a hydroxyl group of $R_9$ is absent from ring A and ring C is joined to ring A through a glycosidic bond to the ring A carbon of the absent substituent or hydroxyl, and that numbered substituent or hydroxyl is only absent when ring C is joined to ring A at the position of that substituent or hydroxyl, or a second of $R_1$, $R_2$, $R_5$ or a hydroxyl of $R_6$ is absent and ring C is joined to ring B through a glycosidic bond to the ring B carbon of the second absent substituent or hydroxyl; and (c) that when X is $NR_{16}$, ring A is beta-bonded to ring B and, (i) $R_1$ is hydroxyl, $R'_1$ is hydrogen, $R_2$ is hydroxyl or acetamido, $R_3$ and $R_4$ are both hydrogen, $R_6$ is hydroxymethyl and rings A and B are joined through a glycosidic bond at $R_5$, or (ii) $R_1$ is hydrogen or hydroxyl, $R_2$ is present, $R_3$ and $R_4$ are both hydrogen, $R_5$ is hydrogen, hydroxyl or methyl, $R_6$ is hydrogen or methyl but only one of $R_5$ and $R_6$ is methyl, $R_{16}$ is hydrogen, $C_1$–$C_{12}$ alkyl, $C_1$–$C_{12}$ acyl, or $NR_{16}$ is a $C_1$–$C_{12}$ alkyl N-oxide, and ring A is linked to ring B through a glycosidic bond at $R'_1$, $R_2$ or $R_5$.

2. The oligosaccharide of claim 1 wherein m is zero.

3. The oligosaccharide of claim 1 wherein m is 1.

4. The oligosaccharide of claim 3 wherein rings C and A are both glycosidically linked to ring B and two of $R_1$, $R_2$ $R_5$ or a hydroxyl of $R_6$ are absent.

5. The oligosaccharide of claim 4 wherein said oligosaccharide corresponds to structural Formula V

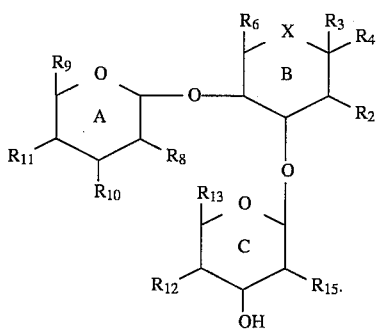

V

6. The oligosaccharide of claim 5 wherein ring C is α-linked fucosyl, ring A is β-linked galactosyl, X is S, $R_2$ is hydroxyl, $R_3$ and $R_4$ are hydrogen and hydroxyl, and $R_6$ is hydroxymethyl.

7. An oligosaccharide having structural Formula II:

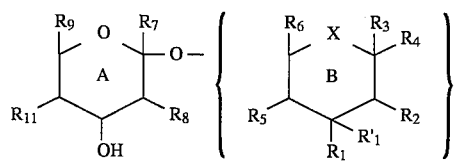

II wherein X is S, or $NR_{16}$, wherein $R_{16}$ is hydrogen, $C_1$–$C_{12}$ acyl or $C_1$–$C_{12}$ alkyl or $NR_{16}$ is a $C_1$–$C_{12}$ alkyl N-oxide;

$R_1$ is absent, hydroxyl or a-linked fucosyl;

$R'_1$ is hydrogen;

$R_2$ is absent, hydroxyl or acetamido;

$R_3$ and $R_4$ are independently hydrogen, or a saturated or unsaturated alkoxide or alkoxy alkoxide containing up to 5 carbon atoms, with the proviso that at least one of $R_3$ and $R_4$ is hydrogen;

$R_5$ is absent, hydrogen, hydroxyl, or methyl;

$R_6$ is absent, hydrogen, hydroxymethyl or methyl;

$R_7$ is hydrogen or carboxyl;

$R_8$ is hydrogen, hydroxyl or acetamido;

$R_9$ is selected from the group consisting of hydroxymethyl, methyl and trihydroxypropyl, 3-acetoxy-1,2-dihydroxypropyl, 3-lactyloxy-1,2-dihydroxypropyl, 3-azido-1,2-dihydroxypropyl, and 3-fluoro-1,2-dihydroxypropyl when $R_8$ is hydrogen and $R_{11}$ is acetamido;

$R^{11}$ is hydroxyl or acetamido;

with the provisos (a) that one of substituents $R_1$, $R_2$, $R_5$ or a hydroxyl group of $R_6$ is absent from ring B and ring B is joined to ring A through a glycosidic bond to the ring B carbon of the absent substituent, and that a numbered substituent or hydroxyl is only absent when ring A is joined to ring B at the position of that substituent or hydroxyl except as enumerated herein; and (b) that when X is $NR_{16}$, ring A is beta-bonded to ring B and, (i) $R_1$ is hydroxyl, $R_1$ is hydrogen, $R_2$ is hydroxyl or acetamido, $R_3$ and $R_4$ are both hydrogen, $R_6$ is hydroxymethyl and rings A and B are joined through a glycosidic bond at $R_5$, or (ii) $R_1$ is hydrogen or hydroxyl, $R_2$ is present, $R_3$ and $R_4$ are both hydrogen, R5 is hydrogen, hydroxyl or methyl, $R_6$ is hydrogen or methyl but only one of $R_5$ and R6 is methyl, $R_{16}$ is hydrogen, $C_1$–$C_{12}$ alkyl, $C_1$–$C_{12}$ acyl, or $NR_{16}$ is a $C_1$–$C_{12}$ alkyl N-oxide, and ring A is linked to ring B through a glycosidic bond at $R'_1$, $R_2$ or $R_5$.

8. The oligosaccharide of claim 7 wherein $R_{11}$ is hydroxyl, and the substituent groups have the stereochemical configuration shown in structural Formula IV

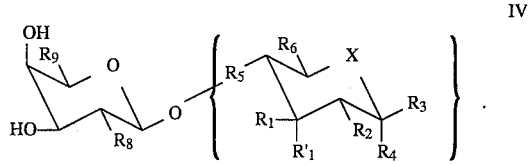

IV

The oligosaccharide of claim 8 wherein X is S.

9. The oligosaccharide of claim 8 wherein X is S.

10. The oligosaccharide of claim 8 wherein X is NH.

11. A composition comprising an aqueous medium having dispersed therein an oligosaccharide having structural Formula II:

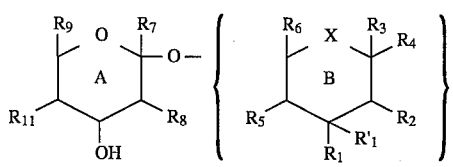

II wherein X is S or $NR_{16}$, wherein $R_{16}$ is hydrogen, $C_1$–$C_{12}$ acyl or $C_1$–$C_{12}$ alkyl or $NR_{16}$ is a $C_1$–$C_{12}$ alkyl N-oxide;

$R_1$ is absent, hydroxyl, or d-linked fucosyl;

$R'_1$ is hydrogen or;

$R_2$ is absent, hydroxyl or acetamido;

$R_3$ and $R_4$ are independently hydrogen, hydroxyl, or a saturated or unsaturated alkoxide or alkoxy alkoxide containing up to 5 carbon atoms, with the proviso that at least one of $R_3$ and $R_4$ is hydrogen;

$R_5$ is absent, hydrogen, hydroxyl, or methyl;

$R_6$ is absent, hydrogen, hydroxymethyl or methyl;

$R_7$ is hydrogen or carboxyl;

$R_8$ is hydrogen, hydroxyl or acetamido;

$R_9$ is selected from the group consisting of hydroxymethyl, methyl and trihydroxypropyl, 3-acetoxy-1,2-dihydroxypropyl, 3-lactyloxy-1,2-dihydroxypropyl, 3-azido-1,2-dihydroxypropyl, and 3-fluoro-1,2-dihydroxypropyl when $R_8$ is hydrogen and $R_{11}$ is acetamido;

$R^{11}$ is hydroxyl or acetamido;

with the provisos (a) that one of substituents $R_1$, $R_2$, $R_5$ or a hydroxyl group of $R_6$ is absent from ring B and ring B is joined to ring A through a glycosidic bond to the ring B of the absent substituent, and that a numbered substituent or hydroxyl is only absent when ring A is joined to ring B at the position of that substituent or hydroxyl except as enumerated herein; and (b) that when X is $NR_{16}$ Ring A is beta-bonded to ring B and, (i) $R_1$ is hydroxyl, $R'_1$ is hydrogen, $R_2$ is hydroxyl or acetamido, $R_3$ and $R_4$ are both hydrogen, $R_6$ is hydroxymethyl and rings A and B are joined through a glycosidic bond at Rs, or (ii) $R_1$ is hydrogen or hydroxyl, $R_2$ is present, $R_3$ and $R_4$ are both hydrogen, $R_5$ is hydrogen, hydroxyl or methyl, $R_6$ is hydrogen or methyl but only one of $R_5$ and $R_6$ is methyl, $R_{16}$ is hydrogen, $C_1$–$C_{12}$ alkyl, $C_1$–$C_{12}$ acyl, or $NR_{16}$ is a $C_1$–$C_{12}$ alkyl N-oxide, and ring A is linked to ring B through a glycosidic bond at $R'_1$, $R_2$ or $R_5$.

* * * * *